(12) United States Patent
Uesugi et al.

(10) Patent No.: US 7,248,366 B2
(45) Date of Patent: Jul. 24, 2007

(54) METHOD FOR MARKING DEFECT AND DEVICE THEREFOR

(75) Inventors: Mitsuaki Uesugi, Yokosuka (JP); Shoji Yoshikawa, Hachioji (JP); Masaichi Inomata, Yokohama (JP); Tsutomu Kawamura, Tokyo (JP); Takahiko Oshige, Kawasaki (JP); Hiroyuki Sugiura, Yokohama (JP); Akira Kazama, Yokohama (JP); Tsuneo Suyama, Fukuyama (JP); Yasuo Kushida, Fukuyama (JP); Shuichi Harada, Fukuyama (JP); Hajime Tanaka, Fukuyama (JP); Osamu Uehara, Fukuyama (JP); Shuji Kaneto, Hiroshima (JP); Masahiro Iwabuchi, Fukuyama (JP); Kozo Harada, Fukuyama (JP); Shinichi Tomonaga, Fukuyama (JP); Shigemi Fukuda, Fukuyama (JP)

(73) Assignee: NKK Corporation, Tokyo (JP)

( * ) Notice: Subject to any disclaimer, the term of this patent is extended or adjusted under 35 U.S.C. 154(b) by 709 days.

(21) Appl. No.: 09/956,737

(22) Filed: Sep. 17, 2001

(65) Prior Publication Data
US 2002/0154308 A1    Oct. 24, 2002

Related U.S. Application Data

(63) Continuation of application No. PCT/JP00/01559, filed on Mar. 15, 2000.

(30) Foreign Application Priority Data

| Mar. 18, 1999 | (JP) | ................... 11-072962 |
| Jun. 25, 1999 | (JP) | ................... 11-179776 |
| Jul. 1, 1999 | (JP) | ................... 11-187961 |
| Oct. 5, 1999 | (JP) | ................... 11-283703 |
| Jan. 21, 2000 | (JP) | ................... 2000-017739 |

(51) Int. Cl.
*G01N 21/00* (2006.01)
*G01N 21/84* (2006.01)

(52) U.S. Cl. .................... 356/431; 356/237.2

(58) Field of Classification Search .. 356/237.2–237.5, 356/431
See application file for complete search history.

(56) References Cited

U.S. PATENT DOCUMENTS

| 2,930,228 | A | | 3/1960 | Lawrence et al. | |
| 3,609,532 | A | * | 9/1971 | Van Kirk et al. | ........... 324/215 |
| 3,675,118 | A | * | 7/1972 | Booth | ........... 324/226 |
| 4,175,729 | A | * | 11/1979 | Karlsson | ........... 266/51 |
| 4,318,439 | A | * | 3/1982 | Hiroshima et al. | ...... 164/154.2 |
| 4,516,855 | A | | 5/1985 | Korth | |
| 4,817,424 | A | | 4/1989 | Pellatiro | |
| 5,394,654 | A | * | 3/1995 | Shimbara et al. | ........... 451/6 |
| 5,680,473 | A | | 10/1997 | Kanzaka et al. | |
| 5,716,262 | A | * | 2/1998 | Kiba | ........... 451/103 |
| 6,013,308 | A | * | 1/2000 | Saito | ........... 427/8 |
| 6,122,562 | A | * | 9/2000 | Kinney et al. | ........... 700/121 |

FOREIGN PATENT DOCUMENTS

| DE | 1669111 | * | 11/1970 |
| EP | 0 032 975 A2 | | 8/1981 |
| JP | 49-073356 A | | 7/1974 |
| JP | 54-155162 A | | 12/1979 |
| JP | 57-166533 A | | 10/1982 |
| JP | 58-204353 A | | 11/1983 |
| JP | 60-228943 A | | 11/1985 |
| JP | 62-278444 A | | 12/1987 |
| JP | 04-291138 A | | 10/1992 |
| JP | 05-196581 A | | 8/1993 |
| JP | 2052/1995 U | | 1/1995 |
| JP | 08-178867 A | | 7/1996 |
| JP | 09-166552 A | | 6/1997 |
| JP | 09-178667 A | | 7/1997 |
| JP | 10-176998 A | | 6/1998 |
| JP | 10-277912 A | | 10/1998 |
| JP | 11-183398 A | | 7/1999 |

| | | | |
|---|---|---|---|
| JP | 11-319943 A | 11/1999 | |

OTHER PUBLICATIONS

F. Obeso et al; Intelligent On-Line Surface Inspection On A Skinpass Mill; Iron and Steel Engineer Association of Iron and Steel Engineers, Pittsburgh, PA vol. 74, No. 9; Sep. 1, 1997; pp. 29-35.

M. Simonis et al; Surface Inspection for Automatic Detection and Classification of Defects on Hot Strip; Sep. 1, 1998; Steel Times International; pp. 24 & 28; vol. 22, No. 5.

B. Backelandt et al; Systeme d'inspection automatique de surface SIAS; Automatic Strip Surface Inspection System Cahiers D'Informations Techniques De La Revue De Metallurgie, Revue De Metallurgie, Paris, France, vol. 93, No. 10, Oct. 1, 1996, pp. 1265-1269.

International Preliminary Examination Report dated Aug. 27, 2001, issued in corresponding International Application No. PCT/JP00/01559 filed Mar. 15, 2000. Applicant: NKK Corporation et al; Inventors: Mitsuaki Uesugi et al.

* cited by examiner

*Primary Examiner*—Layla G. Lauchman
(74) *Attorney, Agent, or Firm*—Frishauf, Holtz, Goodman & Chick, P.C.

(57) ABSTRACT

The defect marking method comprises the steps of: installing a surface defect tester to detect surface flaw and a marker device to apply marking at defect position, in a continuous processing line of steel sheet; detecting the surface flaw on the steel sheet using the surface defect tester; determining defect name, defect grade, defect length, and defect position in the width direction of the steel sheet, on the basis of thus detected flaw information, further identifying the defect in terms of harmful defect, injudgicable defect, and harmless defect; applying tracking of the defect position for each of the harmful defect and the injudgicable defect; and applying marking to the defect position. The defect marking device comprises a defect inspection means having plurality of light-receiving parts and a signal processing section, and a marking means.

37 Claims, 35 Drawing Sheets

FIG. 5

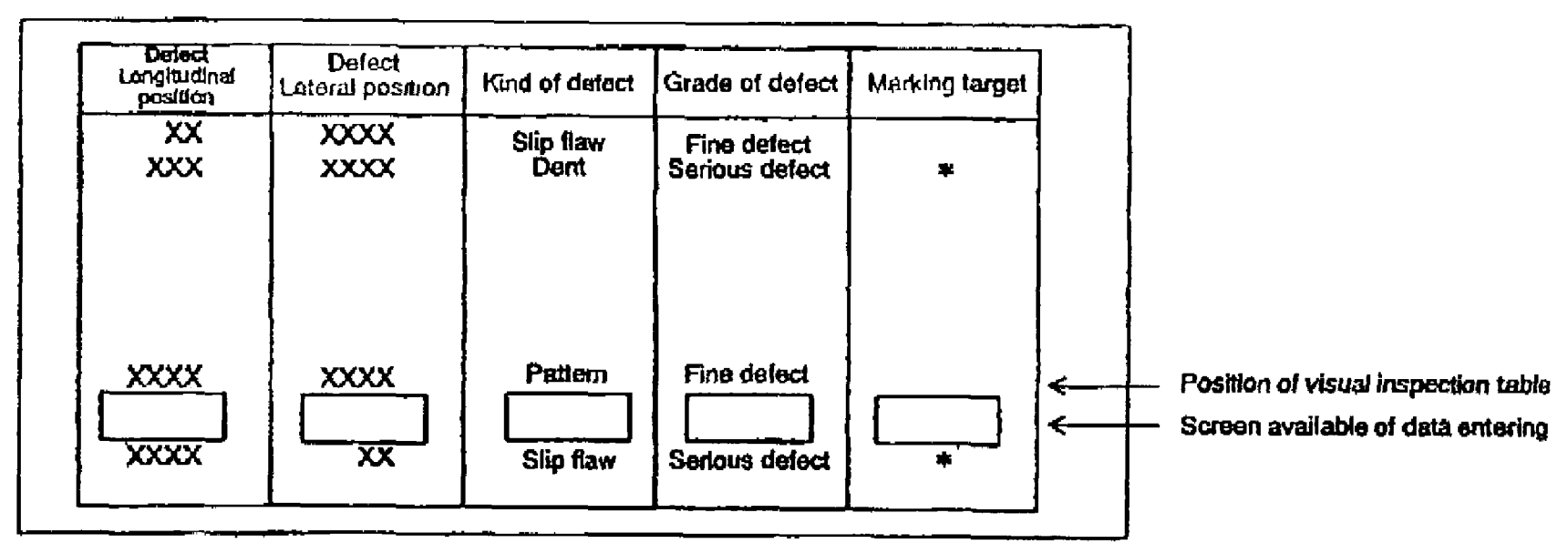

| Defect Longitudinal position | Defect Lateral position | Kind of defect | Grade of defect | Marking target |
|---|---|---|---|---|
| XX<br>XXX | XXXX<br>XXXX | Slip flaw<br>Dent | Fine defect<br>Serious defect | * |
| XXXX<br>XXXX | XXXX<br>XX | Pattern<br>Slip flaw | Fine defect<br>Serious defect | * |

↑ Position of visual inspection table
↑ Screen available of data entering (a) TEMPERED PART (SPECULAR REFLECTION)

(b) NON-TEMPERED PART (SPECULAR DIFFUSIONAL REFLECTION)

(c) OBSERVED ANGLE DISTRIBUTION

FIG.39
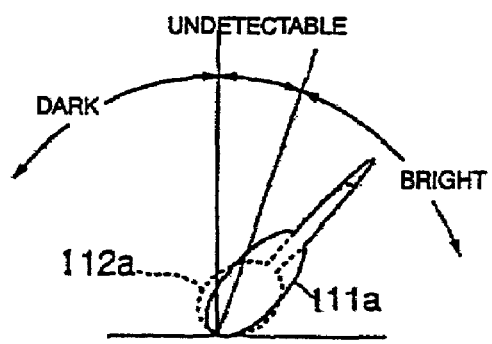
(a)
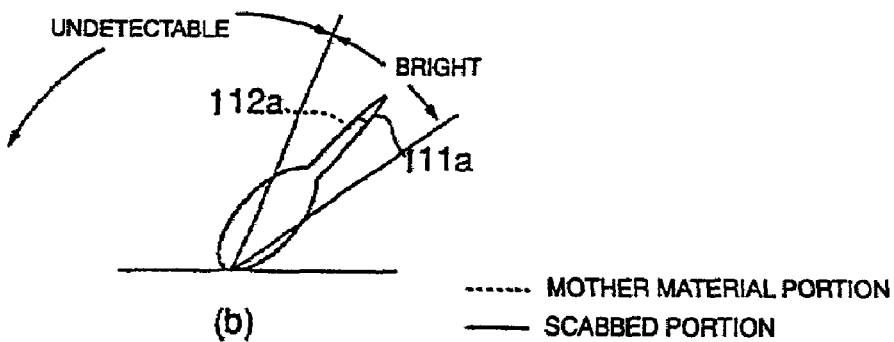
(b)
······ MOTHER MATERIAL PORTION
——— SCABBED PORTION
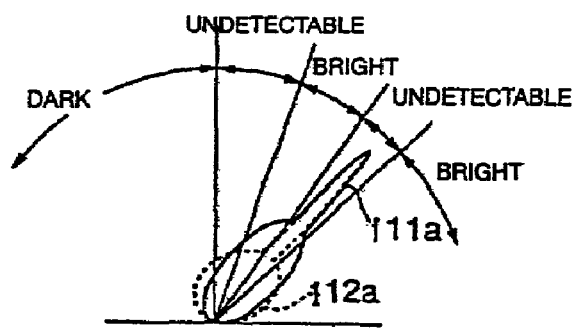
(c)

----- MOTHER MATERIAL PORTION
——— SCABBED PORTION $\theta' - \xi = \xi - \theta$
$\therefore \theta' = -\theta + 2\xi$ (a)

(b)

METHOD FOR MARKING DEFECT AND DEVICE THEREFOR

This application is a continuation application of International Application PCT/JP00/01559 filed Mar. 15, 2000.

FIELD OF THE INVENTION

The present invention relates to a method for marking defect on a steel sheet in a steel making process line and to a device therefor.

DESCRIPTION OF RELATED ARTS

Cold-rolled steel sheets manufactured by cold-rolling are subjected to inspection of surface defects over the whole length of coil thereof for quality assurance. JP-A-5-196581, (the term "JP-A" referred herein signifies the "Unexamined Japanese patent publication"), discloses a method for detecting surface defects and internal defects of steel sheets. According to the disclosure, detection of the surface defects on a steel sheet is conducted by scanning the surface of steel sheet which is running through a manufacturing line, in width direction thereof by laser light, by converting the reflected light to voltage intensity using a photoelectric transfer device such as CCD element, then by judging the presence/absence and the degree of the defect based on the voltage signals. The internal defects of a steel sheet are detected by computing the defect depth in the thickness direction of the steel sheet and the defect size using a magnetic particle tester. Usually, the result of the defect inspection is displayed on a CRT or the like as information in terms of defect position, defect name, defect grade, and the like, or is printed in a document.

It is impossible to obtain products completely free from defects. Consequently, the products are shipped after removing portions of harmful defect for the buyer concerned on the basis of the defect information displayed on a CRT or the like in the manufacturing line, or after removing the portions of harmful defect for the buyer concerned by applying re-inspection in succeeding stage on the basis of the above-described defect information. Alternatively, a document of the above-described harmful detect information is submitted to the buyer concerned, together with the coil that contains harmful defect portions, thus letting the buyer remove the harmful defects.

In the case that the harmful defect portions are removed in the manufacturing line or in succeeding stage, since there is no definite standard of the degree of harm for the surface defects, the removal of harmful defect portions is practiced in an excessive action from the standpoint of quality assurance. Also there are cases of not-removing harmful defects caused from a miss-judgment such as overlooking and from a state of very close to injudicable defect. Furthermore, removal of harmful defect portions raises problems such as reduction in the coil weight and reduction in the work efficiency of the buyer.

On the other hand, the buyer needs to work on coils while referring the documented data of defect information, which induces troublesome work and, in some cases, may result in treatment of coils leaving defects non-detected.

JP-A-4-291138 discloses a marking device that sprays a paint on flawed portions of steel sheets. According to the disclosure, marking is done by spraying a paint to flawed portions of the steel sheets detected by a flaw detection device, thus enabling the buyer to readily identify the flawed portion on re-inspection by the buyer.

Since, however, the method for marking according to JP-A-4-291138 does not give confirmation whether the marking was correctly given or not, and an abnormal marking induces further troubles to the buyer. In addition, paint spray generates shade of color on marking, which may induce dents, in an area with large quantity of applied paint, even at normal portions after the paint is dried. For the case of spray marking, an oiled steel sheet cannot leave any marking on the surface thereof because the paint is sprayed on an oil film, though that kind of problem does not occur on a steel sheet free of applied oil. When marking is given on all of the flawed portions, the marking is also given to the defects of harmless to the buyer, which induces disadvantages including reduction in work efficiency.

There are inspection methods for surface defects, disclosed in JP-A-58-204353, JP-A-60-228943, JP-A-8-178867, JP-A-57-166532, and JP-A-9-166552. All of these disclosed methods aim to detect flaws having significant surface irregularity or to detect flaws with the presence of foreign matter such as oxide film. Thus, for pattern-like scabbed flaws or the like which do not have significant surface irregularity, these methods cannot surely identify all the flaws.

As means for applying marking to flawed portions and singular parts generated on a metal material, there are commercially available apparatuses such as ink jet printer and ink dot marking device.

When an ink jet printer is used, kinds and colors of ink are limited because special inks are required owing to various conditions such as charging the inks. Nevertheless, when the manufactured metal materials are used for automobile steel sheets, ink performance and color may be specified for convenience of customer's inspection.

For example, if an ink is under limitations such that the ink should have excellent quick drying property, the ink should not be blotting on applying oil, and the ink should be blue, respective special inks should be developed to satisfy the customer's conditions. The development of that special inks needs long time and much money, which is difficult to practically respond to the request.

In addition, since the ejection part of the ink is necessary to maintain clean, significant cost and time should be consumed for maintenance. Accordingly, when an ink jet printer is used, a special ink has to be used, so that color and kind of the ink cannot readily be changed.

SUMMARY OF THE INVENTION

It is an object of the present invention to provide a method for defect marking that readily and surely identifies harmful defects, and an apparatus therefor.

It is another object of the present invention to provide a surface flaw marking device that detects pattern-like scabs having no significant surface irregularity such as surface crack, burr, and curl up, thus allowing to notifying the defect information to the user concerned with a simple means, also to provide a metal strip with marking, and to provide a method for manufacturing thereof.

To attain the objects, firstly, the present invention provides a method for marking defect, which comprises the steps of:

(a) installing a surface defect tester to detect surface flaw and a marker device to apply marking at defect position, in a continuous processing line of steel sheet;

(b) detecting the surface flaw on the steel sheet using the surface defect tester;

(c) calculating to determine defect name, defect grade, defect length, and defect position in width direction of the steel sheet, on the basis of thus detected flaw information, further identifying the defect in terms of harmful defect, injudicable defect, and harmless defect;

(d) tracking the defect position for each of the harmful defect and the injudicable defect; and (e) marking the defect position at a moment that the defect reaches the marker device.

Secondly, the present invention provides a method for defect marking, which comprises the steps of:

(a) calculating to determine defect name, defect grade, defect length, and defect position in width direction of a coil for a surface defect thereon, in a processing line provided with a surface defect tester, further identifying the defect in terms of harmful defect and injudicable defect;

(b) feeding the coil to a steel sheet continuous processing line provided with a marker device for applying marking; and (c) marking to the defect position at a moment that the harmful defect or the injudicable defect reaches the marker device, on the basis of the information of preliminarily identified harmful defect or injudicable defect.

Thirdly, the present invention provides a flaw inspection device, which comprises:

a plurality of light-receiving devices that identify reflected lights coming from an inspection plane of a metal strip under two or more of optical conditions different from each other; and a signal processing section that judges presence/absence of surface flaw on the inspection plane, based on a combination of reflected light components identified under these optical conditions different from each other.

Fourthly, the present invention provides a defect marking device, which comprises:

a flaw inspection means comprising plurality of light-receiving parts that identify reflected lights coming from an inspection plane of a metal strip under two or more of optical conditions different from each other, and a signal processing section that judges presence/absence of surface flaw on the inspection plane based on a combination of reflected light components identified under these optical conditions different from each other; and a marking means that applies marking that indicates information relating to the flaw on the surface of the metal strip.

Fifthly, the present invention provides a method for manufacturing metal strip with defect marking, which comprises the steps of:

(a) identifying reflected lights coming from an inspection plane of a metal strip under two or more of optical conditions different from each other;

(b) judging presence/absence of surface flaw on the inspection plane based on a combination of reflected light components identified; and (c) marking information relating to the flaw on the surface of the metal strip based on the judgment result.

Sixthly, the present invention provides a method for working metal strip, which comprises the steps of:

(a) identifying reflected lights coming from an inspection plane of a metal strip under two or more of optical conditions different from each other;

(b) judging presence/absence of surface flaw on the inspection plane based on a combination of reflected light components identified;

(c) marking information relating to the flaw on the surface of the metal strip;

(d) winding the marked metal strip to prepare a coil;

(e) rewinding the coil to detect the marking, and specifying a specific range of the metal strip based on the information given by the marking; and (f) applying specified working to a residual portion of the metal strip after avoiding or removing the specified range.

Seventhly, the present invention provides a metal strip with marking, which has, on a portion that shows an abnormality compared with a portion of normal combination of surface reflected light components separated under two or more optical conditions different from each other, marking indicating information relating to a flaw on the surface thereof.

Eighthly, the present invention provides a metal strip with marking, which has, on a portion that gives an abnormal quantity of light for one or both components of a specular reflection component on surface and a specular-diffuse reflection component on plurality of micro-area reflection surfaces, a marking indicating information relating thereto.

Ninthly, the present invention provides a marking device for applying marking a flawed portion and a singular part on an inspection body, detected by an inspection device, comprises a marker pen;

a penholder to which the marker-pen is detachably mounted; a penholder lifting mechanism for ascending/descending the penholder together with the marker-pen;

a protective cap being capable of opening/closing to protect a pen tip of the marker-pen; and a shutter mechanism to open/close the protective cap linking with the penholder lifting mechanism.

Tenthly, the present invention provides a marking device for applying marking a flawed portion and a singular part on a metal member, detected by an inspection device in a continuous manufacturing line of a metal material, comprises:

a marker pen;

a penholder to which the marker-pen is detachably mounted;

a penholder lifting mechanism for ascending/descending the penholder together with the marker-pen;

a protective cap being capable of opening/closing to protect a pen tip of the marker-pen; and a shutter mechanism to open/close the protective cap linking with the penholder lifting mechanism.

BRIEF DESCRIPTION OF THE DRAWINGS

FIG. 5 is an example of CRT display relating to the Best Mode 1 according to the present invention.

FIG. 39($a$) through ($c$) show angle distribution of specular reflection component and specular-diffuse reflection component, at scabbed portion and mother material, relating to the Best Mode 2 according to the present invention.

BEST MODE FOR CARRYING OUT THE INVENTION

Best Mode 1

Figure 1:
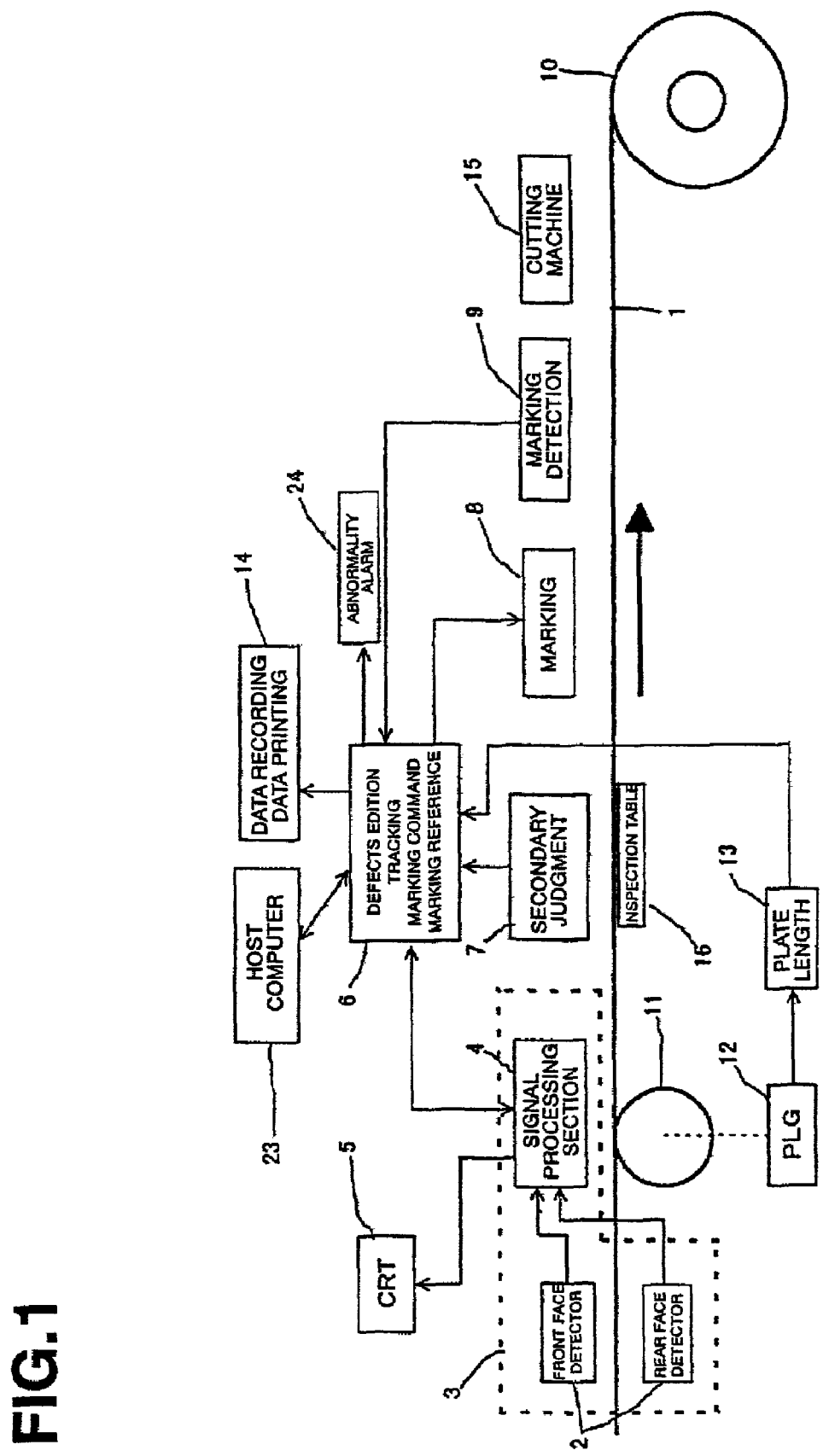
FIG. 1 illustrates an arrangement of main facilities of the first coiling line for steel sheet relating to the Best Mode 1 according to the present invention.

The main constitution of the Best Mode 1 is the following.

(1) A defect marking method comprises the steps of: installing a surface defect tester to detect surface flaw, an ink marker device to apply marking by an ink at defect position, and an internal defect tester to detect internal defect of a steel sheet, in a continuous processing line of the steel sheet; detecting the surface flaw on the steel sheet using the surface flaw tester; calculating to determine defect name, defect grade, defect length, and defect position in width direction of the steel sheet, on the basis of thus detected flaw information, further identifying the defect in terms of harmful defect, injudicable defect, and harmless defect; detecting the internal flaw of the steel sheet using the internal defect tester; calculating to determine the defect length and the defect position in the width direction of the steel sheet, on the basis of thus detected flaw information, further identifying the defect in terms of harmful defect and harmless defect; applying tracking of the defect position for each of the harmful defect and the injudicable defect; and applying marking with ink to the defect position at a moment that the defect reaches the ink marker device.

(2) A defect marking method comprises that, in the method for defect marking of (1), the surface flaw is subjected to identification of harmful defect, injudicabie defect, and harmless defect, on the basis of the defect name, the defect grade, the defect length, the defect position in width direction of the steel sheet, the defect position on each of front face and rear face of the steel sheet, and the use of the steel sheet, and that the internal flaw is subjected to identification of harmful defect and harmless defect, on the basis of the defect length, the defect position in the width direction of the steel sheet, and the use of the steel sheet.

(3) A defect marking method comprises that, in a line provided with a surface defect tester and an internal defect tester, the surface defect is subjected to calculation to determine the defect name, the defect grade, the defect length, and the defect position in width direction of a coil, further to identification of the defect in terms of harmful defect and injudicable defect, and that the internal defect is subjected to calculation to determine the defect length and the defect position in the width direction of the coil, further to identification of the defect in terms of harmful defect and harmless defect, further that the coil in which the harmful defect and the harmless defect are identified is fed to a continuous processing line of steel sheet, provided with an ink marker device that applies marking with ink, thus applying marking with ink to the defect position at a moment that the harmful defect or the injudicable defect reaches the marker device, on the basis of the information of preliminarily identified harmful defect or injudicable defect.

(4) A defect marking method comprises that, in the above-described (1) through (3), an inspector applies re-judgment of defect which was identified as an injudicable defect by the surface defect tester to identify harmful defect and harmless defect, and applies marking with ink to the position of harmful defect.

(5) A defect marking method comprises that, in the above-described (1) through (4), an alarm is generated to a defect that is identified as an injudicable defect by the surface defect tester, and an automatic speed reduction is conducted, then an inspector applies re-judgment on the injudicable defect.

(6) A defect marking method comprises that, in the above-described (4) and (5), on applying re-judgment by the inspector for the defect that is identified as an injudicable defect by the surface defect tester, display of the defect image and display of defect position for the defect are generated.

(7) A defect marking method comprises that, in the above-described (1) through (7), the position of defect marking is changed on the basis of the information of defect in the width direction given by the surface defect tester and by the internal defect tester.

(8) A defect marking method comprises that, in the above-described (1) through (7), the position of defect marking is changed on the basis of the use of the steel sheet.

(9) A defect marking method comprises that, in the above-described (1) through (8), the marking is applied separating the harmful defect from the injudicable defect.

(10) A defect marking method comprises that, in the above-described (1) through (9), the marking is applied separating the harmful defect from the injudicable defect by changing color from each other.

(11) A defect marking method comprises that, in the above-described (1) through (10), the color of defect marking is changed with respective grades of steel sheet.

(12) A defect marking method comprises that, in the above-described (1) through (11), a defect marking detection device is installed at downstream side of the ink marker device, thus monitoring the marking state.

(13) A defect marking method comprises that, in the above-described (1) through (12), the threshold value of the defect marking detection device is changed with respective grades of steel sheet.

(14) A defect marking method comprises that, in the above-described (1) through (13), the ink marker device and the defect marking device are installed as a set, thus letting these devices track the defect marking position.

(15) A defect marking method comprises that, in the above-described (1) through (14), an ink drying device is installed at downstream side of the defect marking.

(16) A defect marking method comprises that, in the above-described (1) through (15), the ink marker device, the defect marking device, and the ink drying device are installed as a set, thus letting these devices track the defect marking position.

(17) A defect marking method comprises that, in the above-described (1) through (16), the threshold value of harmful defect and of harmless defect is changed with respective uses of steel sheet.

(18) A method for working a coil with defect marking comprises that a coil with defect marking marked in accordance with the method of above-described (1) through (17) is fed to a facility provided with a defect marking detection device to reflect the defect information detected by the defect marking detection device on the defect removal work.

(19) A method for working a coil with defect marking comprises that, a coil with defect marking marked in accordance with the method of above-described (1) through (17) is fed to a facility provided with a defect marking detection device and a cleaning means, and the defect information detected by the defect marking detection device is reflected on the defect removal work, and an inspector applies re-judgment on the injudicable defect, then, when the judgment concluded as the harmless defect, the marking ink is cleaned by the cleaning means.

(20) A defect marking method comprises that, in the above-described (1) through (19), (excluding (10), (15), and (16)), an abrasive member marker device that applies marking using an abrasive member is installed instead of the ink marker device using ink, thus applying marking with the abrasive member instead of applying marking with ink.

FIGS. 1 through 4 illustrate examples of arrangement of main facilities of continuous treatment line of steel sheet, being used in the description of the Best Mode 1 according to the present invention.

In FIG. 1, the reference number 3 designates a surface defect tester equipped with a detector 2 each one on front face and rear face of a steel sheet 1 and with a signal processing section 4, the reference number 5 designates a CRT, 6 designates a centralized control panel, 7 designates a secondary judgment entering device, 8 designates a defect marking device (an ink marker device), 9 designates a defect marking detection device, 10 designates a tension reel, 11 designates a transfer roll, 12 designates a pulse generator, 13 designates a arithmetic unit for detecting steel sheet transfer distance, 14 designates an external memory device, 15 designates a cutting machine, and 16 designates an inspection table.

Figure 2:
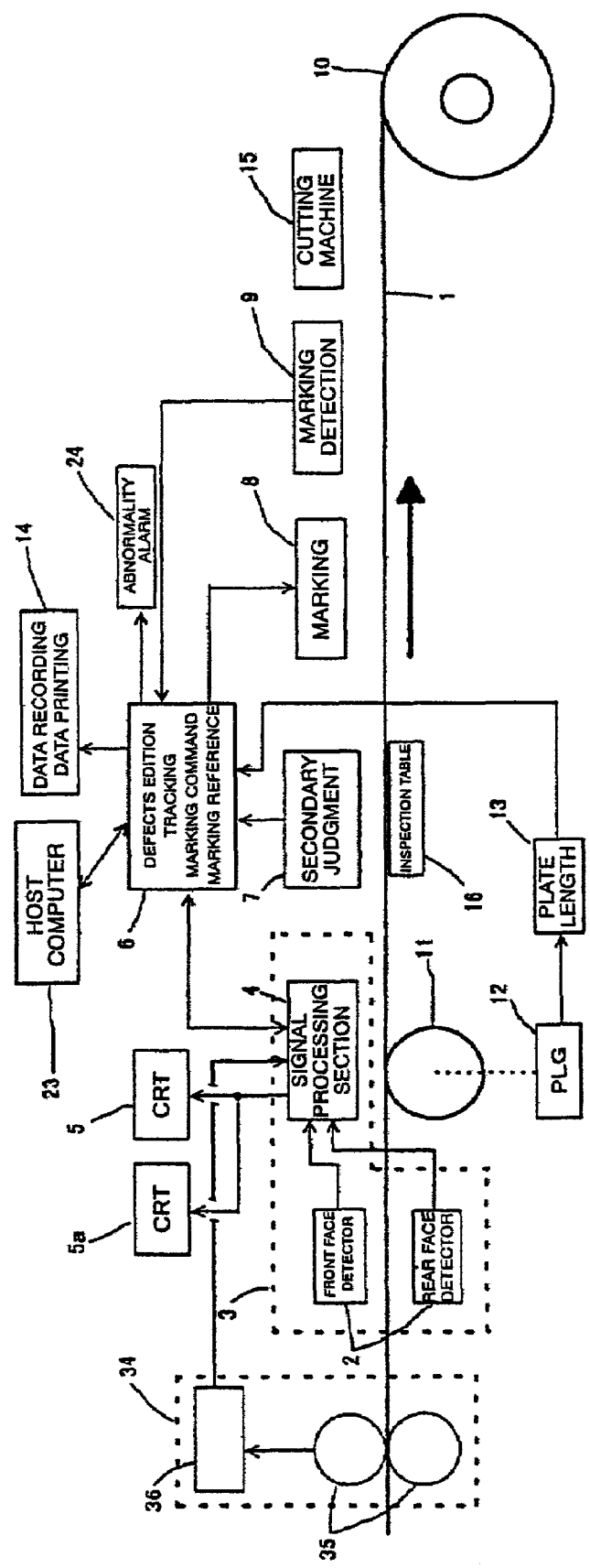
FIG. 2 illustrates an arrangement of main facilities of the second coiling line for steel sheet relating to the Best Mode 1 according to the present invention.
Figure 3:
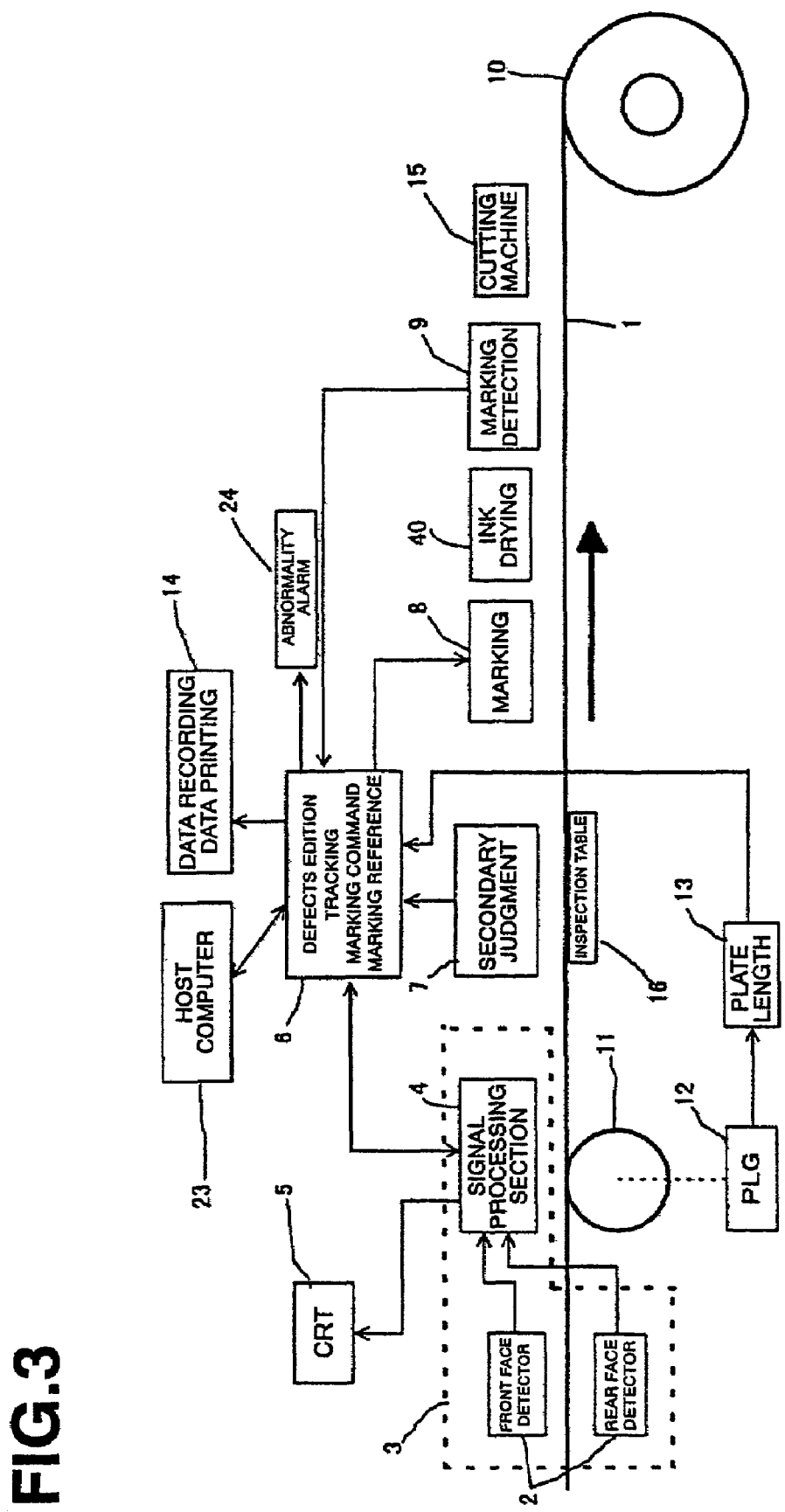
FIG. 3 illustrates an arrangement of main facilities of the third coiling line for steel sheet relating to the Best Mode 1 according to the present invention.
Figure 4:
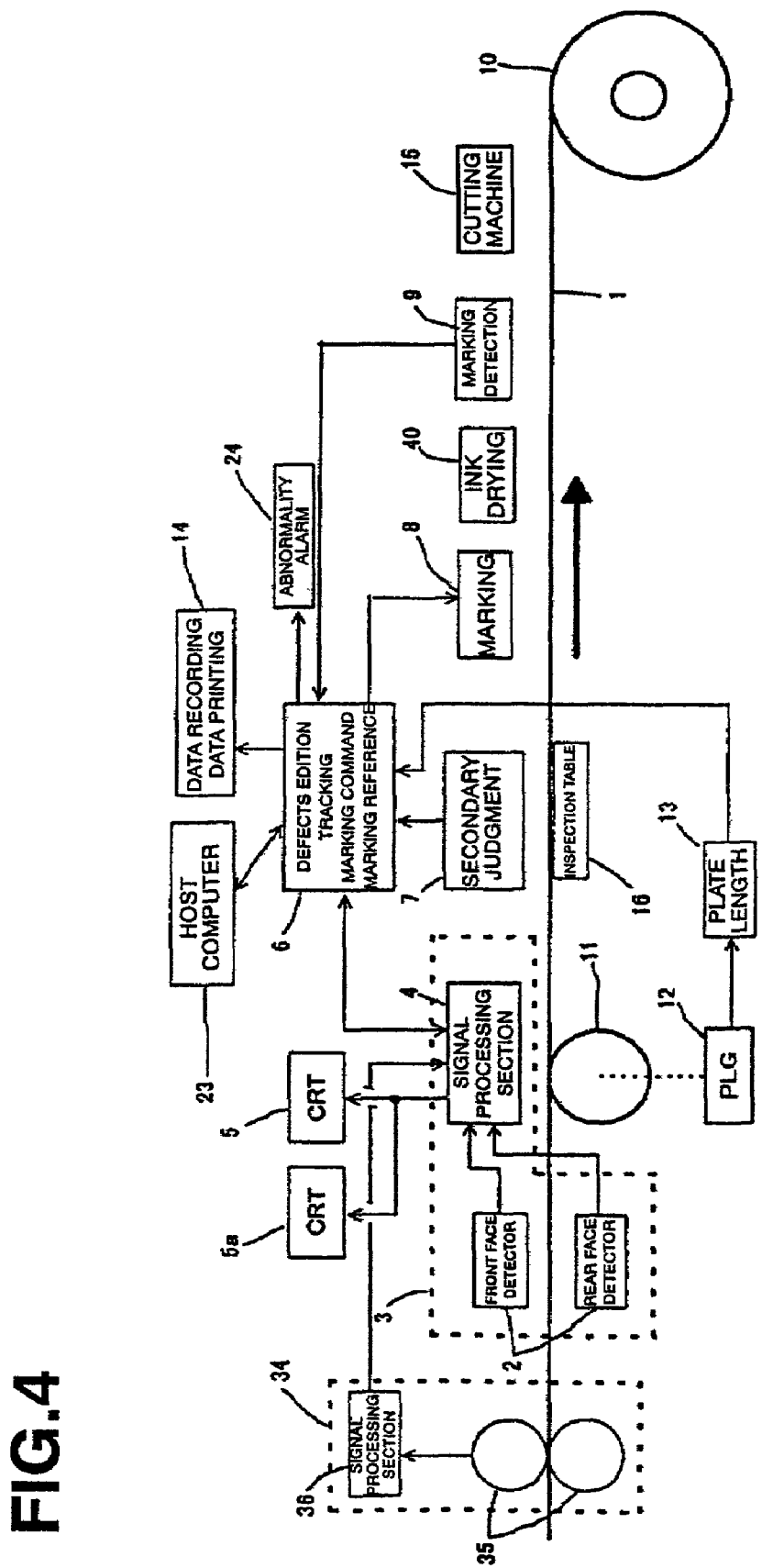
FIG. 4 illustrates an arrangement of main facilities of the fourth coiling line for steel sheet relating to the Best Mode 1 according to the present invention.

FIG. 2 illustrates the facilities of FIG. 1 further providing a magnetic particle tester (an internal defect tester) 34 equipped with a magnetic sensor 35 which detects internal defect of the steel sheet 1, and with a signal processing section 36. The facilities of FIG. 3 and FIG. 4 have an ink drying device 40 to dry the marked ink at downstream side of the defect marking device (ink marker device) 8.

In the facilities shown in FIGS. 1 through 4, the detector 2 positioned at each of front face and rear face of the steel sheet, in the surface defect tester 3, detects flaws that are candidates of defects on each of front face and rear face of the steel sheet 1, and sends the detected signals to the signal processing section 4.

The signal processing section 4 calculates the identification of defect name, defect grade, defect length, and defect position in the width direction of the steel sheet, based on the signals obtained from characteristic quantity, exceeding a specific threshold value of the signals, of defect candidates.

The magnetic sensor 35 of the magnetic particle tester 34 detects an internal defect of the steel sheet 1, and sends the detected signals to the signal processing section 36. The signal processing section 36 calculates the identification of defect length and defect position in the width direction of the steel sheet, based on the signals obtained from characteristic quantity, exceeding a specific threshold value of the signals, of defect candidates, then transmits the calculation result to the signal processing section 4 of the surface defect tester 3.

Furthermore, calculation of marking command is conducted based on the marking information sent from a host computer 23, including the marking target defect name (including internal defect in the case of providing the internal defect tester 34), defect grade, and edge insensitive zone, for each of front face and rear face, and on the result of calculation on the basis of defect information detected by the surface defect tester 3, or further on the basis of grade and use of the steel sheet.

Both the calculated marking command and the calculated defect information are displayed on the screen of CRT 5. Furthermore, the defect generation signal, the defect information, and the defect position are generated on the centralized control panel 6.

The rotational speed of the transfer roll 11 that transfers the steel sheet 1 is measured by the pulse generator 12, and the steel sheet feed length is calculated by the arithmetic unit for detecting steel sheet transfer distance 13, then the result is generated to the centralized control panel 6. The centralized control panel 6 edits the above-described defect information, identifies harmful defect and injudicable defect, (harmful defect for internal defect: and so forth), based on the defect name and the defect grade, and furthermore, if needed, identifies harmful defect and injudicable defect considering the defect position information and the use of the steel sheet for each of front face and rear face. If necessary, the centralized control panel 6 gives judgment of necessity of marking for the harmful defect and the identified injudicable defect which were identified.

The centralized control panel 6 tracks the defect position based on the feed length of steel sheet transmitted from the arithmetic unit for detecting steel sheet transfer distance 13, and generates alarm of arriving the injudicable defect at the re-judgment place (inspection table). If necessary, automatic speed reduction is given, and the defect image is displayed on CRT 5, thus easing the defect judgment of worker.

When a defect portion arrives at the secondary judgment place (inspection table) 16, the worker conducts the secondary judgment under visual inspection, and confirms the detection result of the surface defect tester 3 on the CRT 5, thus giving conclusion of correct/incorrect result. If the result differs in the comparison, correction is given, and the corrected result is entered to the secondary judgment entering device 7, further is generated to the centralized control panel 6. FIG. 5 is an example of CRT display. The defect information given in the figure is the information of the surface defect tester 3, and the blank column in the figure is the place to enter the secondary judgment result.

The centralized control panel 6 conducts re-edition of the above-described defect information on the basis of the corrected information, and identifies harmful defect and injudicable defect based on the defect name and defect grade. Furthermore, the centralized control panel 6 conducts tracking of the positions of harmful defect and injudicable defect, (the defect judged to have marking in the case that the judgment of presence/absence of marking is given), based on the feed length of the steel sheet 1 obtained from the rotational speed of the transfer roll 11, thus moves the defect marking device 8 and the defect marking detection device 9 to a place of defect before the defect portion passes through the defect marking device 8. Then, the centralized control panel 6 generates a start signal to start the defect marking device 8 at the moment that the defect part passes through the defect marking device 8.

Based on the above-described start signal, the defect marking device 8 starts, thus conducting marking on the harmful defect and the injudicable defect synchronously with the timing that the harmful defect and the injudicable defect pass through the defect marking device 8.

The defect marking device 8 begins applying marking at a moment of receiving the marking command. Marking is given by applying ink onto the steel sheet 1 by directly pressing a felt impregnated with ink against the steel sheet 1. Even on a coil applied with oil, marking is surely applied on the surface of the steel sheet. Since there is no problem of shading in color, which occurs in paint coating, no dent appears on the surface of the steel sheet. The felt wears by direct contact with the steel sheet 1. If the marking exceeds a standard length, the centralized control panel 6 generates an alarm to notify the worker to replace the felt.

Considering the tracking accuracy of the defect position, the marking length is set so as the defect portion not to come outside of the defect marking. The facility adds 0.5 m to the defect length judged by the centralized control panel 8 on each of front and rear edges of the defect, taking into account of the tracking information, and generates a command for applying marking by 1 m longer than the actual defect length. If the defect is a pattern of point-like defects each having not more than several millimeters in length, the command is to apply marking by adding 0.25 m to each of front and rear edges of the defect.

For the length of marking, it is preferred to determine thereof under a negotiation with the buyer concerned. The centralized control panel 6 conducts monitoring of allowable number of markings and allowable length of marking, as additional control items. If these monitoring values exceed allowable limit, the centralized control panel 6 generates an abnormality alarm to an alarm device 24.

The host computer 23 conducts control of individual coils on the basis of the information coming from the centralized control panel 6, and gives judgment of shipment.

Figure 6:
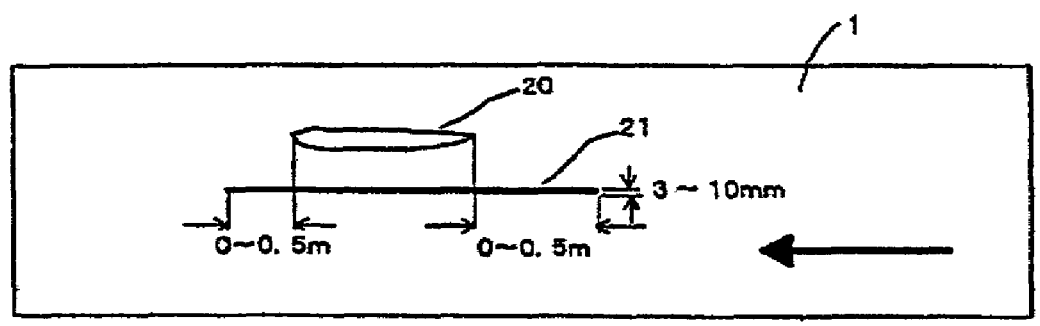
FIG. 6 illustrates a relation state between the defect position and the defect marking position relating to the Best Mode 1 according to the present invention.

FIG. 6 shows a state of the defect position and the defect marking position. The harmful defect 20 is within the display range of the defect marking 21 in the length direction.

From the standpoint of easiness in visual detection and of easiness in detection by the defect marking detection device 9, the line width of the marking is most preferably in a range of from 3 to 10 mm. From the point of felt wear and ink visibility, the pressing force of felt is most preferably in a range of from 150 to 500 g.

The defect marking device 8 may be a single unit. However, it is preferable that two of the defect marking device 8 are installed to prepare two kinds of ink, thus changing the marking color at need.

By installing two units of defect marking device 8 with two kinds of ink color, the ink color is changed responding to the defect grades, (for example, red ink marking is applied to the case that the harmful defect for the buyer is distinctive, and blue ink marking is applied to the case of injudicable defect), or the ink color is changed responding to the grades of the steel sheets, (for example, black ink marking is applied to the case of white steel sheet as seen in the electrolytic galvanized steel sheet, and white ink marking is applied to the case of black steel sheet as seen in the alloyed hot dip galvanized steel sheets), thus improving the work efficiency of the working with identifying the defect by visual inspection and of the identification working with the defect marking detection device. In press-working or the like, the defect marking may be removed by blanking even when the defect exists. Therefore, the defect marking is preferably applied to arbitrary position in the width direction of the steel sheet independent of the place of harmful defect. Any kind of ink is necessary be selected to vanish by a weak alkali cleaning agent. In some uses of the steel sheets, however, cleaning agent other than that of weak alkali may be applied.

For applying marking with ink as described above, once the ink is dried, no problem occurs. However, ordinary inks take few seconds to dry. If the ink is not dried, the ink is transferred onto the roll or the coil. If oil is applied before the ink is dried, the ink cannot be dried, and the ink is transferred onto a tension reel by winding the coil therearound. The problem is completely solved by installing an ink drying device at downstream side of the ink marker device to dry the ink marked.

Figure 7:
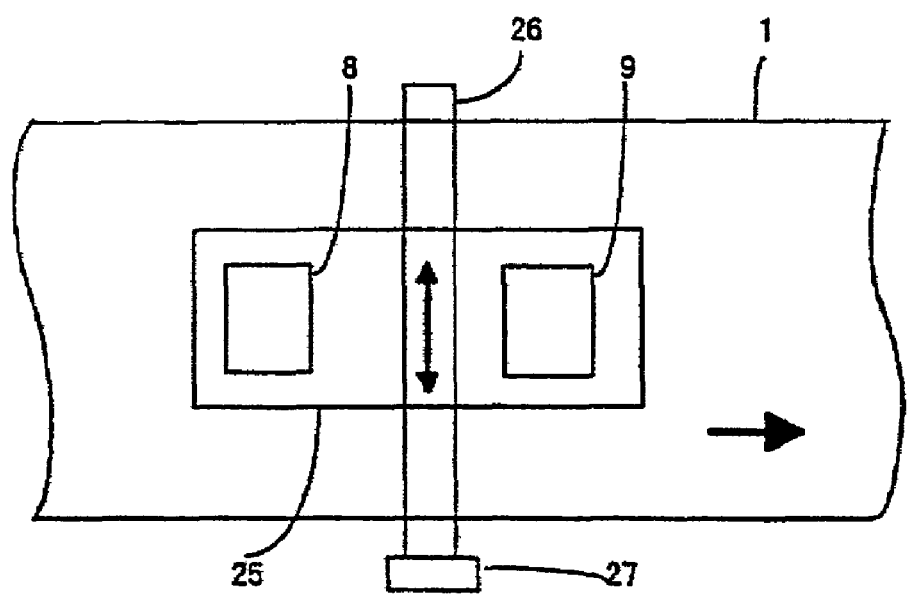
FIG. 7 illustrate an example of arrangement of each one unit of the defect marking device and the defect marking detection device, relating to the Best Mode 1 according to the present invention.

FIG. 7 illustrates an example of arrangement of each one unit of the defect marking device 8 and the defect marking detection device 9. Both the defect marking device 8 and the defect marking detection device 9 are located at the same position in the width direction of the steel sheet 1 on a table 25, which devices are movable in the width direction of the steel sheet at a position that is commanded by a marking command, via a transfer device 26 which is driven by a motor 27.

Figure 8:
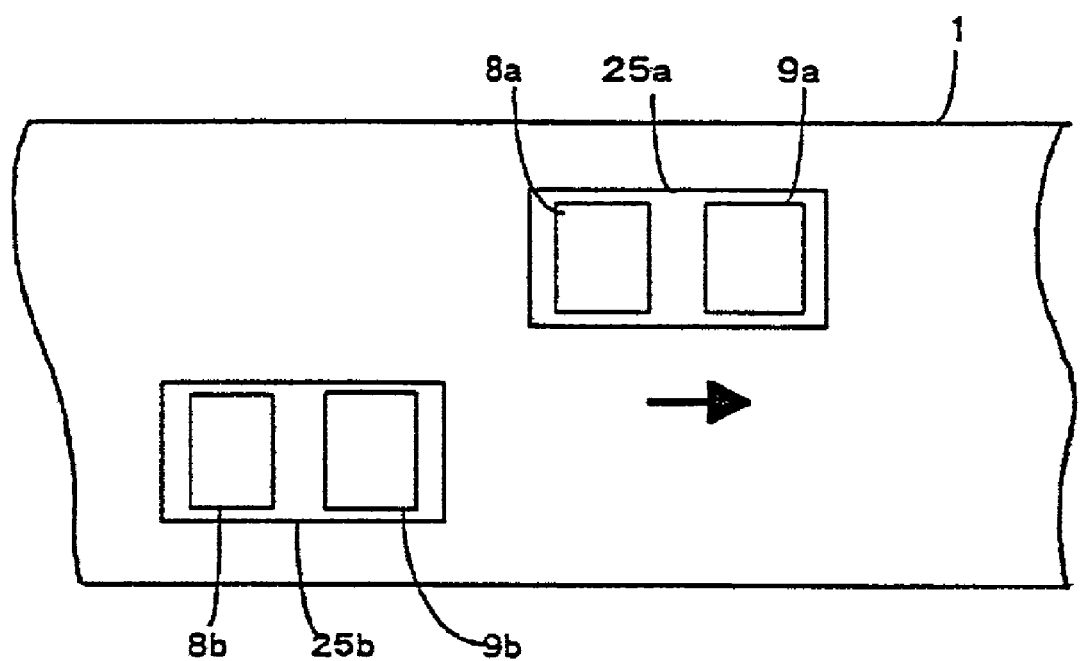
FIG. 8 illustrate an example of arrangement of each two units of the defect marking device and the defect marking detection device, relating to the Best Mode 1 according to the present invention.

FIG. 8 illustrates an example of arrangement of each two units of the defect marking device and the defect marking detection device. Each pair of the defect marking device 8*a* and the defect marking detection device 9*a*, and the defect marking device 8*b* and the defect marking detection device 9*b*, are installed at the same position in the width direction of the steel sheet 1 on respective table 25*a* and table 25*b*, which devices are movable in the width direction of the steel sheet separately as in the case of the facility of FIG. 7.

Figure 9:
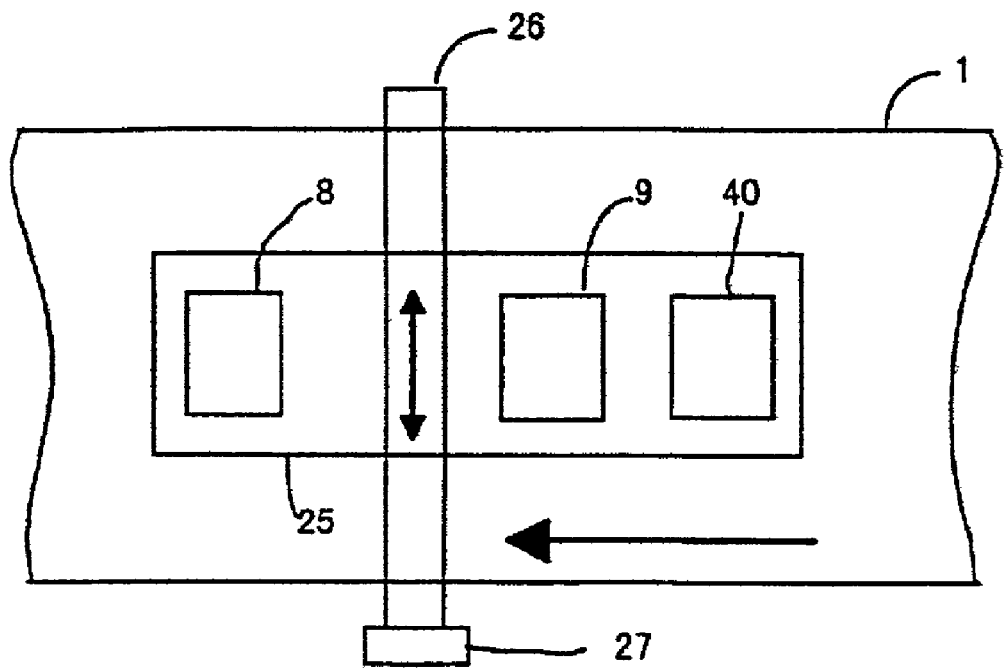
FIG. 9 illustrate an example of arrangement of each one unit of the defect marking device and the ink drying device, relating to the Best Mode 1 according to the present invention.
Figure 10:
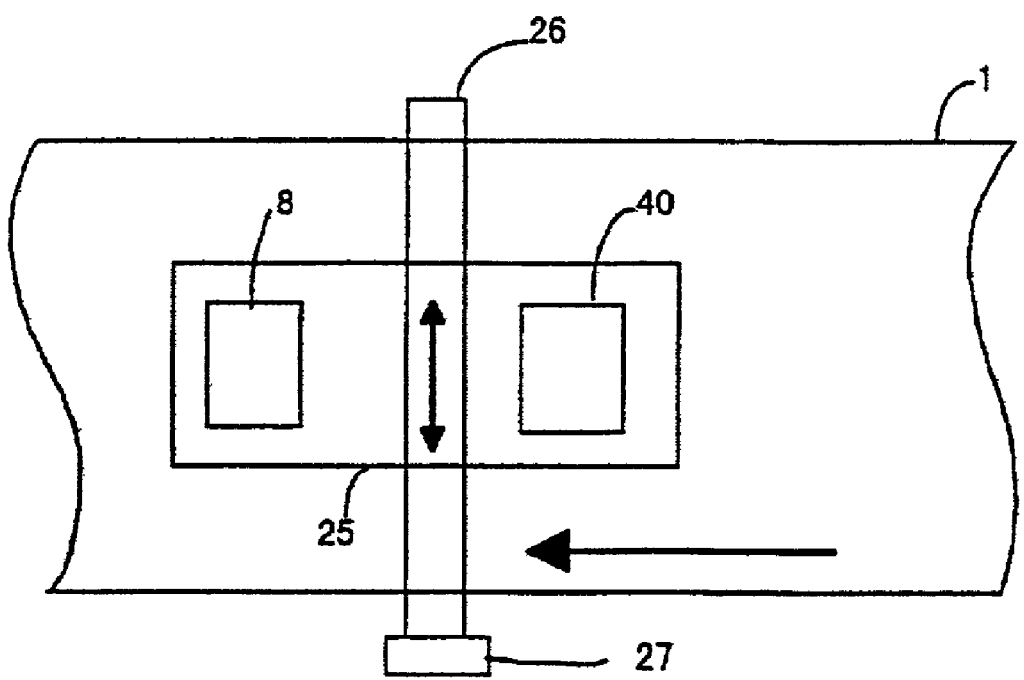
FIG. 10 illustrate an example of arrangement of each one unit of the defect marking device, the defect marking detection device, and the ink drying device, relating to the Best Mode 1 according to the present invention.

FIG. 9 and FIG. 10 show that the ink drying device is located at downstream side of the defect marking device. In FIG. 9, the defect marking device 8 and the ink drying device 40 are located at the same position in the width direction of the steel sheet 1 on the table 25. In FIG. 10, the defect marking device 8, the ink drying device 40, and the defect marking detection device 9 are located at the same position in the width direction of the steel sheet 1 on the table 25. For both facilities, these devices are movable in the width direction of the steel sheet to a position commanded by the marking command, via the transfer device 26 driven by the motor 27.

Figure 11:
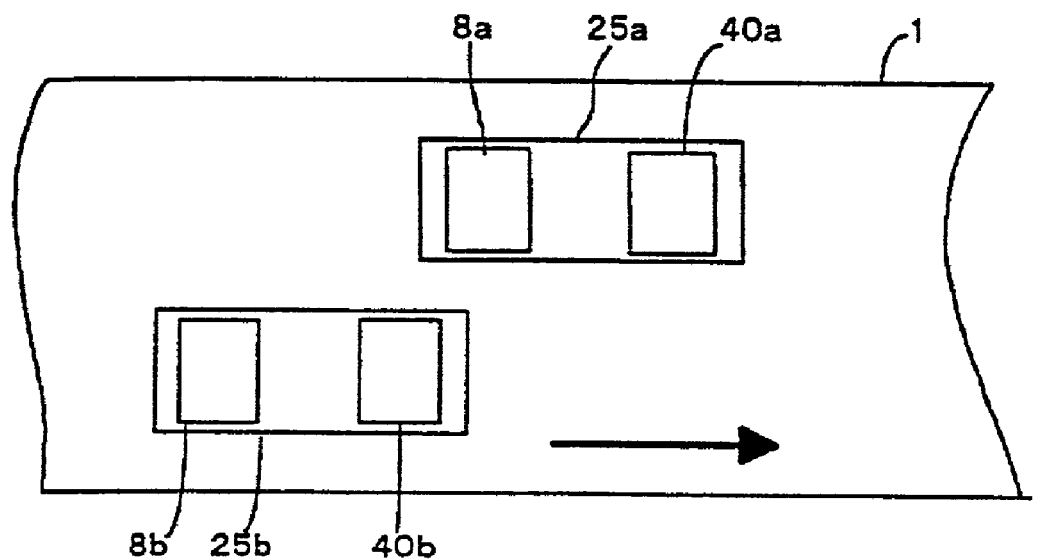
FIG. 11 illustrate an example of arrangement of each two units of the defect marking device and the ink drying device, relating to the Best Mode 1 according to the present invention.
Figure 12:
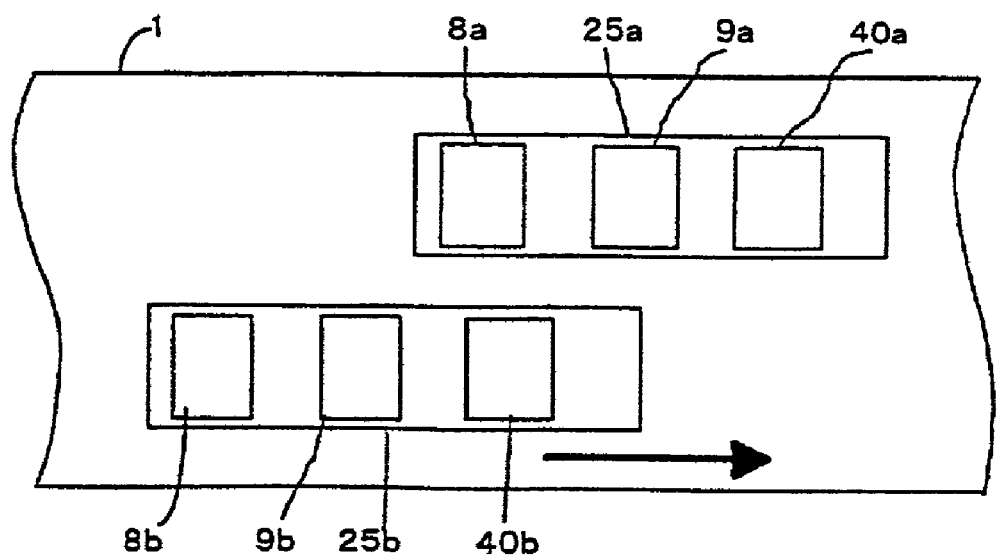
FIG. 12 illustrate an example of arrangement of each two units of the defect marking device, the defect marking detection device, and the ink drying device, relating to the Best Mode 1 according to the present invention.

The defect marking device 8, the ink drying device 40, and the defect marking detection device 9 may be installed by two units there each. FIG. 11 shows that each pair of the defect marking device 8*a* and the ink drying device 40*a*, and the defect marking device 8*b* and the ink drying device 40*b*, are located at the same position in the width direction of the steel sheet 1 on respective tables 25*a* and 25*b*. FIG. 12 shows that each set of the defect marking device 8*a*, the ink drying device 40*a*, and the defect marking detection device 9*a*, and the defect marking device 8*b*, the ink drying device 40*b*, and the defect marking detection device 9*b*, are located at the same position in the width direction of the steel sheet 1 on respective tables 25*a* and 25*b*, thus allowing these devices to move in the width direction of the steel sheet, separately in each set to each other, as in the case of FIG. 8.

Figure 13:
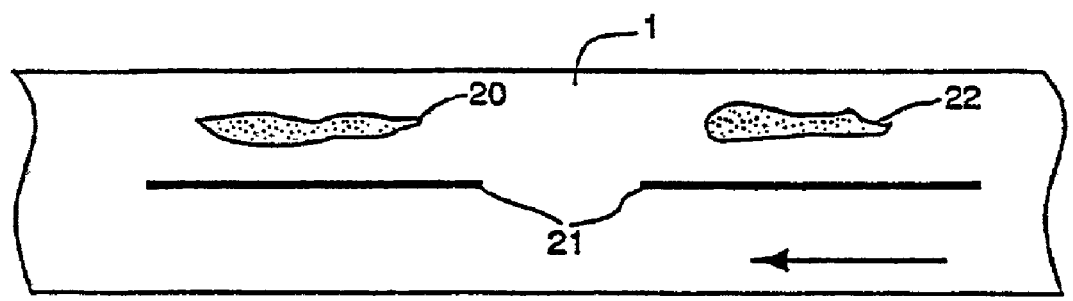
FIG. 13 illustrates an example of applying marking on defect portions using a single unit of defect marking device relating to the Best Mode 1 according to the present invention.

FIG. 13 illustrates an example of applying marking on defect portions and defect marking position using a single unit of defect marking device. In the figure, same ink color is used to indicate the harmful defect 20 and the injudicable defect 22 as the defect marking 21.

Figure 14:
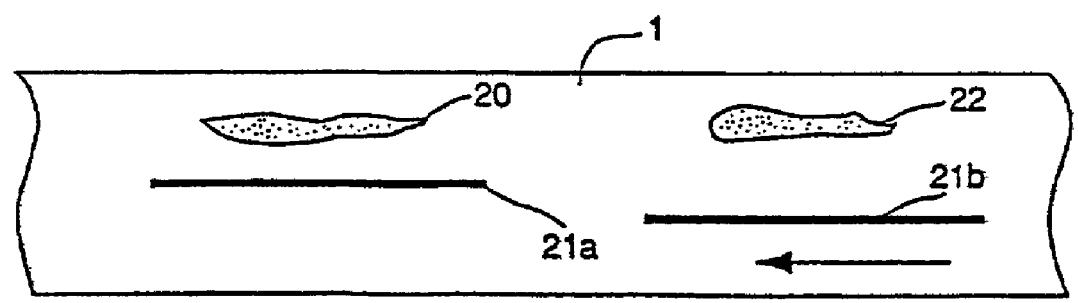
FIG. 14 illustrates an example of applying marking separately on a harmful defect and an injudicable defect using two units of defect marking device relating to the Best Mode 1 according to the present invention.

FIG. 14 illustrates an example of applying marking with different ink colors using two units of defect marking devices. The harmful defect 20 is expressed by the defect marking 21*a* (red, for example), and the injudicable defect 22 is expressed by the defect marking 21*b* (blue, for example).

The defect marking detection device 9 continuously monitors the state of defect marking, monitors the marking length, the blurred ink, and the presence/absence of marking at non-defect place, then generates the monitored result on the centralized control panel 6. To improve the detection accuracy of the defect marking, it is preferred to correct the threshold value of the defect marking detection device responding to the grades of the steel sheets. The centralized control panel 6 judges the acceptance/rejection of the marking, and, if an abnormality occurs, generates a signal to the alarm device 24 to notify the abnormal situation to workers concerned, and generates a command to hold the coil shipment. To the coil which is stopped from shipment, re-inspection or the like is applied.

When the defect marking monitored by the defect marking detection device 9 is judged as normal, the defect information and the defect position are entered to an external memory device 14, and the cutting machine 15 is actuated to cut the steel sheet. Then, the defect information and the defect position are inversely developed, or the position measured from inner periphery of the coil is converted to the position measured from outer periphery thereof, and the data are printed.

Since the coil is cut by the cutting machine 15 for individual buyers, the standard length of coil is based on the cut signal at the cutting machine 15. The document to be submitted to buyer has an expression of inverse development starting from the outer periphery of the coil for convenience of use of the buyer.

Since a distinctive marking is applied to the harmful defect position as described above, in the succeeding step to remove the harmful defect or on applying working at the buyer, presence/absence of harmful defect during coil rewinding is readily judged.

The above-described procedure adopted a visual inspection of a worker to give judgment of harmful defect. However, the visual inspection may be eliminated if only the defect detection accuracy of the surface defect tester 3 is satisfactory. Furthermore, by installing a defect marking detection device in the succeeding stage for the marked coil, more accurate and efficient work for defect removal can be conducted.

The facilities shown in FIGS. 1 through 4 arrange the surface defect tester 3 or further the magnetic particle tester 3, the defect marking device 8 and the defect marking detection device 9 in series on a line. As described before, however, it has already been brought into practical use that the calculation is given to determine the defect position, the defect name, and the defect grade on the basis of the defect information detected by the surface defect tester or further by the internal defect tester on a processing line that is provided with the surface defect tester or further the internal defect tester, and that the information is displayed on a CRT or is printed on a document.

Accordingly, it may be implemented that at least one of the defect marking device and the defect marking detection device is located on a separate line from the line that is provided with a surface defect tester or further an internal defect tester, and that the marking at the defect position and the confirmation of the defect marking are conducted by identifying the harmful defect and the injudicable defect on the separate line that is provided with the surface defect tester or further the internal defect tester, as in the case of facilities of FIGS. 1 through 4, thus printing the result on a document.

In that case, it may be done that the edited and identified harmful defect and injudicable defect information on a processing line provided with a surface defect tester or further an internal defect tester is generated, together with the defect position information, to a centralized control panel on a separate line via an external memory device, and the separate line conducts tracking of the harmful defect and the injudicable defect, then a defect marking device conducts marking, and a defect marking detection device monitors the state of defect marking, and further the monitored result is re-edited by the centralized control panel to generate the edited information to an external memory device. By this procedure, the effect of the present invention is attained with further inexpensive facilities.

Figure 15:
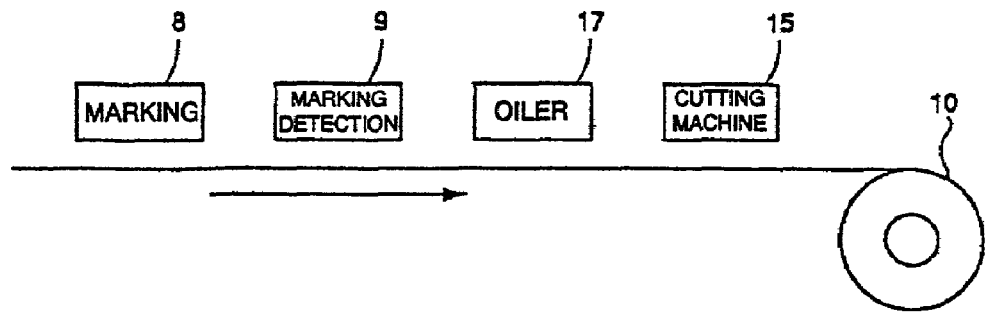
FIG. 15 illustrates an example of arrangement of main facilities of a processing line provided with a defect marking device and a defect marking detection device relating to the Best Mode 1 according to the present invention.
Figure 16:
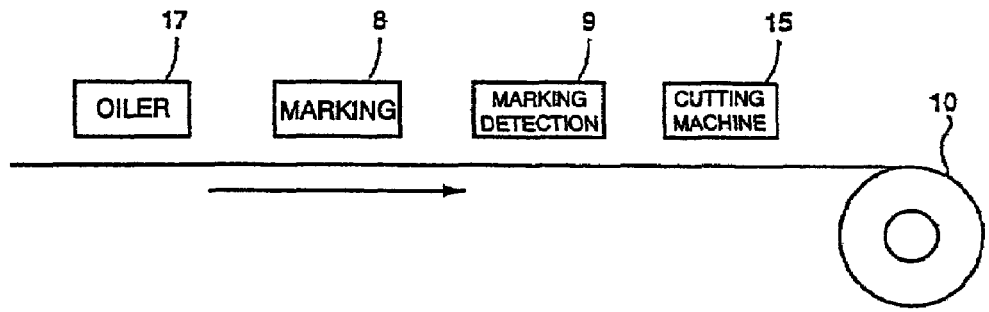
FIG. 16 illustrates an example of arrangement of main facilities of another processing line provided with a defect marking device and a defect marking detection device relating to the Best Mode 1 according to the present invention.
Figure 17:
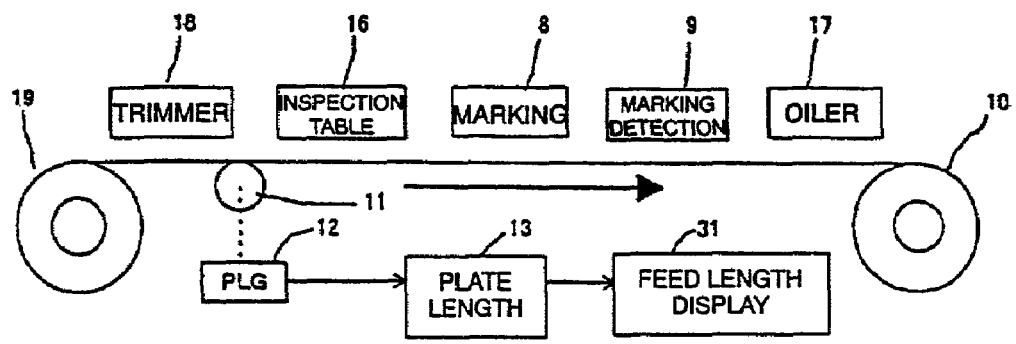
FIG. 17 illustrates an example of arrangement of main facilities of a processing line provided with a defect marking device, a defect marking detection device, further an inspection table and a defect marking detection device, relating to the Best Mode 1 according to the present invention.

FIGS. 15 through 17 show examples of arrangement of main facilities in the separate line in that case. FIG. 15 is the case that an oiler 17 is located at downstream side of the defect marking detection device 9. FIG. 16 is the case that the oiler 17 is located at upstream side of the defect marking device 8. FIG. 17 is the case that a trimmer 18 and an inspection table 16 are located at upstream side of the marking device 8, while locating the defect marking detection device 9 at downstream side thereof. In the case of FIG. 17, the result of visual inspection of the defect on the inspection table may be subjected to secondary correction, at need, as in the case of FIGS. 1 through 4.

Figure 18:
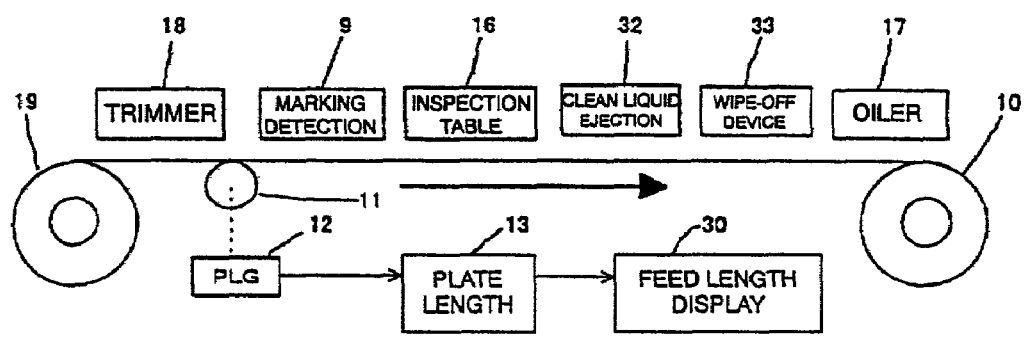
FIG. 18 illustrates an example of arrangement of main facilities of a coiling line provided with a defect marking detection device, relating to the Best Mode 1 according to the present invention.
Figure 19:
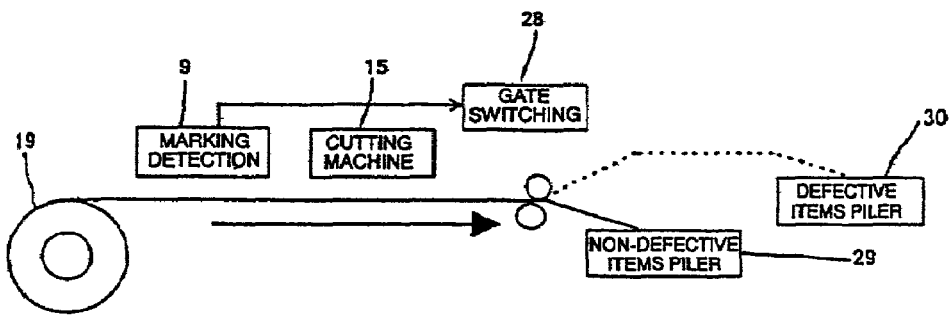
FIG. 19 illustrates an example of arrangement of main facilities of a shear line provided with a defect marking detection device, relating to the Best Mode 1 according to the present invention.

Examples of working with a marked coil are described referring to FIGS. 18 and 19.

FIG. 18 shows a recoil line which is a downstream stage in a continuous line, which recoil line is provided with a cleaning liquid ejection device 32 and a cleaning liquid wipe-off device 33, adding to the defect marking detection device 9. When the defect marking detection device 9 detects a defect marking of an injudicable defect, it generates a line-stop command, and the inspector applies re-judgment to the matter. The inspector classifies harmful defect and harmless defect. If the inspector judges as harmless defect, the cleaning liquid ejection device 32 ejects a weak alkali cleaning liquid to wash off the marking, then the cleaning liquid wipeoff device 33 wipes out the cleaning liquid and the marking ink, then re-applies oil. When the injudicable defect is subjected to re-judgment and when the defect is judged as harmful defect, the cutting machine 15 cuts off the harmful defect portion, and a tension reel 10 winds only the accepted coil.

FIG. 19 shows a shear line. A sheet free from defect marking is sent to a non-defective items piler 29. When the defect marking detection device 9 located at inlet of the sheet line detects a defect marking, it generates a signal to a gate switching device 28. On receiving the signal, the gate switching device 28 switches the gate, and, the sheet having the defect marking portion is sent to a defective items piler 30, where the harmful defect portion and the injudicable defect portion are removed.

Figure 20:
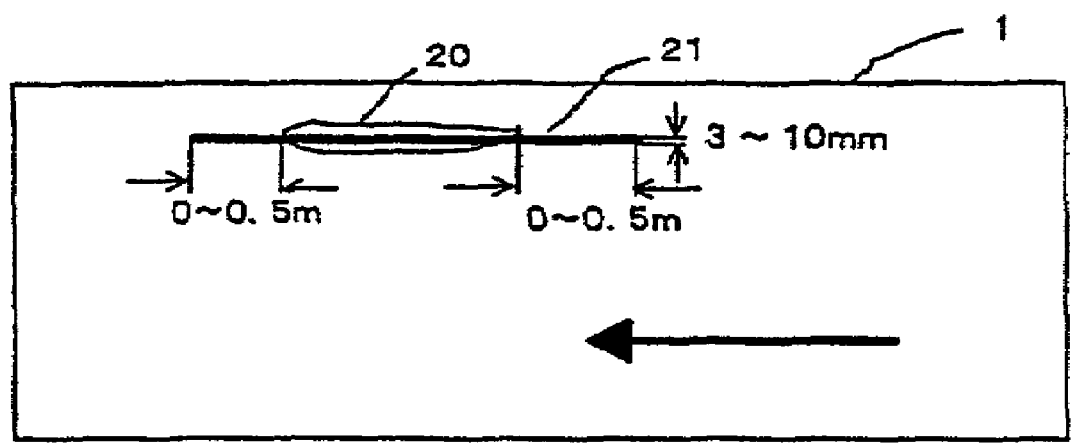
FIG. 20 illustrates an example of applying defect marking on a defect portion, relating to the Best Mode 1 according to the present invention.
Figure 21:
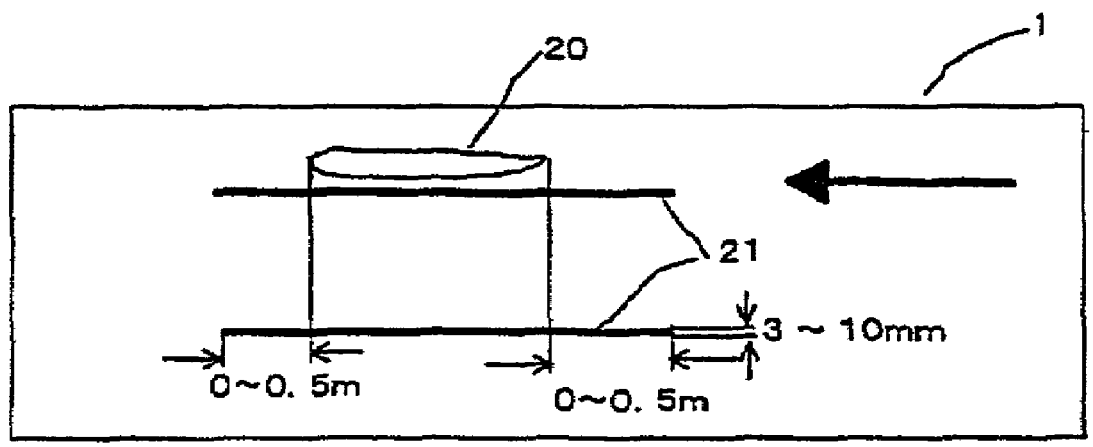
FIG. 21 illustrates an example of applying defect marking at two points on the same position in the width direction of steel sheet, independent of the place of defect portion, relating to the Best Mode 1 according to the present invention.

As for a steel sheet being subjected to press-working, it is preferable to apply a marking method that takes into account of its use. FIGS. 20 and 21 illustrate examples of defect marking in the case that visual inspection is given on a harmful defect portion 20 after pressed. FIG. 20 is the case that defect marking 21 is applied to the defect portion 20. FIG. 21 is the case that the defect marking is applied on each side of steel sheet 1 at the same position in width direction thereof independent of the place of the defect. The position of defect marking may be selected responding to the defect information in the width direction of the steel sheet and to the use thereof.

The description above-given is the case that an ink marker is positioned in the defect marking device 8 to apply marking at the defect position, or that further a coil with defect marking is treated. Instead of the ink marker device, however, an abrasive member marking device that applies marking using an abrasive member may be installed to conduct marking with the abrasive member to the defect position.

With the defect marking device using an abrasive member, a grinder or an abrasive member such as nonwoven fabrics containing abrasives is directly pressed against the steel sheet 1, or a rotating brush roll is pressed against the steel sheet 1, thus applying marking.

For the case of a defect marker device using an abrasive member, the marking response is inferior to some degree to the case of ink marker device. Consequently, the marking length and line width are varied to some extent, or the marking color can not be changed different from the case of ink marking, so that different marking indications are given to individual defect grades. For other features, however, the defect marker device with abrasives is able to give working with a defect marking and a coil with defect marking, similar to the case of ink marker device.

Figure 22:
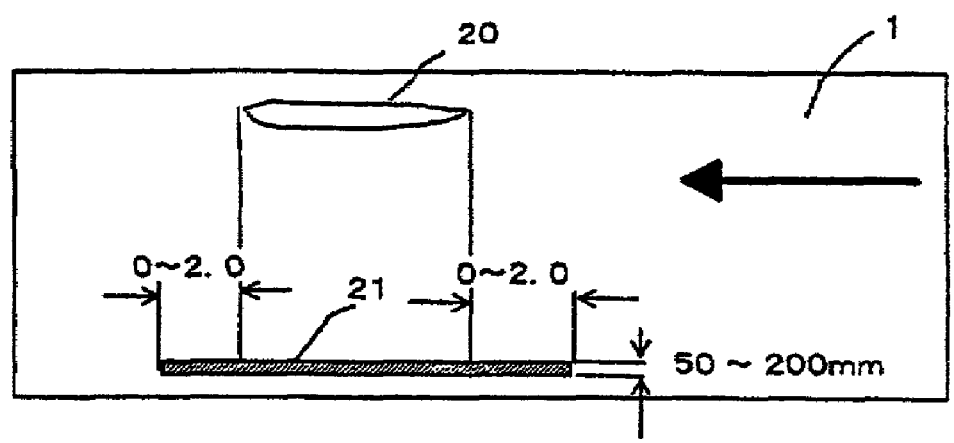
FIG. 22 illustrates the relative state between the defect position and the defect marking position, relating to the Best Mode 1 according to the present invention.

For the case of using abrasive member, the marking length is preferably selected to somewhat longer than the ink marking length considering the tracking accuracy and the response performance. In concrete terms, a command is generated by the centralized control panel 8 to apply marking longer than the identified defect length by 0.5 to 1.0 m to each of front and rear edges of the defect, or totally 1 to 2 m longer than the identified defect length. For a dot-like defect having lengths of several millimeters or less, the command is generated to apply marking by adding 0.25 to 1.0 m to each of front and rear edges of the defect. For the convenience of detection by visual inspection and by the defect marking detection device 9, the marking line width is most preferably in a range of from 50 to 200 mm. FIG. 22 illustrates the state between the defect position and the defect marking position. The harmful defect 20 is within an indication range of the defect marking 21 in the length direction.

When two units of ink marker device are installed, as illustrated in FIG. 14, the ink color is changed responding to the defect grade. In the case of an abrasive member is applied, however, color cannot be changed. Therefore, in the case that two units of abrasive member marker device are installed, similar working with the ink marker device can be conducted by changing the marking line, (for example, a single marking line is applied when the defect harmful to the buyer is distinctive, and double marking line is applied when the defect is injudicable one.)

Figure 23:
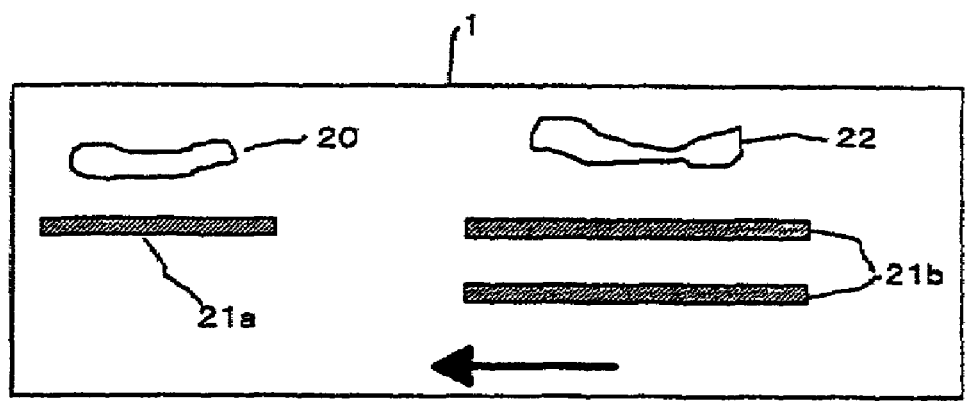
FIG. 23 illustrates an example of applying separate marking for a harmful defect and an injudicable defect using two units of detect marking device, relating to the Best Mode according to the present invention.

FIG. 23 illustrates a state of defect and defect marking position in the case of marking with two units of abrasive member marker device. The figure shows a single defect marking line 21a for the harmful defect 20 and a double defect marking line 21b for the injudicable defect 22.

The defect marking using an abrasive member does not induce problem of dent generation on the surface of steel sheet because no shading problem occurs, which is observed in the paint marking case, and applies sure marking on the surface of the steel sheet even if the coil is applied with oil. In addition, the steel sheet may be applied with oil immediately after marking, and no dryer is necessary, which is needed in the case of ink marking. Thus, simpler facilities are realized.

When the marking is applied using a brush roll as the abrasive member, the brush roll may be located to allow the marking over the whole width of the steel sheet, at need, thus applying marking over the whole width thereof.

As described above, according to the present invention, it is possible to apply defect marking without inducing flaw on the steel sheet and to surely and readily identify the harmful defect independent of presence/absence of oil such as rust-preventive oil on the surface of the steel sheet.

Furthermore, by tracking the defect position on the surface of the steel sheet, then by applying marking to the harmful defect portion, the buyer readily detects the defect portion. In addition, by winding also the harmful defect portion, the shipment can be done with a necessary coil length, which improves the work efficiency of the buyer.

Furthermore, since adequate marking indication is given by changing the marking indication method responding to the degree of defect, and by considering the defect name, the defect degree, and the use of the steel sheet, the effect of improving the work efficiency is further enhanced.

By adopting the ink marker device, the defect marking color is selected responding to the grade of steel sheet and to the surface color of the steel sheet, so that the effect of improvement in work efficiency and the effect of prevention of overlooking defect are further enhanced.

With use of a grinding member marker device, even a coil with applied with oil can be surely marked on the surface thereof. In addition, the steel sheet may be applied with oil immediately after marking, and no dryer is necessary, which is needed in the case of ink marking. Thus, simpler facilities are realized.

Also for the steel sheet manufacturers, the work to remove harmful defect portion becomes easy, and the work efficiency significantly increases. Furthermore, for the injudicable defect, excessive defect removal work is not required, which also improves the work efficiency.

Best Mode 2

The first aspect of the Best Mode 2 is a surface flaw marking device for a metal strip, which surface flaw marking device comprises: a flaw inspection means having plurality of light-receiving parts that identify reflected lights coming from an inspection plane of a metal strip under two or more of optical conditions different from each other, and a signal processing section that judges presence/absence of surface flaw on the inspection plane based on a combination of reflected light components identified under these optical conditions different from each other; and a marking means that applies marking indicating the information about the flaw on the surface of the metal strip.

The device according to the first aspect of the Best Mode 2 receives light reflected from the surface of the metal strip by two or more of light-receiving part, having different optical conditions such as polarization condition to each other, and analyzes the optical properties from the received result. Then, the signal processing section of the flaw inspection means gives judgment on normal part and abnormal part, or judgment on the surface flaw, on the surface of the metal strip based on thus obtained optical properties. For the part judged as the surface flaw, marking is applied using a specified method such as printing, carved stamping, and drilling. The position for marking can be selected by tracking the position of or nearby the surface flaw using a tracking means or the like.

The following is the description about the mode of optical reflection on the surface of steel sheet, which is a target of the inspection by the surface flaw inspection device according to the present invention, relating to microscopic surface irregularity on the surface of the steel sheet. Generally, the microscopic irregularity on the surface of steel sheet, which is originally significantly rough, improves its flatness by strong rolling by a roll during temper rolling (tempering), while other portions leave their irregular shape because the roll of the temper rolling does not contact thereto.

Figure 35:
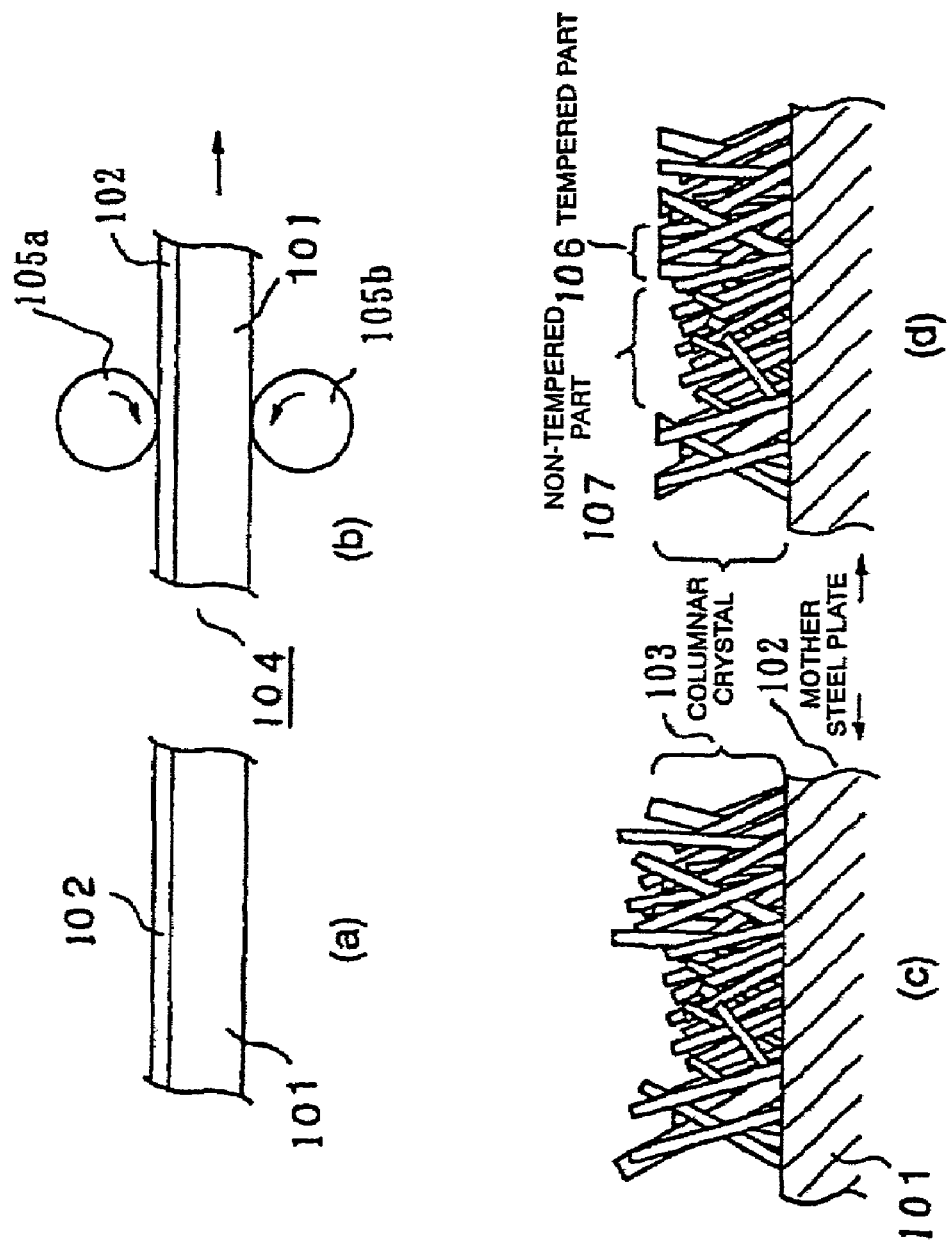
FIG. 35($a$) through ($d$) illustrate the method for manufacturing alloyed zinc plated steel sheet and show detail cross sectional views of the sheet, relating to the Best Mode 2 according to the present invention.

For example, in the case of alloyed galvanized steel sheet, the cold-rolled steel sheet 101, the mother material, is subjected to hot dip galvanizing as shown in FIG. 35(*a*), then passes through an alloying furnace. During the passage, the iron element of the mother material steel sheet diffuses into the zinc of the plating layer to generally form columnar alloy crystals 103 as shown in FIG. 35(*c*). When the steel sheet is subjected to temper rolling as shown in FIG. 35(*b*), the particularly projected portions of the columnar crystals 103 are collapsed in flat shape, (tempered part 106), as shown in FIG. 35(*d*), while leaving other portions (non-tempered part 107) as in the columnar crystal shape.

Figure 36:
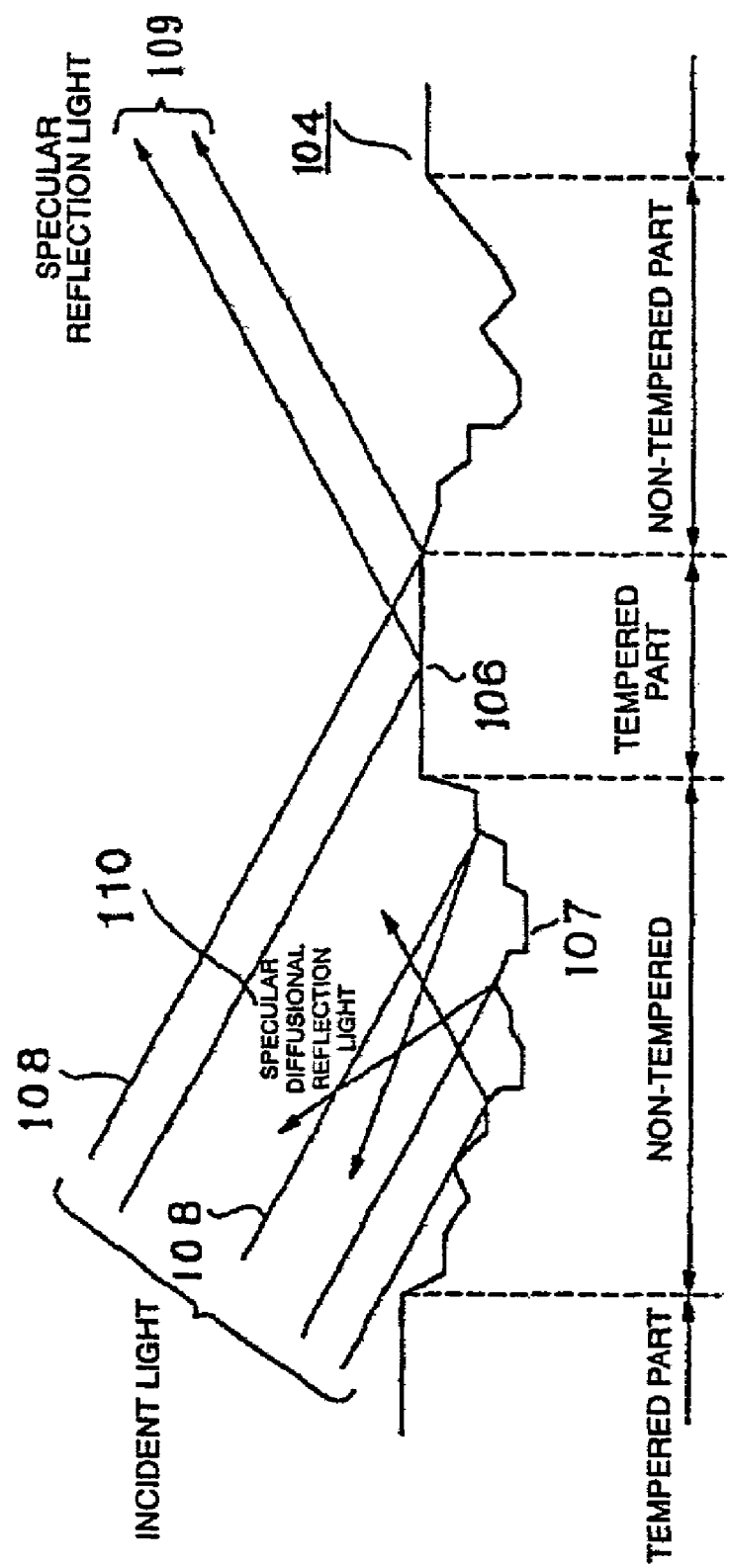
FIG. 36 shows a schematic cross sectional view of the tempered part and the non-tempered part on the surface of metal strip after temper-rolling, illustrating the relation between the incident light and the reflection light, relating to the Best Mode 2 according to the present invention.

FIG. 36 is a model illustrating what kinds of optical reflections occur on that type of steel sheet surface. The incident light 108 coming into the portion collapsed by temper rolling, (tempered part 106), gives specular reflection to the direction of regular reflection to the steel sheet. On the other hand, the reflection direction of the incident light coming into the portion which leaves original columnar crystals not collapsed by the temper rolling, (non-tempered part 107), does not necessarily coincide with the regular reflection direction to the steel sheet, though it is reflected in specular manner on individual micro-area elements on the columnar crystal surface in microscopic view.

Figure 37:
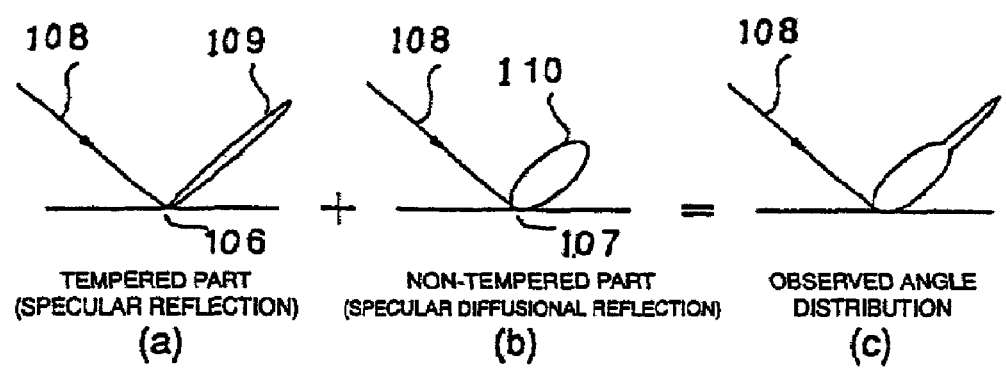
FIG. 37($a$) through ($c$) show angle distribution of reflected light at the tempered part and the non-tempered part, relating to the Best Mode 2 according to the present invention.

Therefore, the distribution of reflection light angles at tempered part and non-tempered part becomes to FIG. 37(*a*) and FIG. 37(*b*) in macroscopic view, respectively. That is, (a) at the tempered part 106, a specular reflection 109 having a sharp distribution in the regular reflection direction to the steel sheet occurs, and (b) at the non-tempered part, a reflection 110 having a broad range responding to the angle distribution on micro-area elements on the surface of columnar crystals appears. Hereinafter the former is referred to as the specular reflection, and the latter is referred to as the specular-diffuse reflection. The actually observed distribution of reflection angles is the sum of the angle distribution of specular reflection and the angle distribution of specular-diffuse reflection responding to each area percentage of the tempered part and the non-tempered part, as shown in FIG. 37(*c*).

The above-given description deals with an alloyed galvanized steel sheet. However, the description is generally applicable to other steel sheets generating flat portions by temper rolling.

Figure 38:
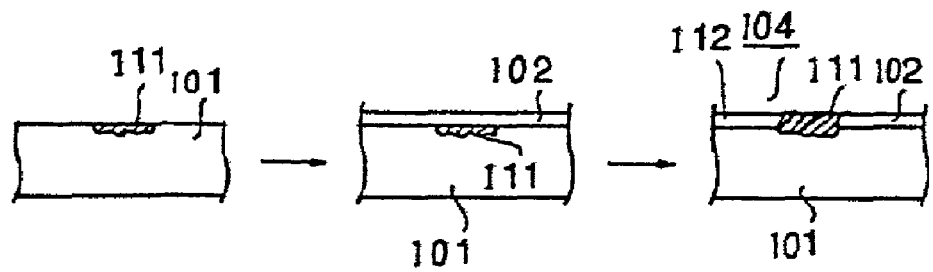
FIG. 38 shows cross sectional views of an alloy zinc plated steel sheet to illustrate the progress of occurrence of scab, relating to the Best Mode 2 according to the present invention.

The following is the description about the optical reflection characteristics of flaw called the pattern-like scab, and which has no significant surface irregularity, which is a target of the present invention. For example, as seen in FIG. 38, a scab 111 appeared on an alloyed hot dip galvanized steel sheet 104 exists in an original plate 101 of cold-rolled steel sheet before plating, on which a plating layer 102 is applied, and further the alloying proceeds by diffusion of the iron in the mother material.

Compared with mother material, the scabbed portion generally differs in plating thickness and in degree of alloying. As a result, for example, in the case that the plating layer thickness at the scabbed portion becomes thick and that the scab is convex against the mother material, the temper rolling increases the area of tempered part than that of non-tempered part. Inversely, if the scabbed portion is concave against the mother material, the scabbed portion does not touch the temper rolling roll, and the non-tempered part occupies large portions. If the alloying at scabbed portion is shallow, the angle distribution of micro-area elements is enhanced in the normal direction to the steel sheet, and the diffusion performance becomes weak.

Figure 40:
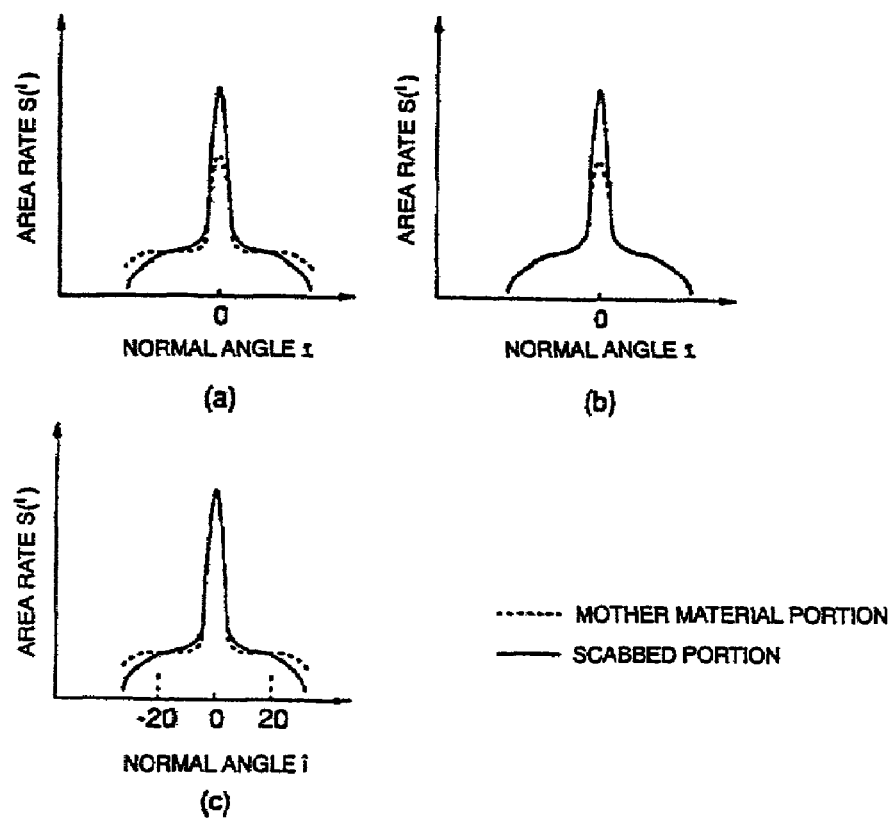
FIG. 40($a$) through ($c$) show the relation between the normal angle to micro-area element and the area percentage, at scabbed portion and mother material on the inspection plane, relating to the Best Mode 2 according to the present invention.

The following is the description about the appearance of pattern-like scabs depending on the difference in surface property of the scabbed portion and of the mother material. When the difference between the scabbed portion and the mother material is classified depending on the above-described modified model of plating surface during temper rolling, three kinds of groups appear as shown in FIG. 40.

(a) In a scabbed portion (solid line), the area percentage of the tempered part and the angle distribution on micro-area elements in the non-tempered part differ from those in the mother material (broken line). The tempered part corresponds to the normal angle $\xi=0$, indicating the peak in the figure. The peak height (area percentage) differs in the scabbed portion and the mother material. The non-tempered part corresponds to the other parts (slope), and, in the figure, the distribution of the area percentage differs in the scabbed portion and the mother material. The slope part reflects the angle distribution on micro-area elements in the non-tempered part.

(b) Although the area percentage of the tempered part differs between the scabbed portion and the mother material, the angle distribution on micro-area elements in the non-tempered elements does not differ from each other. The figure shows different peak height in scabbed portion and in mother material. However, the slope shape agrees to each other.

(c) Although the angle distribution on micro-area elements in the non-tempered part differs between the scabbed portion and the mother material, the area percentage in the tempered part does not differ to each other. The figure shows different peak height in scabbed portion and in mother material. However, the slope shape differs from each other.

That difference in the area percentage of the tempered part and in the angle distribution on micro-area elements is observed as the difference in the angle distribution of reflected light quantity, as shown in FIG. 39.

If the area percentage of the tempered part shows a difference, (as in the case of above-described (a) and (b)), the angle distribution of the reflected light quantity becomes that on the scabbed portion 111a and on the mother material 112a, as shown in FIGS. 39(a) and (b). The difference is observed in the direction that the angle distribution becomes a peak, or the direction of regular reflection. If the area percentage of the tempered part in the scabbed portion is larger than that in the mother material, (FIGS. 39(a) and (b), and FIGS. 40(a) and (b)), the scab is seen bright from the regular reflection direction. And, if the tempered percentage in the scabbed portion is less than that in the mother material, the scab is seen dark from the regular reflection direction.

If there is no difference in the area percentage of the tempered part, (in the case of above-described (c)), the observation from the normal reflection direction to the steel sheet cannot see the scab. Nevertheless, if there is a difference in the diffusion property of the components of specular-diffuse reflection, the flaw can be seen from the diffusional direction at an off-peak angle distribution, as shown in FIG. 39(c). For example, when the diffusional property of the components of specular-diffuse reflection is small, generally the scab is viewed bright from a diffusional direction relatively near to the regular reflection, and the brightness gradually becomes weak with off-setting from the regular reflection direction, and finally, the difference between the scabbed portion and the mother material becomes none at a certain angle, thus the observation at around this angle is no more possible. Further off-setting from the regular reflection angle allows the observation of scab in dark color.

To identify and detect that pattern-like scab from the mother material, it is necessary to investigate the angle of micro-area elements for identifying the reflection light. For example, as in the case of FIGS. 39(a) and (b), the detection of difference between the scabbed portion and the mother material in the regular reflection direction means the determination of the ξ=0 angle distribution among the angle distribution in micro-area elements, shown in FIG. 40, thus detecting the difference between the scabbed portion and the mother material.

Figure 41:
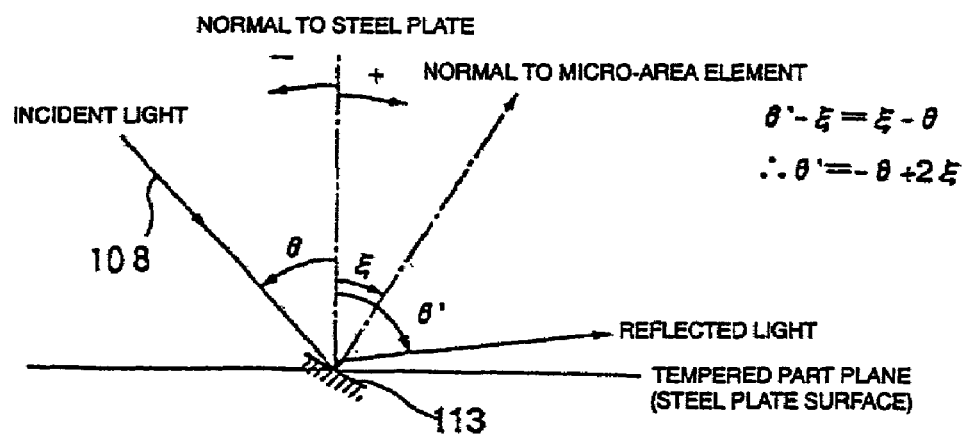
FIG. 41 shows the relation between angles of the incident light, the reflection light, and the like, on a micro-area element on the inspection plane, relating to the Best Mode 2 according to the present invention.

When the identification at ξ=0 angle distribution is described in terms of arithmetic expression, a function S(ξ) shown in FIG. 40 is multiplied with a function that signifies an identification characteristic expressed by a delta function δ(ξ) shown in FIG. 42(a), (hereinafter referred to simply as "weight function"), then the product is integrated. Furthermore, for example, at an incident light angle of 60 degrees, the observation at 40 degrees, or offsetting by 20 degrees, means that the reflection on a plane (micro-area element) offsets by 10 degrees of normal angle ξ. This corresponds to the use of a weight function of δ(ξ+10), as seen in FIG. 42(b). The relation between the reflection angle and the normal angle ξ to a micro-area element is calculated from FIG. 41.

According to the consideration, the identification of reflected light from an angle of micro-area element corresponds to the design of a weight function. The weight function is not necessarily a delta function, and it may have a certain width.

Figure 42:
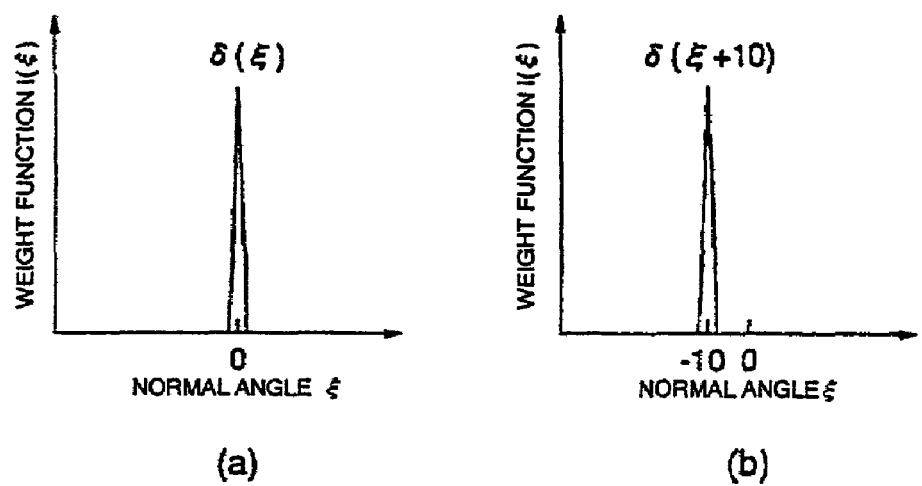
FIGS. 42(*a*) and (*b*) show the relation between the normal angle to a micro-area element and the weight function, relating to the Best Mode 2 according to the present invention.

Based on the concept, when the scabs having respective area percentages expressed by FIGS. 40(a), (b), and (c) are identified separately from the mother material, and when a weight function for the detection is considered, the δ function δ (ξ) given in FIG. 42 is also an example thereof. This, however, cannot bring the size of visible area of the two optical systems the same because the cameras are installed at different receiving angles, respectively. If the cameras are installed for measuring a diffuse reflection light, the change in the weight function is not easy because the camera positions have to be changed.

For the former issue, measurement on the same optical axis is required. And, it is preferred that both components of the specular reflection and of the specular-diffuse reflection are grasped by the measurement in the direction of regular reflection on the steel sheet, not grasping the diffuse reflection light. For the latter issue, it is preferred that the weight function can be set with some degree of freedom against the changes in the camera position.

According to the object, the present invention adopts a linear light source having a diffusional characteristic, not a parallel light source such as that of laser light. Furthermore, the specular reflection component and the specular-diffuse reflection component are separated and identified from the regular reflection direction to the steel sheet using polarized light.

Figure 43:
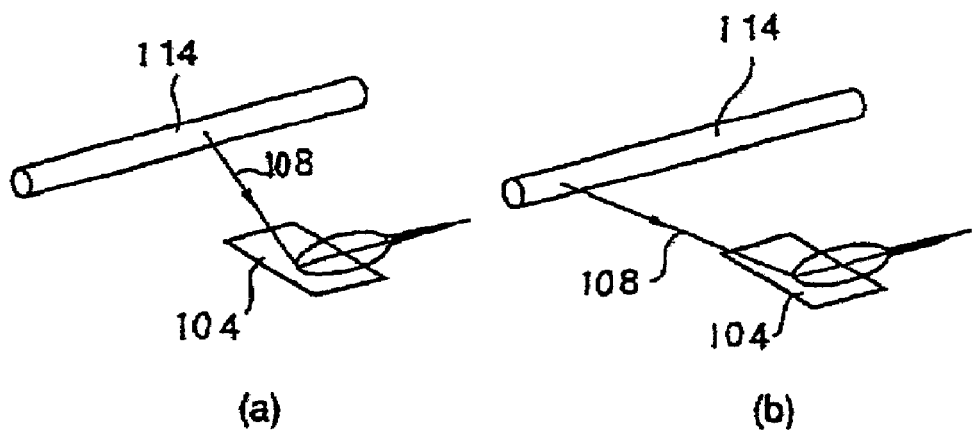
FIGS. 43(*a*) and (*b*) show the relation between individual incident lights emitted from various positions on the linear diffusion light source and the responding incident positions on the inspection plane, relating to the Best Mode 2 according to the present invention.

To explain the action and the effect of the linear diffusional light source, a linear diffusional light source 114 is placed in parallel with a steel sheet 104, as shown in FIG. 43, and the reflection characteristic is investigated by observing a point which is in a plane vertical to the light source and which is on the steel sheet 104 from the direction that the incident angle coincides with the outgoing angle, (hereinafter referred to as the "regular reflection direction to the steel sheet").

As shown in FIG. 43(a), when the light is emitted from center part of the linear light source 114, the light entered the tempered part is reflected in a specular mode, all of which is caught in the regular reflection direction to the steel sheet. On the other hand, the light entered the non-tempered part is reflected in a specular diffusional mode, of which only the light reflected from micro-area elements that face the same direction with that of the normal to steel sheet can be detected. Since the number of those micro-area elements is very few in probability, the reflected light that is detected in the regular reflection direction to the steel sheet is occupied mainly by the specular reflection from the tempered part.

To the contrary, when the light is emitted from a part other than the center part of the linear light source, as shown in FIG. 43(b), the light entered the tempered part is reflected to a direction other than the regular reflection direction to the steel sheet by specular reflection, thus the light cannot be detected in the regular reflection direction to the steel sheet. On the other hand, the light entered the non-tempered part is reflected in specular-diffuse reflection mode, of which the light reflected in regular reflection direction to the steel sheet can be detected. Consequently, all the reflected light that can be detected in regular reflection direction to the steel sheet is the light of specular-diffuse reflection on the non-tempered part.

Both of the above-described cases lead a conclusion that, for the light emitted from the whole area of a linear light source, the detective light under observation from regular reflection direction to the steel sheet is the sum of the specular reflection light on the tempered part and the specular-diffuse reflection light on the non-tempered part.

The following is the description about the variations in polarized light characteristics on observation on an inspection plane from the regular reflection direction using that type of linear light source.

Generally, for the reflection on a specular metal surface, particularly to a light having the direction of electric field in parallel with the incident plane, (or p-polarized light), or to a light normal to the incident plane, (or s-polarized light), the polarized light characteristics are maintained after the reflection, thus the p-polarized light outgoes as the p-polarized mode, and the s-polarized light outgoes as the s-polarized mode. An arbitrary linear polarized light that has p-polarized component and s-polarized component at a time outgoes as an elliptically polarized light responding to the reflectance ratio and the phase difference of p- and s-polarized lights.

Figure 44:
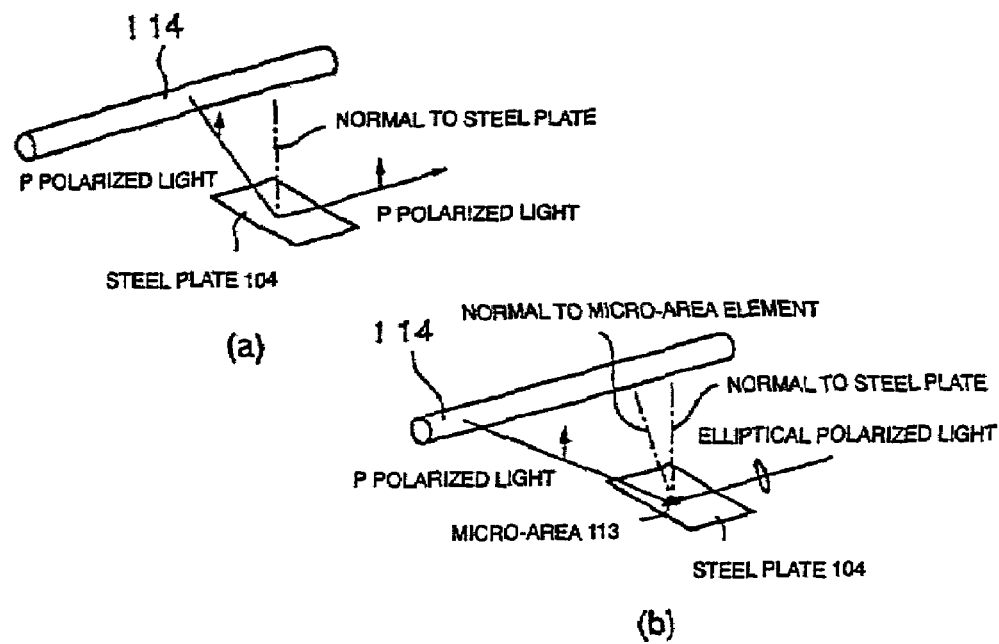
FIGS. 44(*a*) and (*b*) shows the polarized state of reflection light coming from a micro-area element in the case that each incident light coming from the linear diffusion light source is polarized, relating to the Best Mode 2 according to the present invention.

The following discusses the case that a light is emitted from a linear diffusional light source onto an alloyed galvanized steel sheet. As shown in FIG. 44(a), the light emitted from center part of the linear light source 114 is specularly reflected at the tempered part of the steel sheet 104 and is observed in the regular reflection direction to the steel sheet. In this case, the ordinary reflection on a specular metal surface is established, thus the p-polarized light outgoes as the p-polarized mode.

On the other hand, the light emitted from a part other than the center part of the linear light source is specularly reflected on micro-area elements that are inclined on the crystal surface on the non-tempered part, as shown in FIG. 44(b), thus, some of the reflected light can be observed in the regular reflection direction to the steel sheet. In this case, even when a p-polarized light parallel with the incident plane of the steel sheet is entered, the light becomes a linear polarized light having both p- and s-polarized light components because the incident light is not in parallel with the incident plane for the micro-area elements which are inclined from which the light is actually reflected. As a result, the incident light outgoes from micro-area elements as an elliptical polarized light. The same result appears when an s-polarized light is entered instead of p-polarized light.

As for a linear polarized light with an arbitrary polarization angle, having both p- and s-polarized light components, the same reason as above-described can be applied, or, since the polarization angle becomes inclination from the incident plane, the shape of elliptical polarized light that is emitted in the regular reflection direction to the steel sheet differs from that of the light that entered from the center part of the linear light source and is reflected from the tempered part.

For the case of emitting linear polarized light having both p- and s-polarized light components, more detail explanation is given below.

Figure 45:
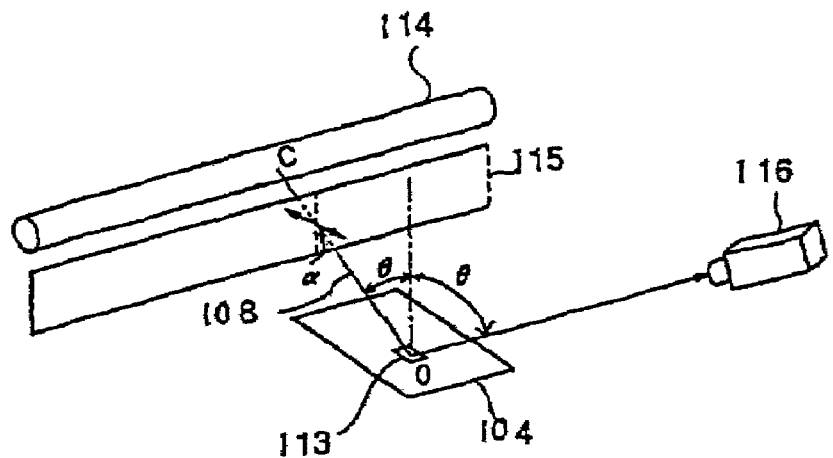
FIG. 45 illustrates the reflection light coming from a micro-area element in the case that the incident light coming from center part of the linear diffusion light source is polarized, relating to the Best Mode 2 according to the present invention.

As shown in FIG. 45, a light 108 coming from the linear diffusional light source 114 is converted to a linear polarized light by a sheet polarizer 115 having an azimuth α, which is then entered the steel sheet 104 positioned in horizontal direction. The regular reflection light is received by a light detector 116.

As described before, for the light 108 emitted from a point C on the light source, both the component specularly reflected from the tempered part and the component reflected in specular-diffuse reflection mode from micro-area elements that, by chance, the normal thereof directs to the vertical direction in the non-tempered part contribute to the light reflected from the point O (and from a region 113 peripheral to the point O) on the steel sheet to the direction of the light detector 116.

To the contrary, as for the light 108 emitted from the point A which is offset by an angle φ viewed from the point O, the specularly reflected light component is reflected in a direction different from that of the light detector 116, thus only the component of specular-diffuse reflection on micro-area elements with a normal angle ξ (the angle of normal to the vertical direction is ξ) contributes. The relation between φ and ξ is given by the equation below under a simple geometrical consideration.

$$\cos\xi = 2\cos\theta\cos^2(\phi/2) / [\sin^2\phi + 4\{\cos^2\theta\cos^4(\phi/2) + \sin^2\theta\sin^4(\phi/2)\}]^{1/2} \quad (1)$$

Where, θ designates the incident angle to the steel sheet.

The state of polarized light of the light reflected in that manner is considered in the following. Referring to FIG. 45, the light 108 which is emitted from the point C passes through the sheet polarizer 115 having an azimuth α, then is reflected at the point O on the steel sheet. The polarized light state at that moment is expressed by Jones matrix which is generally used in the polarization optics.

$$E\ c = T \cdot E\ \text{in} \quad (2)$$

where, E in designates the linear polarized light vector (column vector) at an azimuth α, and T designates the reflection characteristic matrix of the steel sheet. The component for each of them is written as follows.

$$E\ \text{in} = Ep \cdot {}^t(\cos\alpha, \sin\alpha)$$

$$T = r_s(T_{mn});\ T_{11} = \tan\psi \cdot \exp(j\Delta),\ T_{22} = 1,\ T_{12} = T_{21} = 0$$

where, $^t()$ designates the column vector, tan ψ designates the amplitude reflectance ratio of p- and s-polarized lights, Δ designates the phase difference occurred from the reflectance of p- and s-polarized lights, and $r_s$ designates the s-polarized light reflectance. The matrix expression of them becomes the formula 1.

$$E\ \text{in} = Ep \begin{bmatrix} \cos\alpha \\ \sin\alpha \end{bmatrix} \qquad \text{Formula 1}$$

$$T = r_s \begin{bmatrix} \tan\Psi \cdot \exp(j\Delta) & 1 \\ 1 & 0 \end{bmatrix}$$

Figure 46:
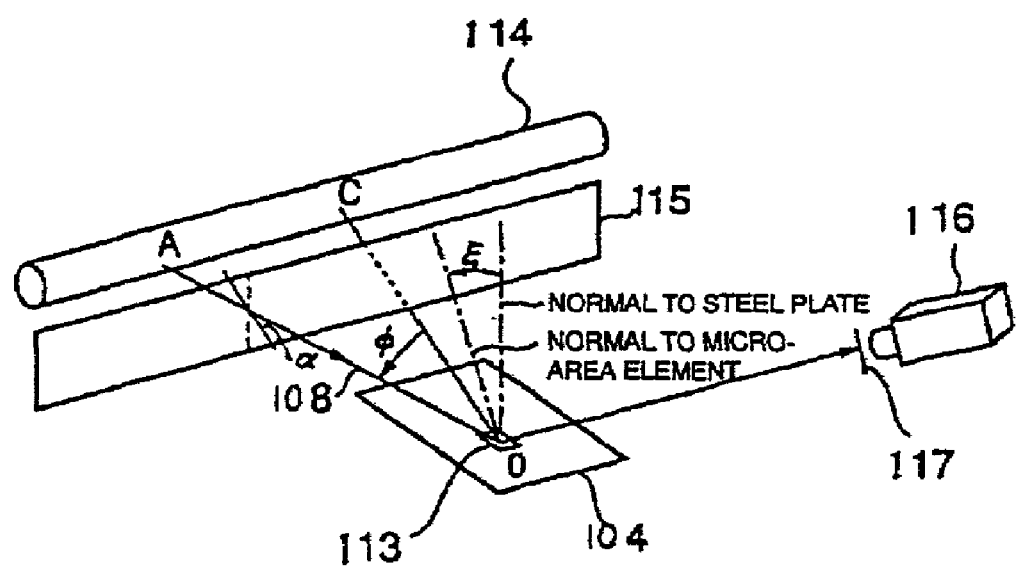
FIG. 46 illustrates the reflection light coming from a micro-area element in the case that the incident light coming from a part other than the center part of the linear diffusion light source is polarized, relating to the Best Mode 2 according to the present invention.

In a similar manner, referring to FIG. 46, the polarized state of light 108 emitted from the point A and reflected on micro-area elements having normal angle ξ to the direction of light detector 116 is expressed by eq. (3) under an assumption that the incident plane crosses orthogonally with the sheet polarizer 115 and an analyzer 117.

$$E\ A = R(\xi) \cdot T \cdot R(-\xi) \cdot E\ \text{in} \quad (3)$$

where, R designates the two-dimensional rotary matrix, and the component $R_{mn}$ is expressed by:

$$R_{11} = R_{22} = \cos\xi,\ R_{12} = R_{21} = -\sin\xi$$

The matrix expression of R(ξ) becomes the formula 2.

$$R(\xi) = \begin{bmatrix} \cos\xi & -\sin\xi \\ \sin\xi & \cos\xi \end{bmatrix} \quad \text{Formula 2}$$

Eq. (2) is a particular case of eq. (3) substituting ξ=0. Thus, both the specular reflection component and the specular-diffuse reflection component can be integrally treated by eq. (3).

Figure 47:
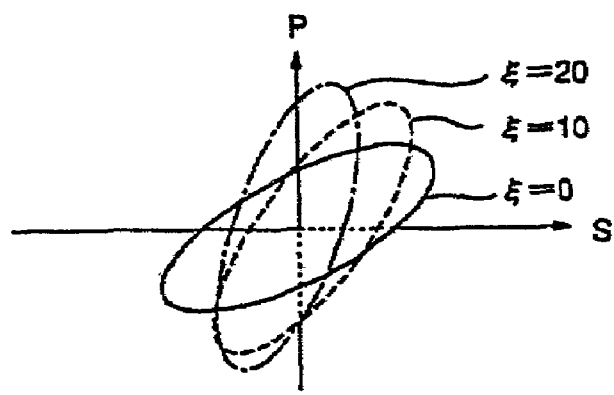
FIG. 47 illustrates the relation between the normal angle to micro-area element and the elliptic polarized light of the reflected light, relating to the Best Mode 2 according to the present invention.

When eq. (3) is calculated to draw a figure of elliptical polarized light state for the light reflected from micro-area elements having a normal angle ξ, FIG. 47 is obtained. The azimuth α of the incident polarized light was assumed to 45 degrees, the incident angle θ was assumed to 60 degrees, and the reflection characteristics of steel sheet were assumed as ψ=28° and Δ=120°. The figure suggests that the ellipse inclines with variations in ξ value against the ellipse at ξ=0, or against the case of specular reflection. Consequently, for example, by inserting an analyzer before the light detector to set the analyzing angle, selection becomes possible to determine the main reflected light coming from particular micro-area elements with a particular normal angle.

To quantify the above-described procedure, the state of polarized light $E_D$, which is obtained by inserting an analyzer having an analyzing angle β into a reflected light in a polarized state, is expressed by eq. (3).

$$E_D = R(\beta) \cdot A \cdot R(-\beta) \cdot E_A$$
$$= R(\beta) \cdot A \cdot R(-\beta) \cdot R(\xi) \cdot T \cdot R(-\xi) \cdot E \text{ in} \quad (4)$$

where, $A=(A_{mn})$ designates the matrix expressing the analyzer, and $A_{11}=1$, while other components are 0. The matrix expression of A becomes the formula 3.

$$A = \begin{bmatrix} 1 & 0 \\ 0 & 0 \end{bmatrix} \quad \text{Formula 3}$$

When the light intensity L of the reflected light on the micro-area elements having a normal angle ξ, detected by the light detector 116 (FIG. 46) is calculated by eq. (4), the light intensity L is expressed by eq. (5) with an assumption of the area percentage of the micro-area element of S(ξ).

$$L = S(\xi) \cdot |E_D|^2 = r_s^2 \cdot Ep^2 \cdot S(\xi) \cdot I(\xi, \beta)$$

$I(\xi, \beta) = \tan^2\psi \cdot \cos^2(\xi-\alpha) \cdot \cos^2(\xi-\beta) + 2 \cdot \tan\psi \cdot \cos\Delta \cdot \cos(\xi-\alpha) \cdot \sin(\xi-\alpha) \cdot \cos(\xi-\beta) \cdot \sin(\xi-\beta) + \sin^2(\xi-\alpha) \cdot \sin^2(\beta-\xi)$ (5)

where, I(ξ, β) is, as described before, the weight function that determines the degree of identification of reflected light on the micro-area elements having a normal angle ξ, which weight function depends on the polarization characteristics of optical system and of inspection body. The product of the weight function and the reflectance of steel sheet, $r_s^2$, the incident light quantity $Ep^2$, and the area rate S(ξ) is the light intensity that can be detected. In the case of a surface-treated steel sheet, or a homogeneous material on the surface of steel sheet, the value of $r_s^2$ should be constant. In addition, the value of $Ep^2$ may also be constant if the incident light quantity is uniform at all positions of light source. Accordingly, to determine the light intensity that is detected by the light detector, only variables to be considered are the area percentage S(ξ) of micro-area elements having a normal angle ξ and the identification characteristic I(ξ, β).

Regarding the identification characteristic I(ξ, β), when an analyzing angle $\beta_0$ that makes the contribution of the micro-area elements having a normal angle $\xi_0$ maximum is selected, the candidates can be given by solving eq. (6) in terms of β.

$$[\partial I(\xi, \beta)/\partial \xi]_{\xi=\xi_0} = 0 \quad (6)$$

The general arithmetic expression of eq. (4) is given by the formula 4.

$$\left[\frac{\partial I(\xi, \beta)}{\partial \xi}\right]_{\xi=\xi_0} = 0 \quad \text{Formula 4}$$

Figure 48:
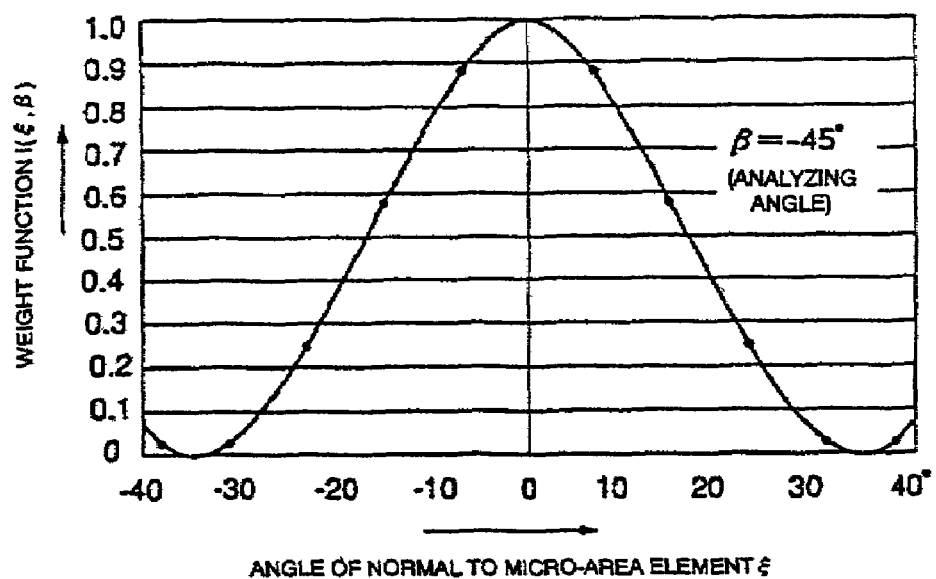
FIG. 48 shows the relation between the normal angle to micro-area element and the weight function, relating to the Best Mode 2 according to the present invention.

When the analyzing angle that gives ξ=0, or that gives maximum contribution of the specular reflection component is determined by eq. (6), the value of β becomes around −45 degrees. Also in this case, the reflection characteristics of the steel sheet adopted ψ=28° and Δ=120°, and the azimuth of polarized light α was 45°. FIG. 48 shows the relation between the normal angle ξ to the vertical direction of micro-area element and the identification characteristic, or the weight function I(ξ,−45), in the case that the analyzing angle β is −45 degrees. For convenience of visibility, the maximum value is standardized to 1.

Figure 49:
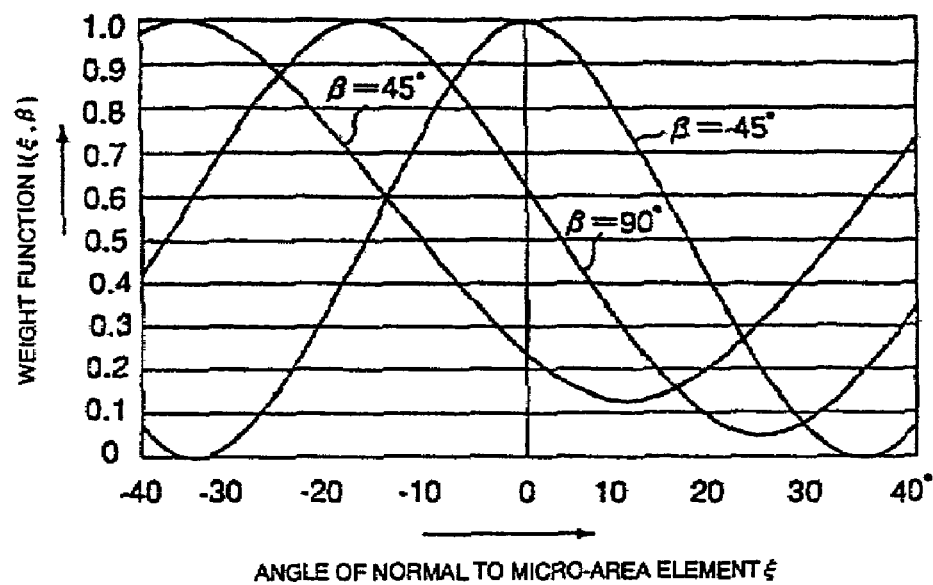
FIG. 49 shows the relation between the normal angle to micro-area element and the weight function at various analyzing angles, relating to the Best Mode 2 according to the present invention.

FIG. 48 shows that the ξ=0, or the specular reflection component, is the governing angle (easy for identification), and that the specular-diffuse reflection light on micro-area elements around normal angles of ξ=±35 degrees is most difficult to be identified. Inversely, an analyzing angle β that the reflection light at ξ=±35 degrees is identified best is determined from eqs. (5) and (6), and the value of β becomes around 45 degrees. FIG. 49 shows the relation between the normal angle ξ against the analyzing angle ξ=45 degrees and the identification characteristic I(ξ, 45). The curve of ξ=45 degrees is not symmetrical in right and left sides. This is a result of that, in view of incident light plane (flat plane formed by the incident light and the reflected light relating to the micro-area element), a positive value of ξ gives apparently less azimuth α of the incident polarized light, (or becomes close to p-polarized light), and that the reflectance of p-polarized light on the steel sheet is less than the reflectance of s-polarized light. FIG. 49 also shows the case of β=90° which gives an intermediate characteristic between β=−45° and 45°.

Figure 50:
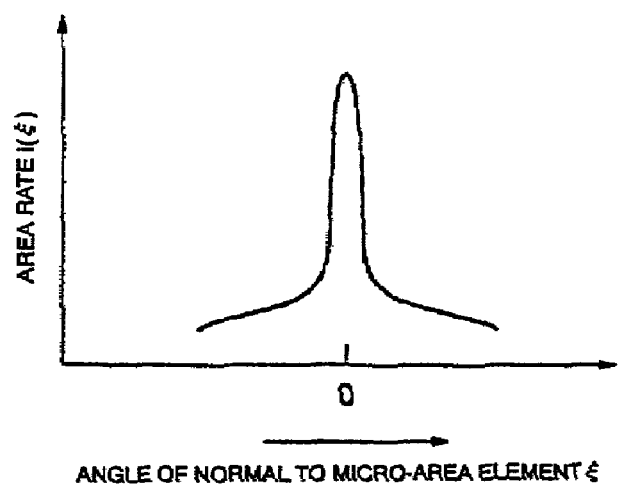
FIG. 50 shows the relation between the normal angle to micro-area element on the inspection plane and the area percentage, relating to the Best Mode 2 according to the present invention.

As given in eq. (5), the reflected light intensity L on a micro-area element having a normal angle ξ is given by a product of the identification characteristics (weight function) I(ξ, β) and the area percentage S(ξ). Accordingly, the intensity of the light received by the light detector 116 is the integrated value of S(ξ)I(ξ, β) in terms of ξ. For example, when a reflected light on a steel sheet having the reflection characteristics shown in FIG. 50 is received through an analyzer having an analyzing angle of β=−45 degrees, the quantity of received light is the integration of the area percentage S(ξ) shown in FIG. 50 with a weight of identification characteristics I(ξ, β) shown in FIG. 48.

If a pattern-like scab having characteristics shown in FIG. 39 exists, the area percentage S(ξ) becomes respective FIGS. 40(*a*), (*b*), and (*c*).

For the case that only the specular reflection component is different as shown in FIG. 39(*b*) and FIG. 40(*b*), the light intensity on receiving that type of flaw through an analyzer having an analyzing angle β=−45 degrees corresponds to the result of integration of FIG. 40(*b*) multiplied by a weight function I(ξ, β) expressed by FIG. 48. Therefore, the difference in the reflected light quantity between the mother material and the scabbed portion can be detected. Regarding the analyzing angle β=45 degrees, there is no difference in the specular-diffuse reflection component, as shown in FIG. 40(*b*), and the difference appears only at nearby ξ=0°. Therefore, considering that the weight function I(ξ, β) at β=45° given in FIG. 49 is a low value at around β=0°, the product becomes a low value over the whole range of ξ, and the difference is cancelled by integration. As a result, no difference between the mother material and the scabbed part can be detected.

In the case that the difference appears only the specular-diffuse reflection component, as shown in FIG. 39(*c*) and FIG. 40(*c*), the detection cannot be attained by passing through an analyzer of −45 degrees. In that case, the detection can be done by passing through an analyzer of 45 degrees that provides high value of weight function I(ξ, β) distant from β=0°.

The normal angles giving no difference in the specular-diffuse reflection component between the mother material and the scabbed portion is around ξ=±20 degrees in FIG. 40(*c*). If, however, there is a flaw that gives normal angle ξ nearby±30 degrees, the flaw cannot be detected even through an analyzer of 45 degrees. In that case, a separate analyzing angle (for example, ξ=90°) providing different identification characteristic is prepared, and the light is received by the third light detector.

Figure 33:
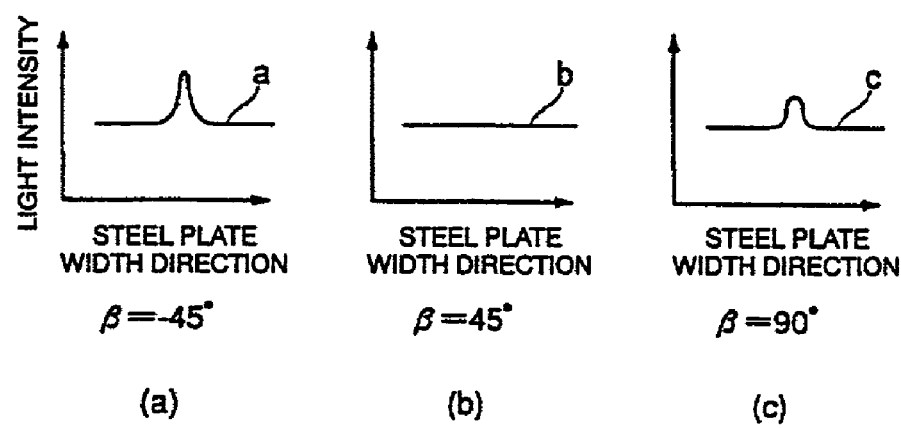
FIG. 33($a$) through ($c$) illustrate examples of light intensity signals observed by a device relating to the Best Mode 2 according to the present invention.

Generally, in most cases, the reflection characteristic of the mother material and scabbed portion on the surface of steel sheet falls in either one of FIGS. 33(*a*), (*b*), and (*c*). Accordingly, detection can be done in most cases by applying either two of the optical conditions (in this example, the analyzing angle). In a special case as described above, however, to prevent overlooking, it is preferable to use three analyzers each having different analyzing angle from each other and to receive the light by identifying the reflected light on micro-area elements having respective three normal angles.

When there is a difference in both the specular reflection component and the specular-diffuse reflection component, as in the case of FIG. 39(*a*) and FIG. 40(*a*), basically the difference between the mother material and the scabbed portion can be detected only from the reflected light passed through a single analyzer.

According to the present invention, an incident sheet polarizer is located covering the whole area of a linear diffusional light source, and the azimuth of the polarized light includes both the p-polarized light and the s-polarized light. Furthermore, there adopt a camera to take image via a polarizer having a polarizing angle further penetrating the specular reflection component in the regular reflection light, and a camera to take image via a polarizer having a polarizing angle further penetrating the specular-diffuse reflection component. This type of optical system conducts observation along a common light axis in the regular reflection direction, so that two kinds of signal are available corresponding to respective specular reflection and specular-diffuse reflection without being influenced by the variations of distance of steel sheet and by the variations of speed. Thus, a surface flaw inspection device that can detect pattern-like scab having no significant surface irregularity is realized. The detection range of angles for specular-diffuse reflection component is readily changed by determining the analyzing angle.

Furthermore, by determining the intensity or rate of the specular reflection and the specular-diffuse reflection, changes in surface property that affect the specular reflection or the specular-diffuse reflection, other than the above-described pattern-like scab, can be detected. For example, for the surface finish of metal strip, such as dull finish and hairline finish, can be detected, in theory, if only there is a variation in distribution of micro-reflection-face, and the application to inspect that type of surface property is expected.

The detection and the judgment of surface flaws may naturally apply known method and means in parallel. The detail of the parallel application of known method and means is described later.

In this manner, the position of the inspection plane that is judged to have a surface flaw is tracked by a tracking means. The tracking can be conducted by calculating the time that the position of surface flaw reaches the marking means, on the basis of the transfer speed of the metal strip. The marking means applies marking on the surface of the metal strip based on the marking command generated from the tracking means.

Marking can be done by various methods depending on object and use. Any kind of marking method may be applied if only the marking is readily detected in succeeding stage. For example, printing by ink or paint, stamping using a stamper, drilling using a drilling machine, change of surface roughness using grinder or the like can be applied. For the case of ferromagnetic metal strip, a magnetic marking or the like can be applied.

The position of marking may be matched with the position of surface flaw, or may be matched thereto only in the longitudinal direction, not in the width direction. For example, if automatic feeding to a press-line as a material is adopted, the detection of marking may, in some cases, become easy by setting the marking position to a fixed position rather in width direction.

The second aspect of the Best Mode 2 is a method for manufacturing metal strip with marking, which method comprises the steps of: identifying reflected lights coming from an inspection plane of a metal strip under two or more of optical conditions different from each other; applying judgment of presence/absence of surface flaw on the inspection plane based on a combination of reflected light components under these different optical conditions; and applying marking that indicates information relating to the flaw on the surface of the metal strip based on the judgment result.

According to the second aspect of the Best Mode 2, a marking is applied to the surface of metal strip at the place where a surface flaw is judged as existing by the above-described surface flaw judging method. Since the marking to indicate the presence of surface flaw is applied, succeeding stage or user can remove the portion of the surface flaw, thus preventing the defect portion from entering the products. With the manufacturing method, the work of coil dividing to remove the surface flaw portion is significantly simplified or is eliminated, so that the production efficiency improves.

The third aspect of the Best Mode 2 is a method for working metal strip comprising the steps of: identifying reflected lights coming from an inspection plane of a metal strip under two or more of optical conditions different from each other; applying judgment of presence/absence of surface flaw on the inspection plane based on a combination of reflected light components under these different optical conditions; applying marking that indicates information relating to the flaw on the surface of the metal strip; winding the marked metal strip to prepare a coil; rewinding the coil to detect marking; avoiding or removing a specific range of the metal strip based on the information given by the marking; and applying specified working to a residual portion of the metal strip after avoiding or removing the specified range.

According to the third aspect of the Best Mode 2, marking is applied onto the surface of metal strip, similar with the second aspect of the Best Mode 2, and the metal strip is wound to form a coil. The coil is transported to a plant or the like, where the forming-work is applied to produce steel sheet. On applying the forming-work, the coil is unwound in advance to detect a marking by visual inspection or using a simple detector. When the marking is detected, the defect portion including the flaw on the metal strip is avoided or removed based on the information.

For example, when marking is applied matching the position of flaw, the range of the defect portion is the portion applied by marking. When the marking has information of kind, degree, or the like of the flaw, the determination is given on the basis of the kind and degree of flaw which becomes a defect during the forming-work. The phrase "the defect portion including the flaw on the metal strip is avoided or removed based on the information" means that the defect portion of the metal strip is cut to remove, or the feed of the metal strip to the working stage is adjusted to pass the defect portion of the metal strip, thus controlling the feed of the metal strip to the working stage not to work the defect portion.

The fourth aspect of the Best Mode 2 is a metal strip with marking having, on a portion that shows an abnormality compared with a portion of normal combination of surface reflected light components under two or more optical conditions different from each other, the marking indicating information relating to a flaw on the surface thereof.

The metal strip according to the fourth aspect of the Best Mode 2 is applied with marking at a place where the above-described surface optical analysis judged as not normal, or the position of surface flaw. Accordingly, as described above, succeeding stage or user of the metal strip can remove and prevent the portion of the abnormal part from entering the products.

The fifth aspect of the Best Mode 2 is a metal strip with marking having, on a portion that gives an abnormal quantity of light for one or both components of a specular reflection component on surface and a specular-diffuse reflection component on plurality of micro-area reflection surfaces, the marking indicating information relating thereto.

The metal strip according to the fifth aspect of the Best Mode 2 has a marking at a position where the state of specular reflection or of specular-diffuse reflection on the surface differs from that of normal portion. The term "specular-diffuse reflection" means the plane on which plurality of micro-area specular reflection planes on which the normal faces to a specified direction are distributed. Similar with the above-described aspects, the treatment of abnormal part becomes easy with the use of the metal strip.

The sixth aspect of the Best Mode 2 is a surface flaw marking device for a metal strip, described in claim 1, which marking device comprises: plurality of surface flaw inspection means including a surface flaw inspection means having a light-receiving part and a signal processing section; and a marking information preparation means that totally judges the inspection result of the surface flaw on the metal strip and prepares the marking information relating to the metal strip surface.

According to the sixth aspect of the Best Mode 2, the surface flaw inspection means having the light-receiving part and the signal processing section, in the first aspect of the Best Mode 2, is combined with an ordinary surface inspection means that inspects abnormality of the surface property such as flaw and stain by detecting size and shape of flaw and stain, or reflectance of the emitted light, or the like, thus classifying the kind and degree of abnormal portions such as surface flaw. By the procedure, total judgment is given on various kinds of abnormalities in surface properties such as abnormal specular-diffuse reflection, thus the marking of the information about these abnormalities is available.

The seventh aspect of the Best Mode 2 is a method for manufacturing metal strip with marking, of the second aspect of the Best Mode 2, comprises the step of applying judgment of presence/absence of surface flaw based on the inspection result using plurality of surface inspection methods which include the surface flaw inspection method that conducts the inspection on the inspection plane based on a combination of reflected light components identified under two or more of optical conditions different from each other.

According to the seventh aspect of the Best Mode 2, the surface flaw inspection method combines an ordinary surface inspection means with the surface flaw inspection method, of the second aspect of the Best Mode 2, that conducts inspection of the inspection plane based on a combination of reflected light components identified under two or more of optical conditions different from each other, thus classifies the kinds and degrees of surface flaws. The "ordinary surface flaw inspection method" means, for example, the surface inspection method to inspect abnormality in the surface property such as flaw and contamination, by detecting the size and shape of flaw, the reflectance of emitted light, or the like. In this manner, total judgment is given to various kinds of surface property abnormality including abnormal specular-diffuse reflection, thus applying marking the information about these abnormal parts.

The eighth aspect of the Best Mode 2 is a metal strip with marking of the fourth aspect of the Best Mode 2, comprising a metal strip with marking having, on a portion that shows an abnormality compared with a portion of normal combination of surface reflected light components under two or more optical conditions different from each other, marking indicating information relating to a flaw on the surface thereof.

According to the metal strip of the eighth aspect of the Best Mode 2, adding to the abnormal part in the third aspect of the Best Mode 2, marking is applied to the surface relating to the surface inspection result or the information of various surface properties, based on the ordinary surface flaw inspection in terms of flaw size and shape, or reflectivity of emitted light, or the like. The "abnormal part" referred in the third aspect of the Best Mode 2 means the part that, when reflected lights are separated under two or more of optical conditions, as described above, the intensity or the ratio of the reflection component differs from that of the normal part.

The ninth aspect of the Best Mode 2 is a metal strip with marking of the fifth aspect of the Best Mode, having, about the information relating to the metal strip surface containing a portion that gives an abnormal quantity of light for one or both components of a specular reflection component on surface and a specular-diffuse reflection component on plurality of micro-area reflection surfaces, marking is applied on the surface to indicate the information relating thereto.

According to the metal strip of the ninth aspect of the Best Mode 2, adding to the abnormal part in the fifth aspect of the Best Mode 2, marking is applied to the surface relating to the surface inspection result or the information of various surface properties, based on the ordinary surface flaw inspection in terms of flaw size and shape, or reflectivity of emitted light, or the like. The "abnormal part" referred in the fourth aspect of the Best Mode 2 means the part that, as described above, the state of specular reflection or specular-diffuse reflection on the surface differs from that of normal part, and, when a reflected light is separated under two or more of polarization conditions, the intensity or the ratio of the reflection component differs from the normal part.

With the above-described aspects of the Best Mode 2, the marking indicating the information about the abnormal parts of various surface flaws including abnormality in specular-diffuse reflection or about the abnormal parts of surface property is applied on the surface of metal strip. Accordingly, succeeding stage or user can notice the kind and degree of the surface flaw, thus being capable of responding to various uses and objects.

Furthermore, by applying marking on the surface of metal strip, the metal strip can be wound without cutting-off the surface flaw portion and other defective portions, which prevents from increasing the number of coils by strip cutting. Since the number of coils is not increased, the coil handling does not increase the winding work. In addition, during transfer, rewinding, and working on the coils, the handling work is reduced because the number of coils is not increased.

Figure 24:
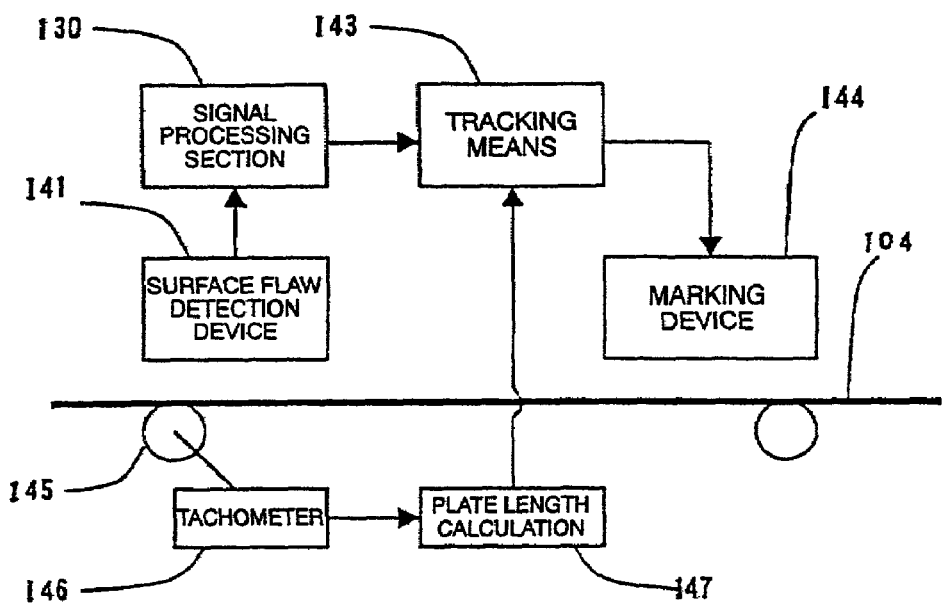
FIG. 24 is a block diagram of an example of the devices relating to the Best Mode 2 according to the present invention.

FIG. 24 shows a block diagram of an example of carrying out the present invention. A surface flaw detection device 141 identifies a light reflected from the metal strip 104 under two or more optical conditions different from each other. A signal processing section 130 judges the presence/absence of surface flaw on the inspection plane based on the combination of these reflection components.

A tracking means 143 calculates the time that the position of surface flaw arrives at a marking means. That is, a sheet length calculation means 147 coverts the position of the surface flaw into the sheet length on the basis of the rotational speed determined by a rotameter 146 attached to a transfer roll 145, and converts the covered sheet length into the time necessary to arrive at a marking means 144. When thus determined time comes, the tracking means 143 generates a command signal for marking to the marking means 144. On receiving the command, the marking means 144 applies marking on the surface of the metal strip to indicate the position by printing, drilling, or the like.

Figure 25:
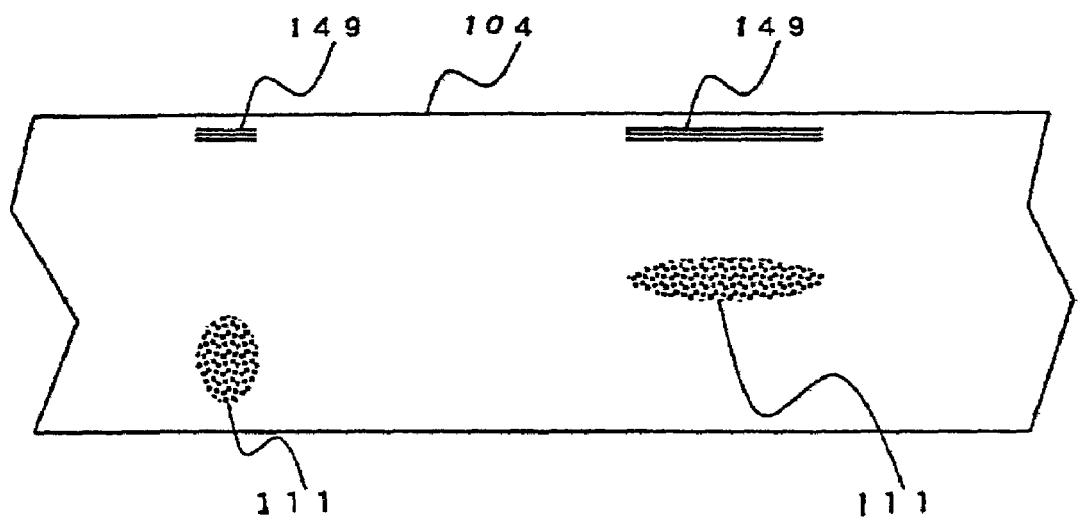
FIG. 25 is a plan view of an example of metal strip relating to the Best Mode 2 according to the present invention.

FIG. 25 shows an example of the metal strip with marking. According to the example, the position of a marking 149 matches the position of surface flaw 111 in longitudinal direction, and maintains a fixed position from an edge in the width direction. Accordingly, for applying in a press line, the marking 149 can be detected at a fixed position from an edge independent of the position of the surface flaw 111, and it is possible to give treatment such as rejection of a certain portion including the surface flaw 111, thus preventing the production of defective products.

Figure 26:
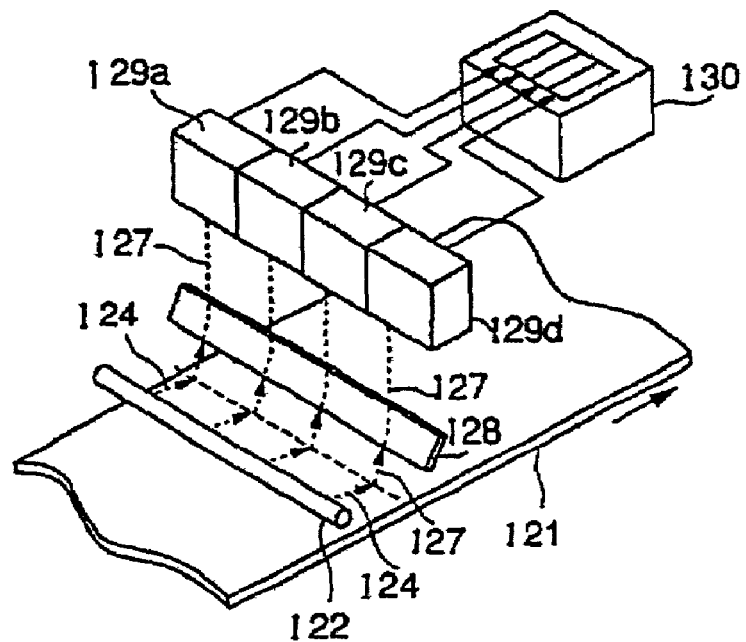
FIG. 26 is a schematic drawing of an example of rough structure of a surface flaw inspection device for the devices relating to the Best Mode 2 according to the present invention.
Figure 27:
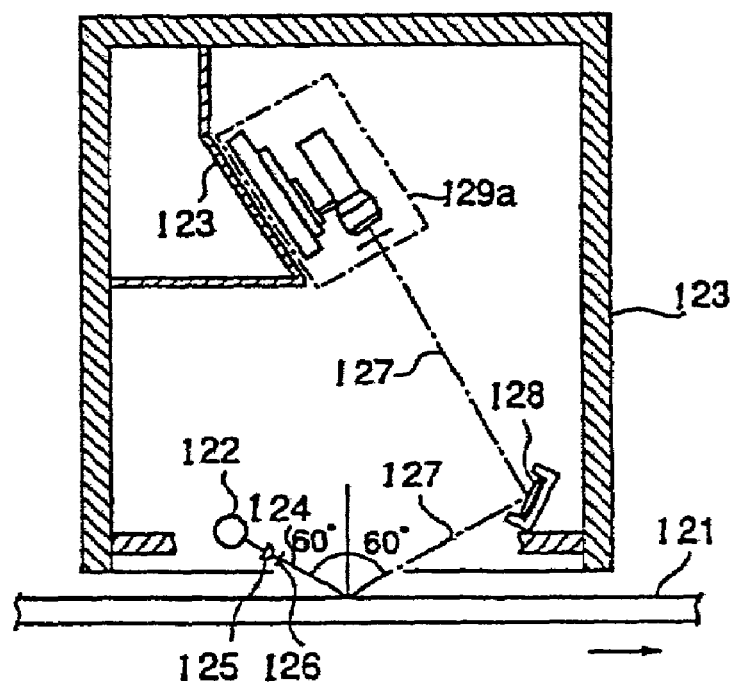
FIG. 27 is a cross sectional schematic drawing of a surface flaw detection device relating to the Best Mode 2 according to the present invention.

FIG. 26 and FIG. 27 show an example of the surface flaw detection device 141. As a linear diffusion light source 122, a transparent light-conductive rod applied with a diffuse reflection paint on a part thereof is used. A light emitted from a metal-halide light source is entered to both ends of the transparent light-conductive rod. The light coming out from the light-conductive rod of a light source 122 in diffusional mode passes through a cylindrical lens 125 and a sheet polarizer 126 with 45° polarization, then is conversed in a line with 60° of incident angle to enter over the whole width of a steel sheet 121. A reflected light 127 is further reflected by a mirror 128 located in regular reflection direction to the steel sheet, and enters camera units 129a through d, structuring the light-receiving part.

Figure 28:
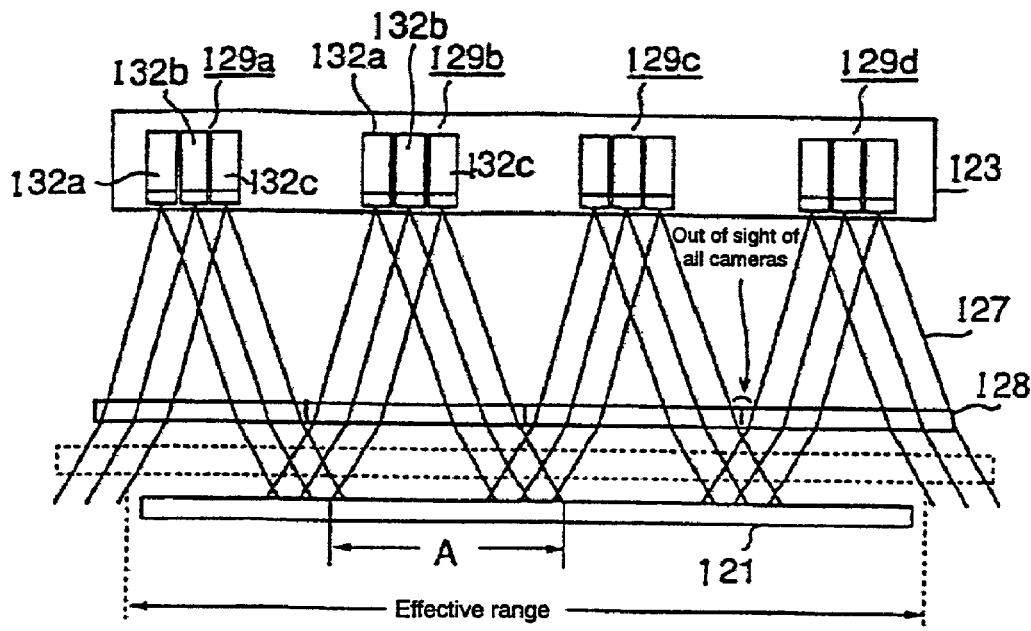
FIG. 28 illustrates an arrangement of camera units along the metal width direction, equipped in the surface flaw inspection device, relating to the Best Mode according to the present invention.

These camera units 129a through d are arranged in the sheet width direction, as shown in FIG. 28. With that positioned mirror 128, the facility can be designed in compact size. When the mirror 128 is positioned at an adequately distant from the steel sheet 121, the mirror 128 gives a region that comes outside of the view-field of all cameras, as shown in FIG. 28, thus the mirror can be structured with divided segments. The divided mirror construction decreases the fabrication cost.

Each of the camera units 129a through d in the light-receiving part comprises three linear-array cameras 132a through c, having respective analyzers 133a through c with respective analyzing angles of −45°, 45°, and 90° in front of each lens, while the light axes are in parallel to each other. The offset of the view-field of these three cameras is compensated by a signal processing section 130. With the light axes kept in parallel to each other, respective individual pixels of the three cameras 132a through c agree one-to-one to each other within the same view-field. Compared with the division of a single reflected light using a beam splitter, the method avoids loss of light quantity, and efficient measurement is available.

The light-receiving range A of individual light-receiving cameras 132a through c in each of camera units 129a through 129d overlaps in a part with the light-receiving range A of the corresponding light-receiving cameras 132a through c in each of other adjacent camera units 129a through d, as shown in FIG. 28. In other words, the light reflected from arbitrary position in the width direction on the steel sheet 121 is received by at least one of the three kinds of light-receiving cameras 132a through c in each of the camera units 129a through d.

Instead of the linear array camera, the light-receiving part may use a two-dimensional CCD camera. In addition, the light-emitting part may use a fluorescent lamp as the linear diffusional light source 122. Furthermore, a fiber light source may be applied by arranging the light-emitting end of a bundle of fibers in a line. That is, since the light emitted from each fiber has sufficiently broad angle responding to the fiber N/A, the fiber light source arranged with the fibers substantially functions as a diffusional light source.

The detail of the arrangement of plurality of cameras is described referring to FIG. 28. The plurality of camera units 129a through dare arranged at a fixed spacing therebetween. Each of the camera units 129a through d comprises three cameras 132a through c which receives light under different conditions (polarization of −45°, 45°, and 90°, respectively). These cameras are arranged in parallel to each other at a fixed spacing therebetween. Accordingly, the view-field of each camera offsets by the amount of camera distance.

The sequent order of camera arrangement in every camera unit is the same there each. For example, 45°, 90°, and −45° from left to right viewed from front side thereof. The measuring range (effective range), for example, is defined as the range that is observed under three kinds of optical conditions. And, a range where observation can be available only under one condition or only under two conditions, (range on both end portions), is concluded as ineffective, and not to be used. The camera spacing and the unit spacing are determined as a value that allows the maximum width of steel sheet to enter the measurement range (effective range).

The three cameras in each unit are not adjusted to provide the same view-field. After each camera determined the flaw candidate region, each camera is adjusted in terms of each flaw candidate region. As described above, since the view-field of each camera is offset from each other, in some cases not all of these three cameras can have a view-field for a certain flaw candidate region, (or three optical conditions cannot be satisfied). In these cases, the three optical conditions are satisfied using the results of the cameras of adjacent unit. The concept is applicable not only for receiving light of three polarized lights, but also for observing under arbitrary two or more conditions by dividing the total width of inspection body into plurality of view-fields.

Figure 29:
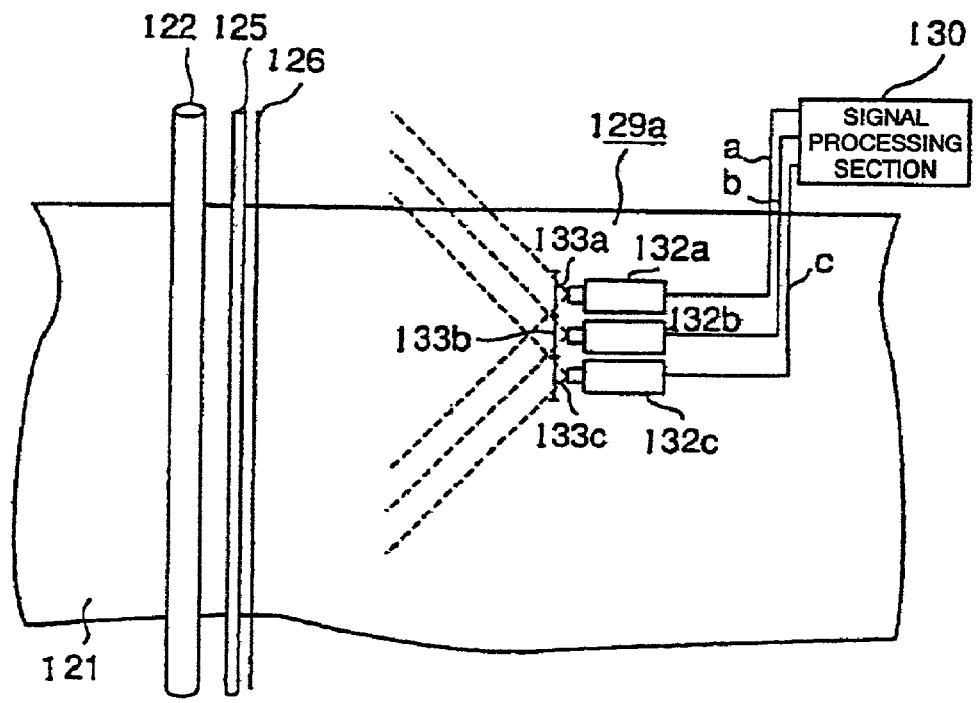
FIG. 29 illustrates an arrangement of cameras equipped in a single camera unit, relating to the Best Mode 2 according to the present invention.
Figure 30:
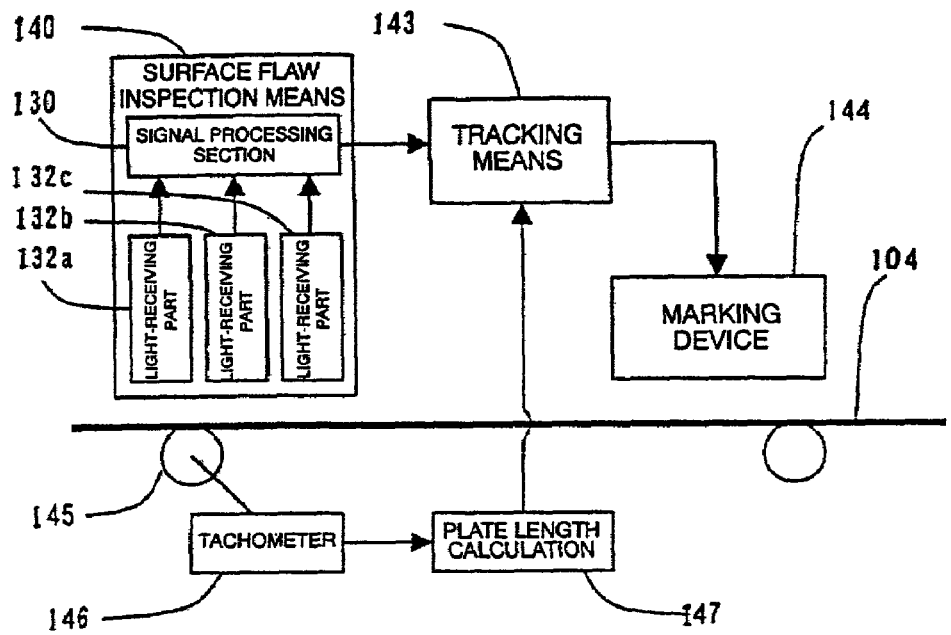
FIG. 30 is a block diagram of another example of the devices relating to the Best Mode 2 according to the present invention.

Hereinafter the plurality of light-receiving part and the signal processing section are referred to as the flaw inspection means. Then, the surface flaw marking device shown in FIG. 24 is redrawn to FIG. 30. The flaw inspection means 140 has the light-receiving parts 132a through c, (corresponding to the cameras in FIG. 28 and FIG. 29), and the signal processing section 130. The signal processing section 130 conducts signal processing to detect the above-described diffusion specular reflection component based on the intensity of the reflected light which is identified under different optical conditions, thus giving judgment of presence/absence of abnormal part. After that, similar with FIG. 24, the position of surface flaw is calculated using the tracking means 143 and the sheet length calculation means 147, and applies marking to the position of abnormal part using the marking means 144.

Figure 31:
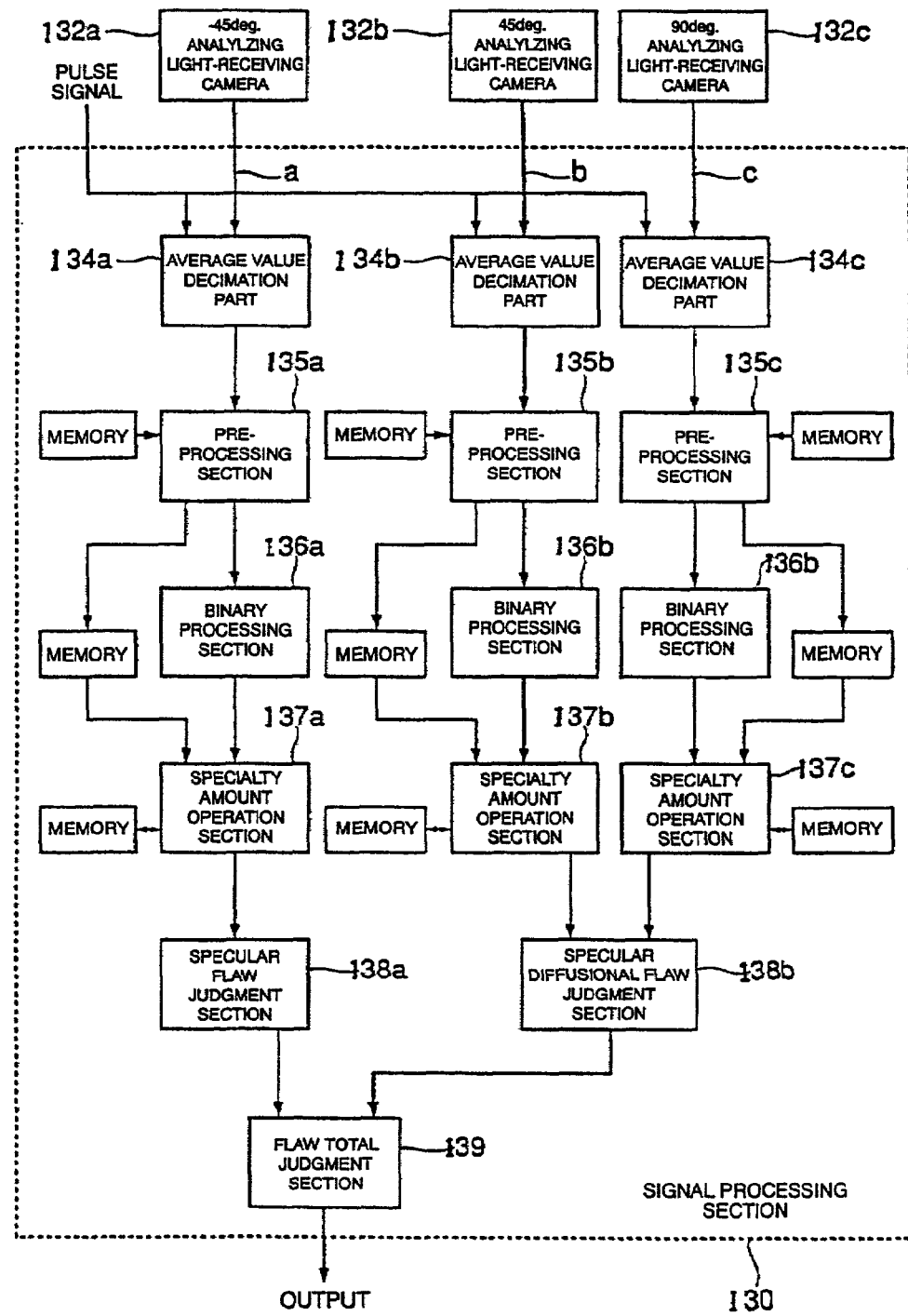
FIG. 31 is a block diagram of an example of the signal processing section of the devices relating to the Best Mode 2 according to the present invention.

As for the signal processing section, FIG. 31 shows an example of block diagram. The light intensity signals a through c coming from respective light-receiving cameras 132a through c enter respective average value decimation parts 134a through c, thus calculating the average value. After that, based on the pulse signals entered along with the movement by a certain distance in the longitudinal direction of the inspection body, the signal for a single line in the width direction is generated. By the decimation treatment, the resolution in the longitudinal direction is maintained to a fixed value. In addition, if the frequency of calculation of average value is regulated so as the moving distance in the longitudinal direction of the inspection body to not come outside of the view-field of the light-receiving cameras 132a through c, overlooking can be avoided.

Then, pre-treatment sections 135a through c compensate the irregular luminance relating to signals. The irregular luminance referred herein includes that caused from optical system, that caused from reflectivity of inspection sheet. The pre-treatment sections 135a through c detect the edge position of the steel strip and apply treatment not to mis-recognize sudden changes in signal at edge part as a flaw.

The signals completed the pre-treatment enter binary calculation sections 136a through c, where flaw candidate points are identified by comparing with preliminarily set threshold value. The identified flaw candidate points enter characteristic quantity calculation sections 137a through c, where the signal processing for flaw judgment is conducted. In the case that the flaw candidate points are in a sequential mode, characteristic quantity calculation sections 137a through c calculate the position and the characteristic quantity of, for example, starting address and ending address, and further the concentration characteristic quantity such as peak value.

The calculated characteristic quantities enter a specular flaw judgment part 138a or a specular diffusional flaw judgment part 138b depending on the optical conditions (with an analyzing angle β) of the original signals a through c. The output of the characteristic quantity calculation section 137a comes from the optical condition of original signal a as −45° analyzing (β=−45°). In this case, the characteristic quantity enters the specular flaw judgment part 138a to detect the difference in reflected light quantity between the mother material and the scabbed portion based on the specular reflection component, as described above.

On the other hand, the output of the characteristic quantity calculation sections 137b and c come from the optical conditions of original signals b and c as 45° and 90° analyzing angles (β=45° and 90°), respectively, giving difference only on the specular-diffuse reflection component. Thus, the characteristic quantity enters the specular diffusional flaw judgment part 138b to give flaw judgment on the specular-diffuse reflection component.

Finally, a flaw total judgment section 139 gives judgment on the kind and the degree of flaw on the inspection plane of the metal strip based on the output of the specular flaw judgment section 138a and the specular diffusional flaw judgment section 138b. At that moment, considering the overlap of view-field between cameras 132a through d and between camera units 129a through d, (FIG. 29), it is preferable that the result of flaw judgment based on the signals coming from cameras of adjacent camera unit is used, at need.

Figure 32:
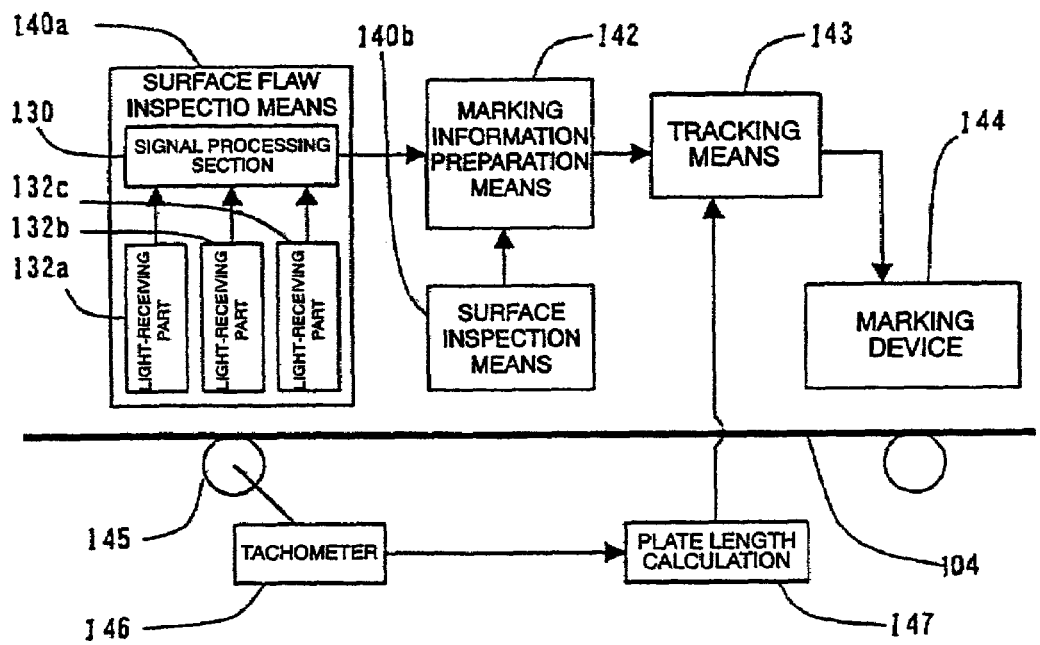
FIG. 32 is a block diagram of further example of the devices relating to the Best Mode 2 according to the present invention.

FIG. 32 shows an example of combination of the surface flaw inspection means that gives flaw judgment by detecting abnormality in the specular-diffuse reflection component and a surface flaw inspection means applying other method. The surface flaw inspection means 140a is the same with that shown in FIG. 30. That is, plurality of light-receiving parts 132a through c identify the reflected light under different optical conditions, and the signal processing section 130 detects the abnormality in the specular-diffuse reflection component to give flaw judgment.

The surface flaw inspection means of other method, 140b, may apply ordinary surface flaw inspection means such as a device with the method to give judgment by detecting surface flaw based on the size and shape of the flaw, or a device with the method to detect surface contamination and adhesion based on the reflectance of emitted light, or other variables. The surface inspection means 140b classifies the ordinary surface flaw and abnormality in surface property in terms of the kind and the degree thereof. The marking information preparation means 142 conducts total classification and ranking on various kinds of surface flaw and abnormality in surface property, including abnormality in specular-diffuse reflection, thus preparing the information for marking.

After that, the tracking means 143 and the sheet length calculation means 147 calculate the position of the surface flaw, similar with the procedure in FIG. 24. The marking means 144 applies marking to the position of abnormality based on the marking information. At that moment, preferably the information relating to the kind and degree of the surface flaw is given. The information preferably gives a detectable form expressing marking pattern, shape, strip width, or the like. If bar codes or OCR (optical character reader) are applied, further detail information can be marked.

As described above, by applying marking on the surface of metal strip, increase in the number of coils is prevented, so that the work efficiency improves during the handling of coils, including transportation and recoiling. Furthermore, during the working of metal strip, the metal strip can be fed continuously without stopping at the flaw portion, so that an efficient work is expected.

EMBODIMENTS

Figure 34:
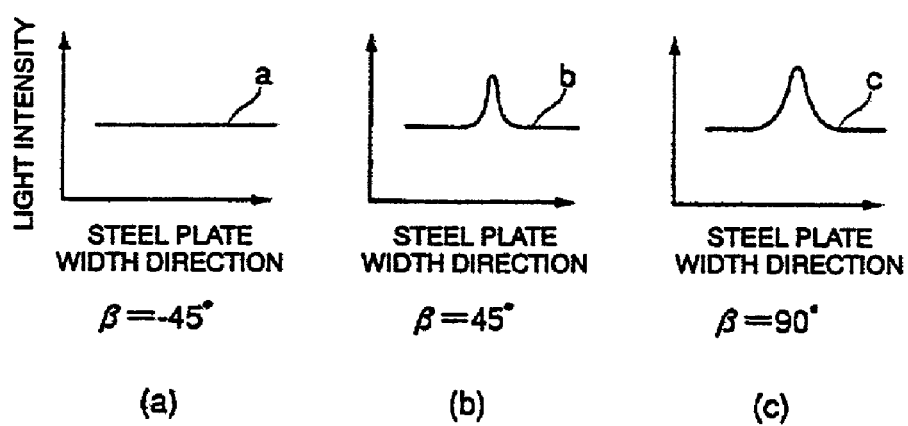
FIG. 34($a$) through ($c$) illustrate another examples of light intensity signals observed by a device relating to the Best Mode 2 according to the present invention.

FIGS. 33 and 34 show the observed results on the alloyed galvanized steel sheet in accordance with the embodiment of FIG. 26. FIG. 33 corresponds to the above-described FIG. 40(b), and FIG. 34 corresponds to FIG. 40(c). The measured flaws are the one in which the area rate in the tempered part is larger in the scabbed part than in the mother material, and the diffusional property in the non-tempered part is the same therebetween, (FIG. 40(b)), and the one in which the area rate in the tempered part gives no difference therebetween, and the diffusional property differs therebetween, (FIG. 40(c)). As for the flaw of FIG. 34 type, generally there exist angles that cannot be detected in the diffuse reflection direction. The measurement of two kinds of that type flaws, each having different angles from each other, was conducted. For comparison, the figure also shows the result of non-polarized light observation, conforming to conventional technology, on entering light with 60° of incident angle and on measuring the light from regular reflection direction (60°) and from light-receiving angle (−40°) offsetting by 20° from the incident angle. The results are summarized in Table 1.

addition, since both components can be grasped on the same light axis in the regular reflection direction to the steel sheet, the measurement free from the influence of variations in steel sheet distance and of variations of speed thereof has been realized. By setting the analyzing angle, selection of identification of the specular-diffuse reflection component at arbitrary angle has become available.

From the quality assurance point of view, that type of surface inspection device is absolutely required to not leave any non-detected flaw. The present invention actualizes, for the first time, the surface flaw marking device using a surface flaw inspection device that is applicable to wide fields including the surface-treated steel sheets without fail in detection of flaw, and the manufacturing of metal strips with marking. As a result, the surface flaw inspection that was relied on visual inspection of inspector is automated, and a simple means can notify the information to succeeding steps and to user. Thus, the use effect of the device and the method according to the present invention is significant.

TABLE 1

| Reflection characteristics at mother material and scabbed part | Undetectable angle of receiving light | Light-receiving angle in accordance with conventional technology | | Analyzing angle in embodiments | | |
|---|---|---|---|---|---|---|
| | | 60 | −40 | −45 | 45 | 90 |
| corresponding to FIG. 40(b) | −180 to 20° | ○ | X | ○ | X | Δ |
| corresponding to FIG. 40(c) | 10 to 30, 55 to 65° | X | ○ | X | Δ | ○ |
| | −50 to −30, 55 to 65° | X | X | X | ○ | ○ |

In Table 1, the symbol ○ designates detectable (large S/N value) and the symbol Δ designates undetectable (small S/N value).

Although the prior art adopts logic sum to receive light at two light-receiving angles and to remove noise, these flaws cannot be detected at two light-receiving angles at a time. Specifically, there are flaws that cannot be detected by either light-receiving angle.

To the contrary, according to the embodiment of the present invention, identification of the reflected light components corresponding to the three different light-receiving angles is done in the regular reflection direction by using analyzer. Accordingly, one of linear-array cameras can detect the flaws. Furthermore, it is easy to set optimum analyzing angle matching with the reflection characteristics of a flaw necessary to be detected.

Based on the finding that the reflection on the surface of steel sheet comprises the specular reflection component and the specular-diffuse reflection component, as described before, the present invention adopts a method to identify and grasp each component, which method comprises the steps of: using a linear diffusional light source; entering a polarized light having both p-polarized light and s-polarized light into the inspection plane; adequately setting the analyzing angle to the regular reflection direction to the steel sheet; thus identifying the component containing more of specular reflection component and the component containing more of specular-diffuse reflection component.

By the method, the unobservable flaw can be detected from the specular reflection component, and the pattern-like scabs having no significant surface irregularity, which cannot be detected in prior art, can be detected without fail. In Best Mode 3

The Best Mode 3 according to the present invention is to provide a high speed response marking device that, on applying marking flaw part, singular part, or the like detected on a metallic material by an inspection device, can easily recognize the flaw and singular part during succeeding stage and during inspection at customer, that can readily apply marking using commercially available marker pen or the like independent of kind and color of the ink, and that can be used in a line which requests tracking and high speed response of marking without wearing the tip of pen by a shock of descending pen movement and without generating flaw on the marked metallic material, thus giving accurate marking at flaw and singular part generated on the metallic material, further assuring excellent maintenance performance and economy.

The first aspect of the Best Mode 3 is a marking device to apply marking flaw and singular part on an inspection body, detected by an inspection device, which marking device comprises: a marker pen; a penholder to which the marker-pen is detachably mounted; a penholder lifting mechanism for ascending/descending the penholder together with the marker-pen; a protective cap being capable of opening/closing to protect a pen tip of the marker-pen; and a shutter mechanism to open/close the protective cap linking with the penholder lifting mechanism.

The second aspect of the Best Mode 3 is a marking device for applying marking a flaw part and a singular part on a metal member, detected by an inspection device in a continuous manufacturing line of a metal material, which marking device comprises: a marker pen; a penholder to which the marker-pen is detachably mounted; a penholder lifting mechanism for ascending/descending the penholder together with the marker-pen; a protective cap being capable of opening/closing to protect a pen tip of the marker-pen; and a shutter mechanism to open/close the protective cap linking with the penholder lifting mechanism.

The third aspect of the Best Mode 3 is the above-described marking device which further comprises a marking acceptance roll facing the pen tip of the marker-pen and being located at opposite side from the marking surface of the metal material being marked.

The fourth aspect of the Best Mode 3 is the above-described penholder having a pressing force control mechanism for the marker-pen.

The fifth aspect of the Best Mode 3 is the above-described marking device which further comprises a tracking mechanism for marking position, mounted to automatically mark a flaw part or a singular part which is detected on the metal material.

The sixth aspect of the Best Mode 3 is the above-described marking device, wherein the lifting mechanism of the penholder has at least two stages of lifting mechanism covering low speed lifting and high speed lifting.

The seventh aspect of the Best Mode 3 is the above-described marking device, which further comprises: an image pickup camera for photographing a marking image marked on the metal material; a lighting device for lighting the marked position; a judgment logic for judging acceptance/rejection of marking based on marking image signals photographed by the image pickup camera.

The eighth aspect of the Best Mode 3 is the above-described marking device, wherein the image pickup camera takes photographs of a marking area including a flaw portion, a singular part, and an adjacent area thereof, also of an area adjacent to the marking area, thus marking possible of judging acceptance/rejection of the marking even when the tracking of marking position changes to some extent.

The ninth aspect of the Best Mode 3 is the above-described marking device, wherein a monitoring device is provided to watch the output of the image pickup camera for photographing marking image.

The tenth aspect of the Best Mode 3 is above-described marking device, wherein the marker-pen has a shunting function to allow for the marker-pen to shunt when a portion such as dent, burr, and welded part on the metal material, that may damage the marker-pen, passes under the marker-pen.

The eleventh aspect of the Best Mode 3 is above-described marking device, which further comprises a dryer for drying marked ink after marking with the marker-pen.

According to the facilities of the present invention, when a marking command is generated against a flaw, a singular part, or the like generated on a metallic material such as steel sheet, the command enters the control device. The control device tracks a range between the entering point of the marking command and the marking point. The pen cap is opened just before the specified marking point, and the marking pen is descended to a waiting position. Immediately before the marking point passes directly beneath the marking pen, the marking pen is pressed against the marking part on the metallic material to conduct marking.

On completing the marking, the marking pen returns to the original position, and the pen cap is applied to cover the marking pen for preventing the drying thereof. Accordingly, the mechanism can be applied to a line requesting marking tracking and high speed response to assure accurate marking on flaw and singular part generated on metallic material.

According to the present invention, the marking is applied not only to notify the flaw position to user but also to cover the flaw part. And the range of marking is clearly indicated so that the user can readily recognize the range of defective portion. As a result, the cut-off treatment of the defective portion is conducted without fail, which avoids troubles in succeeding stages.

The marking covers the marking area covering the flaw part in terms of flaw position and length, ($\alpha 1$+flaw length+$\alpha 2$), and does not track the flaw part. The marking area information is received from a host flaw detection device to track the marking area.

The mark sensor receives the marking results within a range of ($\alpha 3$+flaw length+$\alpha 4$) which is longer than the above-described range ($\alpha 1$+flaw length+$\alpha 2$), thus evaluates the percentage of the marking within the working range ($\alpha 3$+flaw length+$\alpha 4$) of the marking sensor. Consequently, judgment of good/bad marking can be given even when the flaw position tracking varies to some extent.

The present invention is applicable not only to metallic materials but also to other inspection bodies including paper, film, rubber, polyvinylchloride, cloth, and the like.

Figure 51:
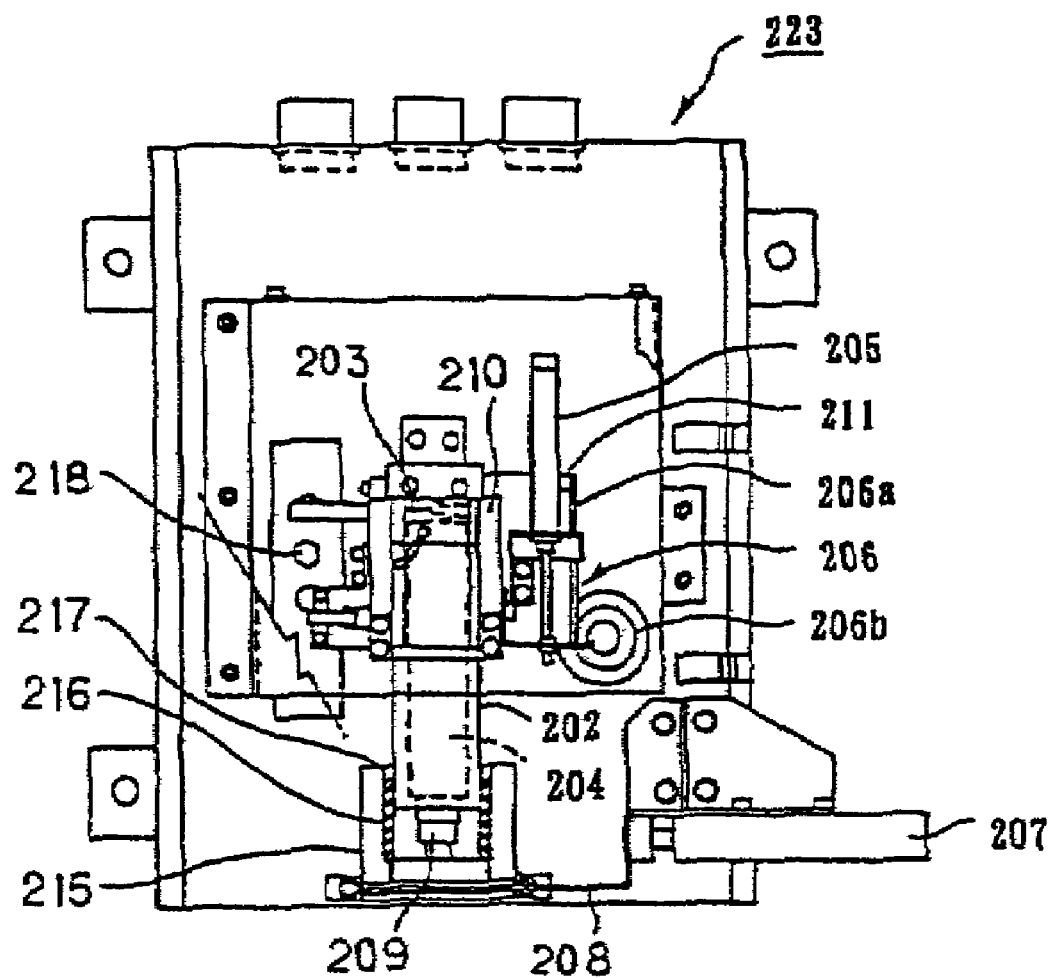
FIG. 51 shows a rough vertical cross sectional view of the devices relating to the Best Mode 3 according to the present invention.
Figure 52:
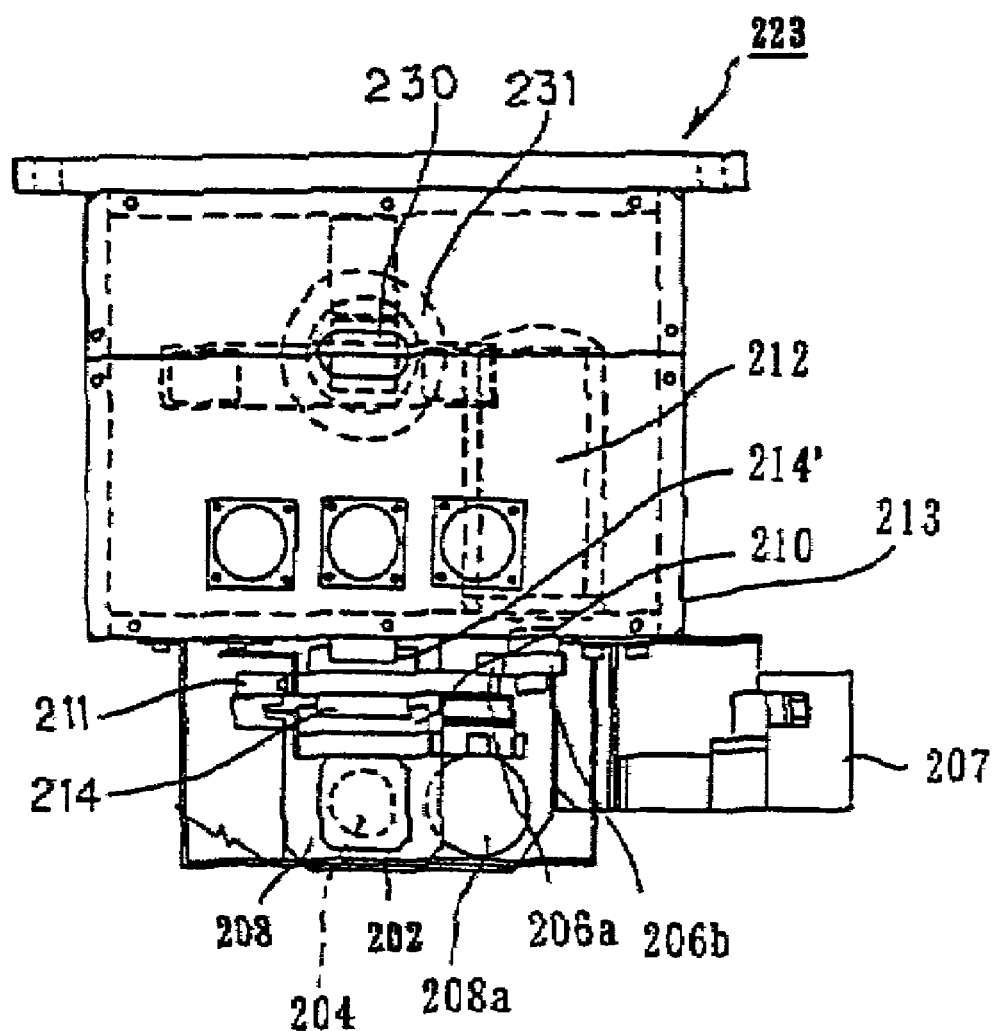
FIG. 52 shows a rough plan view of the devices of FIG. 51.
Figure 53:
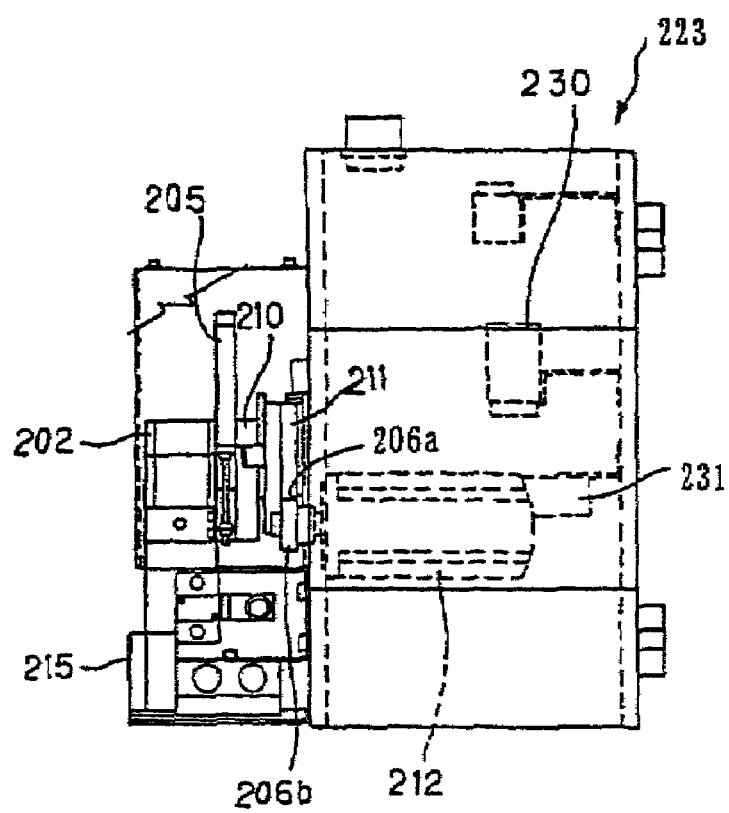
FIG. 53 shows a rough side view of the device of FIG. 51.

The following is the description of the present invention referring to the drawings. FIG. 51 is a rough vertical cross sectional view of the devices relating to the Best Mode 3 according to the present invention. FIG. 52 shows a rough plan view of the devices of FIG. 51. FIG. 53 shows a rough side view of the device of FIG. 51. As shown in these figures, the marking device 223 according to the present invention comprises: a slide table 210; a cylindrical penholder 202 supported by the slide table 210; a marker pen 204 which is detachably inserted into the penholder 202; a support plate 211; a hydraulic cylinder 205 as a penholder lifting mechanism which is mounted to the support plate 211 to lift the marker pen 204 at a high speed together with the penholder 202 using the slide table 210; a lifting motor 212 and a rack and pinion 206 as also a penholder lifting mechanism to lift the slide table 210 which is supported by the penholder 202 at a low speed along the support plate 211; a protective cap 215 having an opens/closes opening to protect the pen tip of the marker pen 204; and a shutter 208 which automatically open/close thereof linking with the hydraulic cylinder 205 as a penholder lifting mechanism and with the rack and pinion 206.

The penholder 202 is in a cylindrical shape which upper end is closed and lower end is opened. The marker pen 204 is detachably inserted into the penholder 202 while projecting the pen tip 209 from the lower open edge of the penholder 202. The marker pen 204 is caught by a spring 203 attached to the upper face of the penholder 202, while the pressing force is adjusted. The marker pen 203 is a commercially available one independent of the ink color and kind, and the marker pen 203 is readily detachable.

The slide table 210 to which the penholder 202 is mounted ascends/descends at a high speed by the action of the hydraulic cylinder 205 under a guide of a guide 214 formed on the support plate 211. To one end of the support plate 211, a rack 206*a* is provided, which rack 206*a* is caught by a pinion 206*b* which is rotated by a motor 212 mounted on a body 213. Thus, the support plate 211 ascends/descends at a low speed by the rotating pinion 206*b* under the guide of a guide plate 214'.

As described above, both the penholder 202 and the marker pen 204 ascends/descends at low speeds by the rack and pinion 206 and at high speeds by the hydraulic cylinder 205 in total 202 steps, so that the marking action can be performed in a short time without damaging the pen tip of the marker pen 204. The lifting mechanism of the penholder may be with two steps of above-described low speed and high speed, or with three or more steps. The above-described spring 203 that catches the hydraulic cylinder 205 and the marker pen 204 by the penholder 202 also has a function of a pressing force adjusting mechanism for the marker pen 204.

The protective cap 215 is in a cylindrical shape opened at upper end thereof. The inner diameter of the protective cap 215 is almost the same as the outer diameter of the penholder 202. The lower part of the penholder 202 is inserted into the marker pen 204 fitting together. At the bottom of the protective cap 215, an opening is formed to allow coming in and going out of the lower part of the penholder 202 together with the marker pen 204. To open/close the opening, a shutter 208 having an opening 208a with nearly equal diameter with that of above-described opening is located in a manner to be horizontally movable by a shutter cylinder 207. A bushing 216 is attached to the inner periphery of the protective cap 215, and a seal 217 is attached to the periphery of the upper opening.

By horizontally moving the shutter 208 using the shutter cylinder 207 to match the opening 208a to the opening at the bottom of the protective cap 215, the pen tip 209 of the marker pen 204 can be projected from the opening 208a of the shutter 208 together with the penholder 202. And, by closing the opening at the bottom of the protective cap 215 using the shutter 208, the pen tip 209 of the marker pen 204 can be protected. A sequence circuit includes the automatic operation of the open/close of the opening of the protective cap 215 by the shutter 208 under a link with the hydraulic cylinder 205 and the rack and pinion 206 as a penholder lifting mechanism.

FIG. 51 shows a sensor 218 which confirms the ascend/descend of the penholder 202. FIG. 52 and FIG. 53 show a CCD camera 230 mounted in the body 213 to take photographs of marking images, and a lighting device 231 for the marking part.

Figure 54:
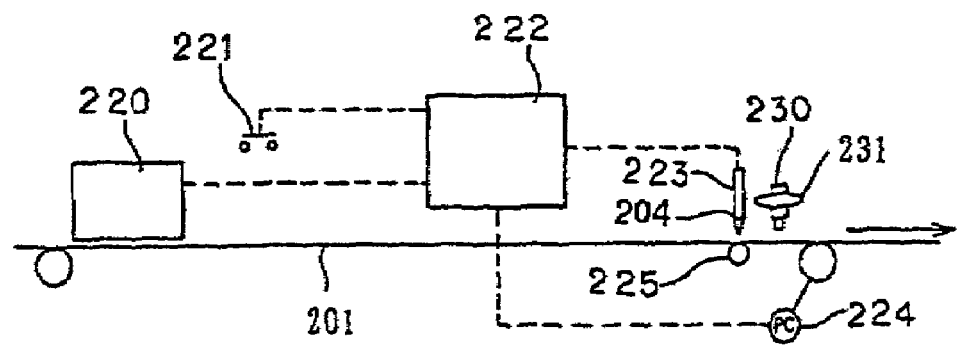
FIG. 54 illustrates a steel sheet manufacturing line provided with the devices relating to the Best Mode 3 according to the present invention.

FIG. 54 illustrates a steel sheet manufacturing line provided with the devices relating to the Best Mode 3 according to the present invention. As shown in the figure, along the transfer line of the steel sheet 201 which continuously moves in the arrow direction, there are provided an inspection device 220 such as a flaw inspection device, a width inspection device, and a thickness inspection device, to detect flaw and singular part on the steel sheet 201, an entering switch 221 for the case of manual marking commanding, a marking control device 222, and a marking device 223.

Beneath the marking device 23, a marking receiving roll 225 is located at opposite side to the marking face of the steel sheet 201, facing the pen tip 209 of the marker pen 204. With that type of marking receiving roll 225, wear of pen tip resulted from the shock of descending marker pen 204 and generation of flaw on the surface of the marked steel sheet 201 are prevented.

The signal of flaw and singular part on the steel sheet 201 detected by the detection device 220, or the marking specification signal generated from the entering switch 221, is transmitted to the marking control device 222. The marking control device 222 receives the tracking pulse generated from the pulse generator 224 for line tracking, and tracks the position to be marked on the steel sheet 201. The marking device 223 receives the marking command which is resulted from the tracking, from the marking control device 222, thus conducts the marking to flaw or singular part of the steel sheet 201.

Figure 55:
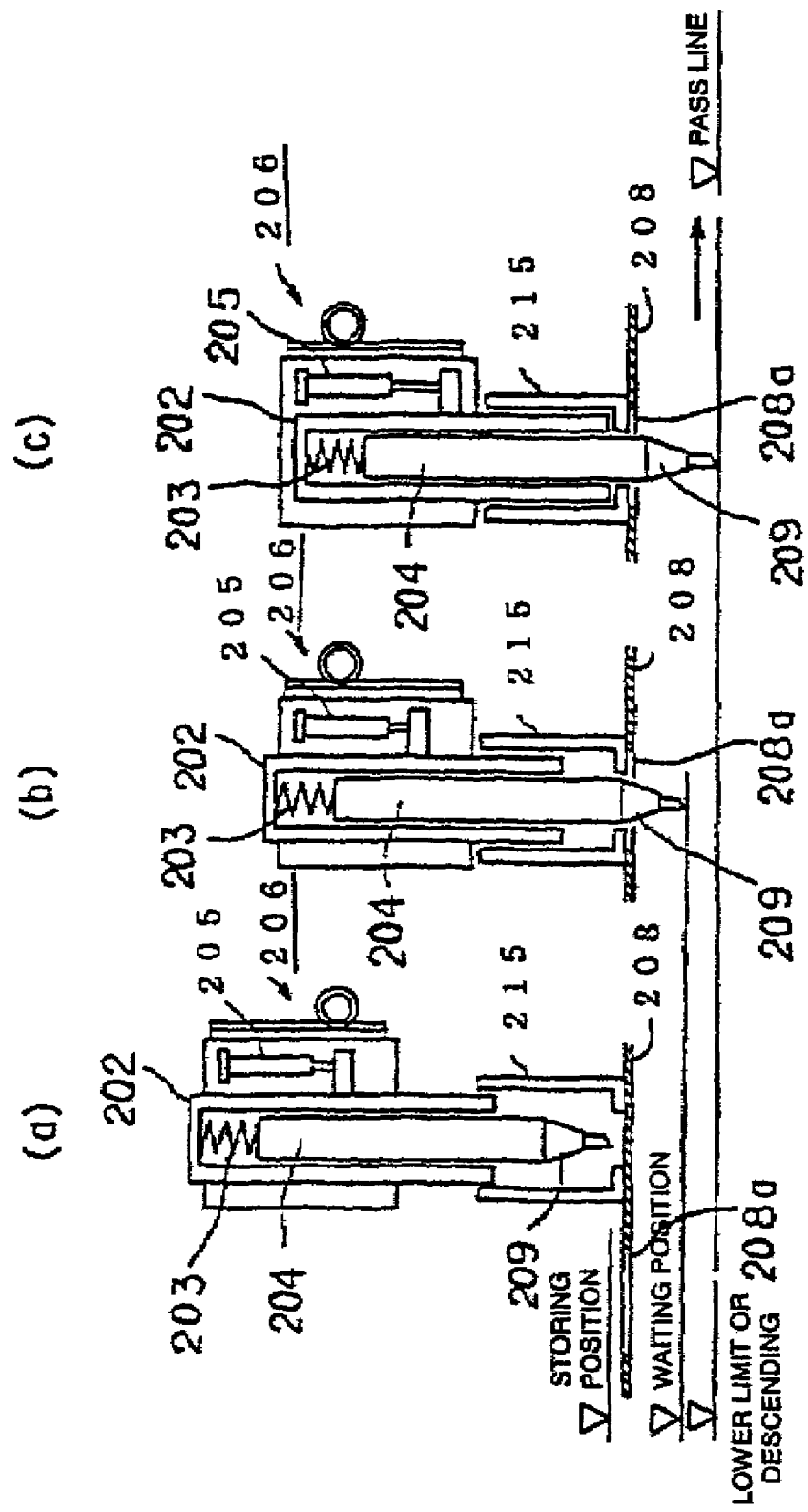
FIG. 55(*a*) through (*c*) illustrate the action of the devices relating to the Best Mode 3 according to the present invention.

The following is the description about the working of the facilities according to the present invention referring to FIG. 54 and FIG. 55. The marking control device 222 generates a marking waiting command at a point several meters before the marking specified place on the steel sheet 201. On receiving the waiting command, the lifting motor 212 of the marking device 223 starts to make the support plate 211 of the slide table 210 descend at a low speed by the rack and pinion 206 so as the pen tip 209 of the marker pen 204 to protrude from the opening of the protective cap 215 and to position the pen tip 209 at a waiting position, as shown in FIG. 55(b), and further the shutter cylinder 207 is automatically actuated linking therewith, thus the opening of the protective cap 215 is opened by moving the shutter 208.

Next, based on the marking command generated from the marking control device 222, the hydraulic cylinder 205 starts to descend the penholder 202 to the lower limit position at a high speed, as shown in FIG. 55(c), thus applying marking on the steel sheet 1.

The marking command generated from the marking control device 222 is a gate signal, and the marking is conducted during the state of gate opened. When the gate signal is released, the actuation of the hydraulic cylinder 205 makes the penholder 202 ascend to enter the waiting mode.

If there comes no succeeding marking command, the lifting motor 212 is actuated to ascend the support plate 211 to which the penholder 202 is mounted to the holding position shown in FIG. 55(a), then the shutter cylinder 207 is actuated to close the opening of the protective cap 215 by the shutter 208, thus preventing the drying of pen tip 209 of the marker pen 204.

Even during the series of actions, when a succeeding marking command is received, the logic of the marking control device 222 performs immediate marking.

Since the marking pressing force cannot be defined to a single value owing to the variations in the state of pen tip, the state of ink filling, or the like, the pressing force is controlled by the tension adjustment of the spring 203 or the pressure adjustment of the hydraulic cylinder 205 taking into account of these states.

Since blurred ink of marking is expected, a marking recognition device such as CCD camera 230 is provided. Logic to judge the acceptance/rejection of marking is provided in the marking control device 222. As the image pick up camera, above-described CCD camera, a linear-array cameras, or the like can be used.

Figure 56:
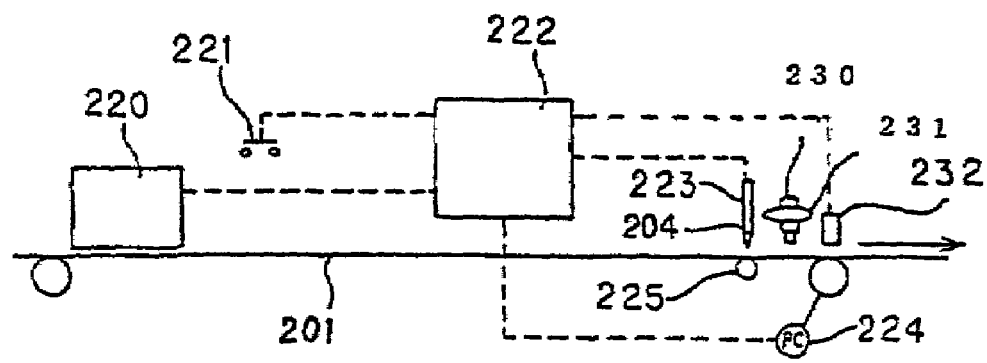
FIG. 56 is a rough sketch of a steel sheet manufacturing line provided with the devices (providing a dryer) relating to the Best Mode 3 according to the present invention.

FIG. 56 is a rough sketch of the steel sheet manufacturing line provided with a drier 232 to dry the marked ink, (hereinafter referred to as the "mark ink"), immediately after applying the marking. As shown in FIG. 56, installation of the drier 232 allows to effectively drying the mark ink immediately after marking, thus preventing the ink transferring during succeeding stages. The drying is preferred to be applied immediately after marking. However, the drying may be given before or after the camera. In any case, the drying is given after marking.

Figure 57:
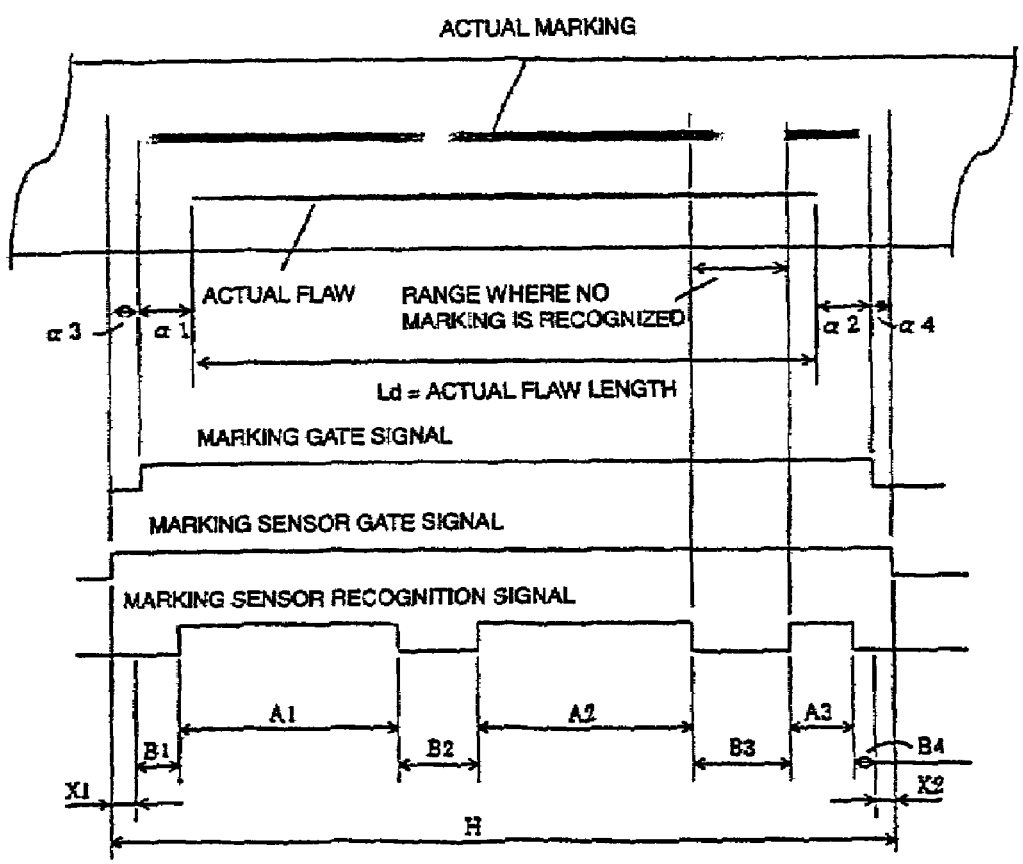
FIG. 57 illustrates the marking state on a steel sheet relating to the Best Mode 3 according to the present invention.

FIG. 57 shows the marking state on a steel sheet, comparing actual markings with the marking diagram. As shown in FIG. 57, the continuous marking line, in principle, is broken as in the cases of A1, A2, and A3, giving spacing of B2 and B3, respectively, caused from the vertical movements of traveling steel sheet and from the condition of pen tip of the marker pen 204, and, as seen in adjacent B1 and B4, the touch delay of the marker pen 204 gives thin marking or lack of marking. The zones of X1 and X2 are insensitive zones.

In that situation, the marking images in the marking range H are photographed by a CCD camera, and the photograph is sent to the marking control device 222, where the acceptance/rejection of the marking is judged on the basis of the following equation.

$$(A1+A2+A3)/\{H-(X1+X2)\} \geq S1$$

where,

An designates the range where the marking cannot be recognized;

Bn designates the range where the marking cannot be recognized;

Xn designates the insensitive zone, and Sn designates the constant for judging acceptance/rejection of the marking.

The area to be marked against the actual flaw length Ld on the steel sheet is defined as ($\alpha1$+flaw length+$\alpha2$), and the marking gate signal is generated.

On the other hand, the mark sensor gate signal has a working range of the above-given one plus $\alpha3$ and $\alpha4$. That is, the mark sensor gate signal is a range of actual flaw length Ld plus ($\alpha1+\alpha2+\alpha3+\alpha4$).

To compensate the difference of surface state on the steel sheet 201, the threshold value of output signal of the CCD camera is set beginning from superior position for individual grades of the steel sheet, thus giving judgment of the acceptance/rejection of marking. The procedure is a logic to judge the acceptance/rejection of marking gate signals based on the percentages of portions excluding the insensitive parts and of marking detection parts.

Although the figure does not include, a monitoring device to watch the output of CCD camera is added to the facilities to allow continuous monitoring the output of CCD camera.

By adding a shunt function to the marker pen, the marker pen can avoid damage and protect the facilities by temporarily shunting the marker pen in case that special portions such as hole, curl up, welded part to damage the marker pen passes under the marker pen.

The present invention is applicable not only to metallic materials but also to other inspection bodies including paper, film, rubber, polyvinylchloride, and cloth.

As described above, according to the present invention, for a coil or the like which is shipped from a continuous manufacturing line of metallic materials such as steel sheets, flaw and singular part which are detected by an inspection device such as flaw inspection device, width inspection device, thickness inspection device, installed in the line, are automatically marked, thus making easy for recognizing the flaw and singular part in succeeding stage or during customer inspection, and allowing to automatic cutting off of these flaw and singular part. Furthermore, other kinds of inspection body such as paler, film, rubber, polyvinylchloride, and cloth can be applied. In addition, since commercially available marker pen is detachable at ease independent of the kind and color of ink, the facilities are superior in assuring excellent maintenance performance and economy, which provides useful effectiveness in industrial point of view.

What is claimed is:

1. A method for marking a defect, comprising the steps of:
    (a) arranging a surface defect tester to detect a surface flaw and an ink marker device having a felt impregnated with ink to mark the defect at a defect position, in a continuous processing line of a steel sheet;
    (b) detecting the surface flaw on the steel sheet using the surface defect tester;
    (c) determining a defect name, defect grade, defect length, and defect position in a width direction of the steel sheet, on the basis of information regarding the detected surface flaw, and identifying the surface defect in terms of harmful defect, injudicable defect, and harmless defect;
    (d) tracking the defect position for each harmful defect and injudicable defect;
    (e) marking the surface defect at the defect position by pressing the felt on the steel sheet to fix the ink on the surface of the steel sheet when the defect reaches the ink marker device;
    arranging an internal defect tester to detect a defect inside of the steel sheet; and
    determining the defect length and the defect position in the width direction of the steel sheet, on the basis of the detected flaw information, and identifying the defect in terms of harmful defect and harmless defect,
    wherein the step of marking comprises changing a defect marking position based on the defect information in the width direction of the steel sheet, given by the surface defect tester and the internal defect tester, and marking the defect.

2. The method of claim 1, wherein the step of identifying the defect comprises identifying harmful defect, injudicable defect, and harmless defect, based on the defect name, the defect grade, the detect length, the defect position in the width direction of the steel sheet, and a use of the steel sheet.

3. The method of claim 1, wherein the step of identifying the defect in terms of harmful defect and harmless defect comprises identifying the harmful detect and harmless defect, based on the defect length, the defect position in the width direction of the steel sheet, and a use of the steel sheet.

4. A method for marking a defect, comprising the steps of:
    (a) arranging a surface defect tester to detect a surface flaw and a marker device to mark the defect at a defect position, in a continuous processing line of a steel sheet;
    (b) detecting the surface flaw on the steel sheet using the surface defect tester;
    (c) determining a defect name, defect grade, defect length, and defect position in a width direction of the steel sheet, on the basis of information regarding the detected flaw, and identifying the surface defect in terms of harmful defect, injudicable detect, and harmless defect;
    (d) tracking the defect position for each harmful defect and the injudicable defect;
    (e) marking the defect to the defect position when the defect reaches the marker device; and
    (f) re-judging a defect which is identified as an injudicable defect using the surface defect tester to identify harmful defect and harmless defect by an inspector.

5. The methodg of claim 4, wherein the step of re-judging a defect comprises:
    generating an alarm regarding a defect that is identified by the surface defect tester as an injudicable defect;
    automatically reducing a travelling speed of the steel sheet; and
    re-judging the injudicable defect by an inspector.

6. The method of claim 4, wherein the step of re-judging a defect comprises:
    generating a display image of the detect and a display image of the defect position for a defect that is identified as an injudicable defect by the surface defect tester; and
    re-judging the injudicable defect by an inspector.

7. The method of claim 1, wherein the step of marking further comprises changing the defect marking position depending on use of the steel sheet, and marking the defect.

8. The method of claim 1, wherein the step of marking further comprises identifying harmful defect and injudicable defect, and marking the defect.

9. The method of claim 1, wherein the step of marking further comprises marking with a different color for each of a plurality of steel sheet grades.

10. A method for marking a defect comprising the steps of:
(a) arranging a surface defect tester to detect a surface flaw and an ink marker device having a felt impregnated with ink to mark the defect at a defect position, in a continuous processing line of a steel sheet;
(b) detecting the surface flaw on the steel sheet using the surface defect tester;
(c) determining a defect name, defect grade, defect length, and defect position in a width direction of the steel sheet, on the basis of information regarding the detected surface flaw, and identifying the surface defect in terms of harmful defect, injudicable defect, and harmless defect;
(d) tracking the defect position for each harmful defect and injudicable defect;
(e) marking the surface defect at the defect position by pressing the felt on the steel sheet to fix the ink on the surface of the steel sheet when the defect reaches the ink marker device; and,
(f) arranging a defect marking detection device at a downstream side of the ink marker device and monitoring a marking state,
wherein the step of monitoring comprises changing a threshold value of the defect marking device depending on a grade of the steel sheet and monitoring the marking state.

11. The method of claim 1, further comprising the step of arranging the marker device and a defect marking detection device as a set, and letting these devices track the defect marking position, and monitoring a marking state.

12. The method of claim 1, further comprising the step of arranging an ink drying device at a downstream side of the ink marker device.

13. The method of claim 1, further comprising the step of installing the ink marker device, a defect marking detection device, and an ink drying device, as a set, and letting these devices track the defect marking position, and monitoring a marking state.

14. The method of claim 1, wherein the step of identifying harmful defect, injudicable defect, and harmless defect comprises identifying harmful defect, injudicable defect, and harmless defect, by changing a threshold value for each of the harmful defect and the harmless defect depending on a use of the steel sheet.

15. The method of claim 1, further comprising the steps of:
arranging a defect marking detection device at a downstream side of the marker device to detect defect information; and
reflecting the detected detect information on a defect removing action.

16. A method for marking a defect comprising the steps of:
arranging a surface defect tester to detect a surface flaw and an ink marker device having a felt impregnated with ink to mark the defect at a defect position, in a continuous processing line of a steel sheet;
detecting the surface flaw on the steel sheet using the surface defect tester;
determining a defect name, defect grade, defect length, and defect position in a width direction of the steel sheet, on the basis of information regarding the detected surface flaw, and identifying the surface defect in terms of harmful defect, injudicable defect, and harmless defect;
tracking the defect position for each harmful defect and injudicable defect;
marking the surface defect at the defect position by pressing the felt on the steel sheet to fix the ink on the surface of the steel sheet when the defect reaches the ink marker device;
arranging a defect marking detection device and a cleaning device at a downstream side of the ink marker device;
reflecting the defect information detected by the defect marking detection device on a defect removing action; and
re-judging the injudicable defect by an inspector, and, in the case where the defect is judged a harmless defect, cleaning the marking ink with the cleaning device.

17. The method of claim 1, wherein the ink marker device is an abrasive member marker device.

18. A method for producing a defect-marked steel coil, comprising the steps of:
providing a defect-detecting device which detects a defect and an ink marker device having a felt impregnated with ink in a continuous processing line of a steel sheet;
determining a harmful defect based on a signal from the defect detecting device; and
marking the harmful defect at a defect-detected position on the steel sheet by pressing the felt on the steel sheet to fix the ink on a surface of the steel sheet, when the harmful defect reaches the marker device,
wherein the pressing of the felt is carried out by pressing the felt on the steel sheet with a pressing force of 100 to 500 g.

19. The method of claim 18, wherein the defect-detecting device is at least one device selected from the group consisting of a surface-defect detecting device and an internal-defect detecting device.

20. The method of claim 18, wherein marking the harmful defect comprises:
setting a marking length so as to cover the harmful defect; and
marking the harmful defect.

21. The method of claim 18, wherein the ink is removable by a weak alkali cleaning agent.

22. The method of claim 18, wherein marking the harmful defect comprises marking the harmful defect with a line having a width of from 3 to 10 mm.

23. The method of claim 18, wherein determining the harmfuldefect comprises:
detecting defect candidates by using the defect-detecting device;
identifying defect grades based on the signal from the defect-detecting device; and
classifying each of the defect candidates as being either harmful or harmless.

24. The method of claim 18, wherein determining the harmful defect comprises:
detecting defect candidates by using the defect-detecting device;
identifying defect grade and defect length based on the signal from the defect-detecting device; and classifying each of the defect candidates as being either harmful or harmless.

25. The method of claim 18, wherein:

determining the harmful defect comprises classifying a defect candidate as being either harmful, unjudgeable, or harmless; and marking the harmful defect comprises marking the harmful defect, or an unjudgeable defect, at the defect-detected position on the steel sheet, when the harmful defect or the unjudgeable defect reaches the marker device.

26. The method of claim 18, further comprising:

providing a defect-marking detection device on a downstream side of the marker device; and confirming a marking condition using the defect-marking detection device.

27. A method for producing a defect-marked steel coil, comprising the steps of:

feeding a steel coil having information regarding an identified harmful defect into a continuous processing line of a steel sheet, said continuous processing line including an ink marker device having a felt impregnated with ink; and marking the harmful defect based on the information regarding the identified harmful defect by pressing the felt on the steel sheet to fix the ink on a surface of the steel sheet, when the harmful defect reaches the marker device, wherein the pressing of the felt is carried out by pressing the felt on the steel sheet with a pressing force of 150 to 500 g.

28. The method of claim 27, wherein marking the harmful defect comprises:

setting a marking length so as to cover the harmful defect; and marking the harmful defect.

29. The method of claim 27, wherein the ink is removable by a weak alkali cleaning agent.

30. The method of claim 27, wherein marking the harmful defect comprises marking the harmful defect with a line width of from 3 to 10 mm.

31. The method of claim 27, wherein said steel coil is a steel coil whose candidate defects were detected using at least one device selected from the group consisting of a surface-defect detecting device and an internal-defect detecting device, and wherein the candidate defects were classified as being either harmful or harmless based on a signal from said at least one device.

32. The method of claim 27, wherein said steel coil is a steel coil whose candidate defects were detected using at least one device selected from the group consisting of a surface-defect detecting device and an internal-defect detecting device, wherein a defect grade and defect length were identified based on a signal from the defect-detecting device, and wherein the candidate defects were classified as being either harmful or harmless.

33. The method of claim 27, wherein:

said steel coil is a steel coil whose defects were classified as being either harmful, unjudgeable, or harmless; and marking the harmful defect comprises marking the harmful defect or an unjudgeable defect, at a defect-detected position on the steel sheet, when the harmful defect or the unjudgeabte defect reaches the marker device.

34. The method of claim 27, further comprising:

providing a defect-marking detection device on a downstream side of the marker device; and confirming a marking condition using the defect-marking detection device.

35. A defect-marked steel coil, having a mark made by marking a harmful defect at a defect position on a steel sheet by pressing a felt impregnated with ink on the steel sheet to fix the ink on a surface of the steel sheets, wherein the felt is pressed to the steel sheet with a pressing force of 100 to 500 g.

36. The defect-marked steel coil of claim 35, wherein said mark has a marking length so as to cover the harmful defect.

37. The defect-marked steel coil of claim 35, wherein the ink is removable by a weak alkali cleaning agent.

* * * * *